United States Patent [19]

Schoen et al.

[11] Patent Number: 5,434,261

[45] Date of Patent: Jul. 18, 1995

[54] BENZO-FUSED LACTAMS PROMOTE RELEASE OF GROWTH HORMONE

[75] Inventors: William R. Schoen, Edison; Matthew J. Wyvratt, Jr., Mountainside, both of N.J.

[73] Assignee: Merck & Co., Inc., Rahway, N.J.

[21] Appl. No.: 97,149

[22] Filed: Jul. 26, 1993

[51] Int. Cl.$^6$ .................. C07D 223/16; C07D 243/12; C07D 281/10; A61K 31/55
[52] U.S. Cl. .................... 540/461; 540/517; 540/521; 540/523
[58] Field of Search ................ 540/461, 517, 521, 523

[56] References Cited

U.S. PATENT DOCUMENTS

| | | | |
|---|---|---|---|
| 4,411,890 | 10/1983 | Momany | 424/177 |
| 5,206,235 | 4/1993 | Fisher et al. | 514/213 |
| 5,283,241 | 2/1994 | Bochis et al. | 514/183 |

*Primary Examiner*—Robert T. Bond
*Attorney, Agent, or Firm*—J. Eric Thies; David L. Rose

[57] ABSTRACT

There are disclosed certain novel compounds identified as benzo-fused lactams which promote the release of growth hormone in humans and animals. This property can be utilized to promote the growth of food animals to render the production of edible meat products more efficient, and in humans, to increase the stature of those afflicted with a lack of a normal secretion of natural growth hormone. Growth promoting compositions containing such benzo-fused lactams as the active ingredient thereof are also disclosed.

6 Claims, No Drawings

BENZO-FUSED LACTAMS PROMOTE RELEASE OF GROWTH HORMONE

BACKGROUND OF THE INVENTION

Growth hormone, which is secreted from the pituitary, stimulates growth of all tissues of the body that are capable of growing. In addition, growth hormone is known to have the following basic effects on the metabolic process of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. The instant compounds are non-peptidyl agents for promoting the release of growth hormone which may be administered parenterally, nasally or by the oral route.

SUMMARY OF THE INVENTION

The instant invention covers certain benzo-fused lactam compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the benzo-fused lactam compounds. It is a further object of this invention to describe procedures for the preparation of such compounds. A still further object is to describe the use of such compounds to increase the secretion of growth hormone in humans and animals. A still further object of this invention is to describe compositions containing the benzo-fused lactam compounds for the use of treating humans and animals so as to increase the level of growth hormone secretions. Further objects will become apparent from a reading of the following description.

DESCRIPTION OF THE INVENTION

The novel benzo-fused lactams of the instant invention are best described in the following structural formula I:

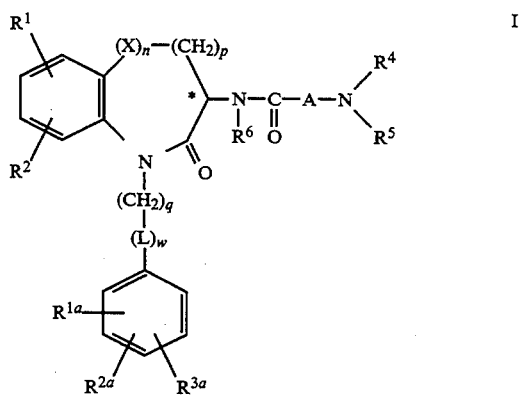

where L is

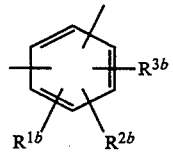

$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, $C_1$–$C_3$ perfluoroalkoxy, —S(O)$_m$R$^{7a}$, cyano, nitro, R$^{7b}$O(CH$_2$)$_v$—, R$^{7b}$COO(CH$_2$)$_v$—, R$^{7b}$OCO(CH$_2$)$_v$—, R$^{12a}$R$^{12b}$N(CH$_2$)$_v$—, R$^{12a}$R$^{12b}$NCO(CH$_2$)$_v$—, R$^{12a}$R$^{12b}$NCOO(CH$_2$)$_v$—, phenyl or substituted phenyl where the substituents are from 1 to 3 of halogen, $C_1$–$C_6$ alkyl, $C_1$–$C_6$ alkoxy, or hydroxy;

$R^{7a}$ and $R^{7b}$ are independently hydrogen, $C_1$–$C_3$ perfluoroalkyl, $C_1$–$C_6$ alkyl, substituted $C_1$–$C_6$ alkyl, where the substituents are phenyl or substituted phenyl; phenyl or substituted phenyl where the phenyl substituents are from 1 to 3 of halogen, $C_1$–$C_6$ alkyl, $C_1$–$C_6$ alkoxy, or hydroxy and v is 0 to 3;

$R^{3a}$ and $R^{3b}$ are independently hydrogen, $R^9$, $C_1$–$C_6$ alkyl substituted with $R^9$, phenyl substituted with $R^9$ or phenoxy substituted with $R^9$ with the proviso that either $R^{3a}$ and $R^{3b}$ must be a substituent other than hydrogen;

$R^9$ is $R^{4a}R^{12a}NSO_2(CH_2)_v$—, $R^{4a}R^{12a}NN(R^{12b})SO_2(CH_2)_v$—,
$R^{4a}R^{12a}NCON(R^{12b})SO_2(CH_2)_v$—,
$R^{4a}R^{12a}NCSN(R^{12b})SO_2(CH_2)_v$—,
$R^{4a}R^{12a}NN(R^{12b})CON(R^{12b})SO_2(CH_2)_v$—,
$R^{4a}R^{12a}NN(R^{12b})CSN(R^{12b})SO_2(CH_2)_v$—,
or $R^{13}OCON(R^{12b})SO_2(CH_2)_v$—, where v is 0 to 3;
$R^{12a}$, $R^{12b}$ and $R^{12c}$ are independently $R^{5a}$, $OR^{5a}$ or $COR^{5a}$. $R^{12a}$ and $R^{12b}$, or $R^{12b}$ and $R^{12c}$, or $R^{13}$ and $R^{12b}$, or $R^{12a}$ and $R^{4a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3 and $R^1$ and $R^{10}$ are as defined;

$R^{13}$ is $C_1-C_3$ perfluoroalkyl, $C_1-C_6$ alkyl, substituted $C_1-C_6$ alkyl, where the substitutents are hydroxy, —$NR^{10}R^{11}$, carboxy, phenyl or substituted phenyl; phenyl or substituted phenyl where the substituents on the phenyl are from 1 to 3 of halogen, $C_1-C_6$ alkyl, $C_1-C_6$ alkoxy or hydroxy where $R^{10}$ and $R^{11}$ are independently hydrogen, $C_1-C_6$ alkyl, phenyl, phenyl $C_1-C_6$ alkyl, $C_1-C_5$-alkoxycarbonyl or $C_1-C_5$alkanoyl-$C_1-C_6$ alkyl;

$R^4$, $R^{4a}$, $R^5$ and $R^{5a}$ are independently hydrogen, phenyl, substituted phenyl, $C_1-C_{10}$ alkyl, substituted $C_1-C_{10}$ alkyl, $C_3-C_{10}$ alkenyl, substituted $C_3-C_{10}$ alkenyl, $C_3-C_{10}$ alkynyl or substituted $C_3-C_{10}$ alkynyl where the substituents on the phenyl, alkyl, alkenyl or alkynyl are from 1 to 5 of hydroxy, $C_1-C_6$ alkoxy, $C_3-C_7$ cycloalkyl, fluoro, $R^1$, $R^2$ independently disubstituted phenyl, $R^1$, $R^2$ independently disubstituted phenyl $C_1-C_3$ alkoxy, $C_1-C_{20}$-alkanoyloxy, $C_1-C_5$ alkoxycarbonyl, carboxy, formyl or —$NR^{10}R^{11}$ where $R^1$, $R^2$, $R^{10}$ and $R^{11}$ are as defined above; or $R^4$ and $R^5$ can be taken together to form —$(CH_2)_r$—B—$(CH_2)_s$— where B is $CHR^1$, O, $S(O)_m$ or N—$R^{10}$, r and s are independently 1 to 3, m is 0, 1 or 2 and $R^1$ and $R^{10}$ are as defined above;

$R^6$ is hydrogen, $C_1-C_{10}$ alkyl, phenyl or phenyl $C_1-C_{10}$ alkyl;

A is

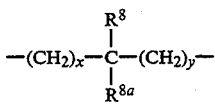

where x and y are independently 0-3;

$R^8$ and $R^{8a}$ are independently hydrogen, $C_1-C_{10}$ alkyl, trifluoromethyl, phenyl, substituted $C_1-C_{10}$ alkyl where the substitutents are from 1 to 3 of imidazolyl, indolyl, hydroxy, fluoro, —$S(O)_mR^{7a}$, $C_1-C_6$ alkoxy, $C_3-C_7$ cycloalkyl, $R^1$, $R^2$ independently disubstituted phenyl, $R^1$, $R^2$ independently disubstituted phenyl $C_1-C_3$ alkoxy, $C_1-C_5$ alkanoyloxy, $C_1-C_5$ alkoxycarbonyl, carboxy, formyl or —$NR^{10}R^{11}$ where $R^1$, $R^2$, $R^{7a}$, $R^{10}$, $R^{11}$ and m are as defined above; or $R^8$ and $R^{8a}$ can be taken together to form —$(CH_2)_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from one to five carbon atoms; and pharmaceutically acceptable salts thereof.

In the above structural formula and throughout the instant specification, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atoms fluorine, chlorine, bromine and iodine.

Certain of the above defined terms may occur more than once in the above formula and upon such occurrence each term shall be defined independently of the other.

Preferred compounds of the instant invention are realized when in the above structural formula:

n is 0 or 1;
p is 0 to 3;
q is 0 to 2;
w is 0 or 1;
X is O, $S(O)_m$,

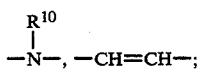

m is 0 to 2;
$R^1$, $R^2$, $R^{1a}$, $R^{2a}$, $R^{1b}$ and $R^{2b}$ are independently hydrogen, halogen, $C_1-C_7$ alkyl, $C_1-C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1-C_6$ alkyl, $C_1-C_6$ alkoxy, or hydroxy;

$R^{7a}$ and $R^{7b}$ are independently hydrogen, $C_1-C_3$ perfluoroalkyl, $C_1-C_6$ alkyl, substituted $C_1-C_6$ alkyl where the substitutents are phenyl; phenyl and v is 0 to 2;

$R^{3a}$ and $R^{3b}$ are independently hydrogen, $R^9$, $C_1-C_6$ alkyl substituted with $R^9$, phenyl substituted with $R^9$ or phenoxy substituted with $R^9$ with the proviso that either $R^{3a}$ and $R^{3b}$ must be a substituent other than hydrogen;

$R^9$ is
$R^{4a}R^{12a}NSO_2(CH_2)_v$—,
$R^{4a}R^{12a}NN(R^{12b})SO_2(CH_2)_v$—,
$R^{4a}R^{12a}NCON(R^{12b})SO_2(CH_2)_v$—,
$R^{4a}R^{12a}NN(R^{12b})CON(R^{12b})SO_2(CH_2)_v$—,
or $R^{13}OCON(R^{12b})SO_2(CH_2)_v$—, where v is 0 to 3;
$R^{12a}$, $R^{12b}$ and $R^{12c}$ are independently $R^{5a}$, $OR^{5a}$ or $COR^{5a}$. $R^{12a}$ and $R^{12b}$, or $R^{12b}$ and $R^{12c}$, or $R^{13}$ and $R^{12b}$, or $R^{12a}$ and $R^{4a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3 and $R^1$ and $R^{10}$ are as defined;

$R^{13}$ is $C_1-C_3$ perfluoroalkyl, $C_1-C_6$ alkyl, substituted $C_1-C_6$ alkyl, where the substitutents are hydroxy, —$NR^{10}R^{11}$, carboxy, phenyl or substituted phenyl; phenyl or substituted phenyl where the substituents on the phenyl are from 1 to 3 of halogen, $C_1-C_6$ alkyl, $C_1-C_6$ alkoxy or hydroxy where $R^{10}$ and $R^{11}$ are independently hydrogen, $C_1-C_6$ alkyl, phenyl, phenyl $C_1-C_6$ alkyl or $C_1-C_5$-alkanoyl-$C_1-C_6$ alkyl;

$R^4$, $R^{4a}$, $R^5$ and $R^{5a}$ are independently hydrogen, phenyl, substituted phenyl, $C_1-C_{10}$ alkyl, substituted $C_1-C_{10}$ alkyl where the substituents on the alkyl or phenyl are from 1 to 5 of hydroxy, $C_1-C_6$ alkoxy, $C_3-C_7$ cycloalkyl, fluoro, $R^1$, $R^2$ independently disubstituted phenyl, $R^1$, $R^2$ independently disubstituted phenyl $C_1$–$C_3$ alkoxy, $C_1$–$C_{20}$-alkanoyloxy, $C_1$–$C_5$ alkoxycarbonyl, carboxy or formyl; $R^4$ and $R^5$ can be taken together to form —$(CH_2)_r$—B—$(CH_2)_s$— where B is $CHR^1$, O, $S(O)_m$ or N—$R^{10}$, r and s are independently 1 to 3, m is 0, 1 or 2 and $R^1$ and $R^{10}$ are as defined above; $R^6$ is hydrogen, $C_1$–$C_{10}$ alkyl or phenyl $C_1$–$C_{10}$ alkyl;

A is

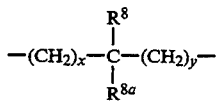

where x and y are independently 0–2;
$R^8$ and $R^{8a}$ are independently hydrogen, $C_1$–$C_{10}$ alkyl, substituted $C_1$–$C_{10}$ alkyl where the substituents are from 1 to 3 of imidazolyl, indolyl, hydroxy, fluoro, —$S(O)_m R^{7a}$, $C_1$–$C_6$ alkoxy, $R^1$, $R^2$ independently disubstituted phenyl, $C_1$–$C_5$ alkanoyloxy, $C_1$–$C_5$ alkoxycarbonyl, carboxy, formyl or —$NR^{10}R^{11}$ where $R^1$, $R^2$, $R^{7a}$, $R^{10}$, $R^{11}$ and m are as defined above; or $R^8$ and $R^{8a}$ can be taken together to form —$(CH_2)_t$— where t is 2 to 4; and $R^8$ and $R^{8a}$ can independently be joined to one or both of $R^4$ and $R^5$ to form alkylene bridges between the terminal nitrogen and the alkyl portion of the A group wherein the bridge contains from one to five carbon atoms;
and pharmaceutically acceptable salts thereof.

Additional preferred compounds are realized in the above structural formula when:
n is 0 or 1;
p is 0 to 2;
q is 0 to 2;
w is 0 or 1;
X is $S(O)_m$ or —CH=CH—;
m is 0 to 1;
$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, —$S(O)_m R^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$–$C_6$ alkyl, $C_1$–$C_6$ alkoxy, or hydroxy;
$R^{7a}$ and $R^{7b}$ are independently hydrogen, $C_1$–$C_6$ alkyl or substituted $C_1$–$C_6$ alkyl where the substituents are phenyl and v is 0 to 2;
$R^{3a}$ and $R^{3b}$ are independently hydrogen, $R^9$, $C_1$–$C_6$ alkyl substituted with $R^9$ or phenoxy substituted with $R^9$ with the proviso that either $R^{3a}$ and $R^{3b}$ must be a substituent other than hydrogen;
$R^9$ is
$R^{4a}R^{12a}NSO_2(CH_2)_v$—,
$R^{4a}R^{12a}NN(R^{12b})SO_2(CH_2)_v$—,
$R^{4a}R^{12a}NCON(R^{12b})SO_2(CH_2)_v$—,
or $R^{13}OCON(R^{12b})SO_2(CH_2)_v$—, where v is 0 to 2;
$R^{12a}$, $R^{12b}$ and $R^{12c}$ are independently $R^{5a}$ or $COR^{5a}$. $R^{12a}$ and $R^{12b}$, or $R^{12b}$ and $R^{12c}$, or $R^{13}$ and $R^{12b}$, or $R^{12a}$ and $R^{4a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2 and $R^1$ and $R^{10}$ are as defined;
$R^{13}$ is $C_1$–$C_6$ alkyl, substituted $C_1$–$C_6$ alkyl, where the substituents are phenyl or substituted phenyl; phenyl or substituted phenyl where the substituents on the phenyl are from 1 to 3 of halogen, $C_1$–$C_6$ alkyl, $C_1$–$C_6$ alkoxy or hydroxy;
$R^4$, $R^{4a}$, $R^5$ and $R^{5a}$ are independently hydrogen, $C_1$–$C_{10}$ alkyl or substituted $C_1$–$C_{10}$ alkyl where the substituents are from 1 to 5 of hydroxy, $C_1$–$C_6$ alkoxy, fluoro, $R^1$, $R^2$ independently disubstituted phenyl, $C_1$–$C_{20}$-alkanoyloxy, $C_1$–$C_5$ alkoxycarbonyl or carboxy; where $R^1$ and $R^2$ are as defined above;
$R^6$ is hydrogen or $C_1$–$C_{10}$ alkyl;
A is

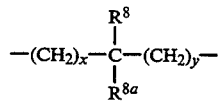

where x and y are independently 0–2;
$R^8$ and $R^{8a}$ are independently hydrogen, $C_1$–$C_{10}$ alkyl, substituted $C_1$–$C_{10}$ alkyl where the substituents are from 1 to 3 of imidazolyl, indolyl, hydroxy, fluoro, —$S(O)_m R^{7a}$, $C_1$–$C_6$ alkoxy, $R^1$, $R^2$ independently disubstituted phenyl, $C_1$–$C_5$ alkanoyloxy, $C_1$–$C_5$ alkoxycarbonyl or carboxy where $R^1$, $R^2$, $R^{7a}$ and m are as defined above; or $R^8$ and $R^{8a}$ can be taken together to form —$(CH_2)_t$— where t is 2; and $R^8$ and $R^{8a}$ can independently be joined to one or both of $R^4$ and $R^5$ to form alkylene bridges between the terminal nitrogen and the alkyl portion of the A group wherein the bridge contains from one to five carbon atoms;
and pharmaceutically acceptable salts thereof.

Still further preferred compounds of the instant invention are realized in the above structural formula when;
n is 0 or 1;
p is 0 to 2;
q is 1;
w is 1;
X is $S(O)_m$ or —CH=CH—;
m is 0 to 1;
$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, —$S(O)_m R^{7a}$, $R^{7b}O(CH_2)_v$—, $R^{7b}COO(CH_2)_v$—, phenyl or substituted phenyl where the substituents are from 1 to 3 of halogen, $C_1$–$C_6$ alkyl, $C_1$–$C_6$ alkoxy, or hydroxy;
$R^{7a}$ and $R^{7b}$ are independently hydrogen, $C_1$–$C_6$ alkyl or substituted $C_1$–$C_6$ alkyl where the substituents are phenyl and v is 0 or 1;
$R^{3a}$ and $R^{3b}$ are independently hydrogen, $R^9$ or $C_1$–$C_6$ alkyl substituted with $R^9$, with the proviso that either $R^{3a}$ and $R^{3b}$ must be a substituent other than hydrogen;
$R^9$ is
$R^{4a}R^{12a}NSO_2(CH_2)_v$—,
$R^{4a}R^{12a}NCON(R^{12b})SO_2(CH_2)_v$—,
or $R^{13}OCON(R^{12b})SO_2(CH_2)_v$— where v is 0 or 1;
$R^{12a}$, $R^{12b}$ and $R^{12c}$ are independently $R^{5a}$ or $COR^{5a}$. $R^{12a}$ and $R^{12b}$, or $R^{12b}$ and $R^{12c}$, or $R^{13}$ and $R^{12b}$, or $R^{12a}$ and $R^{4a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2 and $R^1$ and $R^{10}$ are as defined;
$R^{13}$ is $C_1$–$C_6$ alkyl, substituted $C_1$–$C_6$ alkyl, where the substituents are phenyl or substituted phenyl; phenyl or substituted phenyl where the substituents on the phenyl are from 1 to 3 of halogen, $C_1$–$C_6$ alkyl, $C_1$–$C_6$ alkoxy or hydroxy;
$R^4$, $R^{4a}$, $R^5$ and $R^{5a}$ are independently hydrogen, $C_1$–$C_{10}$ alkyl or substituted $C_1$–$C_{10}$ alkyl where the substituents are from 1 to 3 of hydroxy, $C_1$–$C_3$ alkoxy, fluoro, $R^1$, $R^2$ independently disubstituted phenyl, $C_1$–$C_{20}$-alkanoyloxy, $C_1$–$C_5$ alkoxycarbonyl or carboxy; where $R^1$ and $R^2$ are as defined above;
$R^6$ is hydrogen;

A is

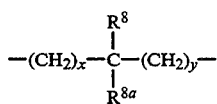

where x and y are independently 0 or 1;
$R^8$ and $R^{8a}$ are independently hydrogen, $C_1$–$C_{10}$ alkyl, substituted $C_1$–$C_{10}$ alkyl where the substitutents are from 1 to 3 of imidazolyl, indolyl, hydroxy, fluoro, —$S(O)_m R^{7a}$, $C_1$–$C_6$ alkoxy, $R^1$, $R^2$ independently disubstituted phenyl, $C_1$–$C_5$ alkanoyloxy, $C_1$–$C_5$ alkoxycarbonyl or carboxy where $R^1$, $R^2$, $R^{7a}$ and m are as defined above; or $R^8$ and $R^{8a}$ can be taken together to form —$(CH_2)_t$— where t is 2; and $R^8$ and $R^{8a}$ can independently be joined to one or both of $R^4$ and $R^5$ to form alkylene bridges between the terminal nitrogen and the alkyl portion of the A group wherein the bridge contains from one to five carbon atoms;
and pharmaceutically acceptable salts thereof.

Representative preferred growth hormone releasing compounds of the present invention include the following:

1. 3-Amino-3-methyl-N-[1-[[2'-(benzamido)sulfonyl[1,1'-biphenyl]-4-yl]methyl]-2,3,4,5-tetrahydro-2-oxo-1H-1-benzazepin-3(R)-yl]butanamide;
2. 3-Amino-3-methyl-N-[1-[[2'-(benzamido)sulfonyl[1,1'-biphenyl]-4-yl]methyl]-7-fluoro-2,3,4,5-tetrahydro-2-oxo-1H-1-benzazepin-3(R)-yl]butanamide;
3. 3-Amino-3-methyl-N-[1-[[2'-(benzamido)sulfonyl[1,1'-biphenyl]-4-yl]methyl]-7-trifluoromethyl-2,3,4,5-tetrahydro-2-oxo-1H-1-benzazepin-3(R)-yl]butanamide;
4. 3-Amino-3-methyl-N-[1-[[2'-(benzamido)sulfonyl[1,1'-biphenyl]-4-yl]methyl]-7-methylthio-2,3,4,5-tetrahydro-2-oxo-1H-1-benzazepin-3(R)-yl]butanamide;
5. 3-Amino-3-methyl-N-[1-[[2'-(benzamido)sulfonyl[1,1'-biphenyl]-4-yl]methyl]-7-methoxy-2,3,4,5-tetrahydro-2-oxo-1H-1-benzazepin-3(R)-yl]butanamide;
6. 2-Amino-2-methyl-N-[1-[[2'-(benzamido)sulfonyl[1,1'-biphenyl]-4-yl]methyl]-2,3,4,5-tetrahydro-2-oxo-1H-1-benzazepin-3(R)-yl]propanamide;
7. 2-Amino-2-methyl-N-[1-[[2'-(benzamido)sulfonyl[1,1'-biphenyl]-4-yl]methyl]-7-fluoro-2,3,4,5-tetrahydro-2-oxo-1H-1-benzazepin-3(R)-yl]propanamide;
8. 2-Amino-2-methyl-N-[1-[[2'-(benzamido)sulfonyl[1,1'-biphenyl]-4-yl]methyl]-7-trifluoromethyl-2,3,4,5-tetrahydro-2-oxo-1H-1-benzazepin-3(R)-yl]propanamide;
9. 2-Amino-2-methyl-N-[1-[[2'-(benzamido)sulfonyl[1,1'-biphenyl]-4-yl]methyl]-7-methylthio-2,3,4,5-tetrahydro-2-oxo-1H-1-benzazepin-3(R)-yl]propanamide;
10. 2-Amino-2-methyl-N-[1-[[2'-(benzamido)sulfonyl[1,1'-biphenyl]-4-yl]methyl]-7-methoxy-2,3,4,5-tetrahydro-2-oxo-1H-1-benzazepin-3(R)-yl]propanamide;
11. 3-[2(R)-Hydroxypropyl]amino-3-methyl-N-[1-[[2'-(benzamido)sulfonyl[1,1'-biphenyl]-4-yl]methyl]-2,3,4,5-tetrahydro-2-oxo-1H-1-benzazepin-3(R)-yl]butanamide;
12. 3-[2(R)-Hydroxypropyl]amino-3-methyl-N-[1-[[2'-(benzamido)sulfonyl[1,1'-biphenyl]-4-yl]methyl]-7-fluoro-2,3,4,5-tetrahydro-2-oxo-1H-1-benzazepin-3(R)-yl]butanamide;
13. 3-[2(R)-Hydroxypropyl]amino-3-methyl-N-[1-[[2'-(benzamido)sulfonyl[1,1'-biphenyl]-4-yl]methyl]-7-trifluoromethyl-2,3,4,5-tetrahydro-2-oxo-1H-1-benzazepin-3(R)-yl]butanamide;
14. 3-[2(R)-Hydroxypropyl]amino-3-methyl-N-[1-[[2'-(benzamido)sulfonyl[1,1'-biphenyl]-4-yl]methyl]-7-methylthio-2,3,4,5-tetrahydro-2-oxo-1H-1-benzazepin-3(R)-yl]butanamide;
15. 3-[2(R)-Hydroxypropyl]amino-3-methyl-N-[1-[[2'-(benzamido)sulfonyl[1,1'-biphenyl]-4-yl]methyl]-7-methoxy-2,3,4,5-tetrahydro-2-oxo-1H-1-benzazepin-3(R)-yl]butanamide;
16. 3-[2(S),3-Dihydroxypropyl]amino-3-methyl-N-[1-[[2'-(benzamido)sulfonyl[1,1'-biphenyl]-4-yl]methyl]-2,3,4,5-tetrahydro-2-oxo-1H-1-benzazepin-3(R)-yl]butanamide;
17. 3-[2(S),3-Dihydroxypropyl]amino-3-methyl-N-[1-[[2'-(benzamido)sulfonyl[1,1'-biphenyl]-4-yl]methyl]-7-fluoro-2,3,4,5-tetrahydro-2-oxo-1H-1-benzazepin-3(R)-yl]butanamide;
18. 3-[2(S),3-Dihydroxypropyl]amino-3-methyl-N-[1-[[2'-(benzamido)sulfonyl[1,1'-biphenyl]-4-yl]methyl]-7-trifluoromethyl-2,3,4,5-tetrahydro-2-oxo-1H-1-benzazepin-3(R)-yl]butanamide;
19. 3-[2(S),3-Dihydroxypropyl]amino-3-methyl-N-[1-[[2'-(benzamido)sulfonyl[1,1'-biphenyl]-4-yl]methyl]-7-methylthio-2,3,4,5-tetrahydro-2-oxo-1H-1-benzazepin-3(R)-yl]butanamide;
20. 3-[2(S),3-Dihydroxypropyl]amino-3-methyl-N-[1-[[2'-(benzamido)sulfonyl[1,1'-biphenyl]-4-yl]methyl]-7-methoxy-2,3,4,5-tetrahydro-2-oxo-1H-1-benzazepin-3(R)-yl]butanamide;
21. 3-Amino-3-methyl-N-[1-[[2'-(ethylamino)sulfonyl[1,1'-biphenyl]-4-yl]methyl]-2,3,4,5-tetrahydro-2-oxo-1H-1-benzazepin-3(R)-yl]butanamide;
22. 3-Amino-3-methyl-N-[1-[[2'-(ethylamino)sulfonyl[1,1'-biphenyl]-4-yl]methyl]-7-fluoro-2,3,4,5-tetrahydro-2-oxo-1H-1-benzazepin-3(R)-yl]butanamide;
23. 3-Amino-3-methyl-N-[1-[[2'-(ethylamino)sulfonyl[1,1'-biphenyl]-4-yl]methyl]-7-trifluoromethyl-2,3,4,5-tetrahydro-2-oxo-1H-1-benzazepin-3(R)-yl]butanamide;
24. 3-Amino-3-methyl-N-[1-[[2'-(ethylamino)sulfonyl[1,1'-biphenyl]-4-yl]methyl]-7-methylthio-2,3,4,5-tetrahydro-2-oxo-1H-1-benzazepin-3(R)-yl]butanamide;
25. 3-Amino-3-methyl-N-[1-[[2'-(ethylamino)sulfonyl[1,1'-biphenyl]-4-yl]methyl]-7-methoxy-2,3,4,5-tetrahydro-2-oxo-1H-1-benzazepin-3(R)-yl]butanamide;
26. 2-Amino-2-methyl-N-[1-[[2'-(ethylamino)sulfonyl[1,1'-biphenyl]-4-yl]methyl]-2,3,4,5-tetrahydro-2-oxo-1H-1-benzazepin-3(R)-yl]propanamide;
27. 2-Amino-2-methyl-N-[1-[[2'-(ethylamino)sulfonyl[1,1'-biphenyl]-4-yl]methyl]-7-fluoro-2,3,4,5-tetrahydro-2-oxo-1H-1-benzazepin-3(R)-yl]propanamide;
28. 2-Amino-2-methyl-N-[1-[[2'-(ethylamino)sulfonyl[1,1'-biphenyl]-4-yl]methyl]-7-trifluoromethyl-2,3,4,5-tetrahydro-2-oxo-1H-1-benzazepin-3(R)-yl]propanamide;
29. 2-Amino-2-methyl-N-[1-[[2'-(ethylamino)sulfonyl[1,1'-biphenyl]-4-yl]methyl]-7-methylthio-2,3,4,5-tetrahydro-2-oxo-1H-1-benzazepin-3(R)-yl]propanamide;

30. 2-Amino-2-methyl-N-[1-[[2'-(ethylamino)sulfonyl[1,1'-biphenyl]-4-yl]methyl]-7-methoxy-2,3,4,5-tetrahydro-2-oxo-1H-1-benzazepin-3(R)-yl]propanamide;

31. 3-[2(R)-Hydroxypropyl]amino-3-methyl-N-[1-[[2'-(ethylamino)sulfonyl[1,1'-biphenyl]-4-yl]methyl]-2,3,4,5-tetrahydro-2-oxo-1H-1-benzazepin-3(R)-yl]butanamide;

32. 3-[2(R)-Hydroxypropyl]amino-3-methyl-N-[1-[[2'-(ethylamino)sulfonyl[1,1'-biphenyl]-4-yl]methyl]-7-fluoro-2,3,4,5-tetrahydro-2-oxo-1H-1-benzazepin-3(R)-yl]butanamide;

33. 3-[2(R)-Hydroxypropyl]amino-3-methyl-N-[1-[[2'-(ethylamino)sulfonyl[1,1'-biphenyl]-4-yl]methyl]-7-trifluoromethyl-2,3,4,5-tetrahydro-2-oxo-1H-1-benzazepin-3(R)-yl]butanamide;

34. 3-[2(R)-Hydroxypropyl]amino-3-methyl-N-[1-[[2'-(ethylamino)sulfonyl[1,1'-biphenyl]-4-yl]methyl]-7-methylthio-2,3,4,5-tetrahydro-2-oxo-1H-1-benzazepin-3(R)-yl]butanamide;

35. 3-[2(R)-Hydroxypropyl]amino-3-methyl-N-[1-[[2'-(ethylamino)sulfonyl[1,1'-biphenyl]-4-yl]methyl]-7-methoxy-2,3,4,5-tetrahydro-2-oxo-1H-1-benzazepin-3(R)-yl]butanamide;

36. 3-[2(S),3-Dihydroxypropyl]amino-3-methyl-N-[1-[[2'-(ethylamino)sulfonyl[1,1'-biphenyl]-4-yl]methyl]-2,3,4,5-tetrahydro-2oxo-1H-1-benzazepin-3(R)-yl]butanamide;

37. 3-[2(S),3-Dihydroxypropyl]amino-3-methyl-N-[1-[[2'-(ethylamino)sulfonyl[1,1'-biphenyl]-4-yl]methyl]-7-fluoro-2,3,4,5-tetrahydro-2-oxo-1H-1-benzazepin-3(R)-yl]butanamide;

38. 3-[2(S),3-Dihydroxypropyl]amino-3-methyl-N-[1-[[2'-(ethylamino)sulfonyl[1,1'-biphenyl]-4-yl]methyl]-7-trifluoromethyl-2,3,4,5-tetrahydro-2-oxo-1H-1-benzazepin-3(R)-yl]butanamide;

39. 3-[2(S),3-Dihydroxypropyl]amino-3-methyl-N-[1-[[2'-(ethylamino)sulfonyl[1,1'-biphenyl]-4-yl]methyl]-7-methylthio-2,3,4,5-tetrahydro-2-oxo-1H-1-benzazepin-3(R)-yl]butanamide;

40. 3-[2(S),3-Dihydroxypropyl]amino-3-methyl-N-[1-[[2'-(ethylamino)sulfonyl[1,1'-biphenyl]-4-yl]methyl]-7-methoxy-2,3,4,5-tetrahydro-2-oxo-1H-1-benzazepin-3(R)-yl]butanamide;

41. 3-Amino-3-methyl-N-[1-[[2'-(aminosulfonyl)[1,1'-biphenyl]-4-yl]methyl]-2,3,4,5-tetrahydro-2-oxo-1H-1-benzazepin-3(R)-yl]butanamide;

42. 3-Amino-3-methyl-N-[1-[[2'-(aminosulfonyl)[1,1'-biphenyl]-4-yl]methyl]-7-fluoro-2,3,4,5-tetrahydro-2-oxo-1H-1-benzazepin-3(R)-yl]butanamide;

43. 3-Amino-3-methyl-N-[1-[[2'-(aminosulfonyl)[1,1'-biphenyl]-4-yl]methyl]-7-trifluoromethyl-2,3,4,5-tetrahydro-2-oxo-1H-1-benzazepin-3(R)-yl]butanamide;

44. 3-Amino-3-methyl-N-[1-[[2'-(aminosulfonyl)[1,1'-biphenyl]-4-yl]methyl]-7-methylthio-2,3,4,5-tetrahydro-2-oxo-1H-1-benzazepin-3(R)-yl]butanamide;

45. 3-Amino-3-methyl-N-[1-[[2'-(aminosulfonyl)[1,1'-biphenyl]-4-yl]methyl]-7-methoxy-2,3,4,5-tetrahydro-2-oxo-1H-1-benzazepin-3(R)-yl]butanamide;

46. 2-Amino-2-methyl-N-[1-[[2'-(aminosulfonyl)[1,1'-biphenyl]-4-yl]methyl]-2,3,4,5-tetrahydro-2-oxo-1H-1-benzazepin-3(R)-yl]propanamide;

47. 2-Amino-2-methyl-N-[1-[[2'-(aminosulfonyl)[1,1'-biphenyl]-4-yl]methyl]-7-fluoro-2,3,4,5-tetrahydro-2-oxo-1H-1-benzazepin-3(R)-yl]propanamide;

48. 2-Amino-2-methyl-N-[1-[[2'-(aminosulfonyl)[1,1'-biphenyl]-4-yl]methyl]-7-trifluoromethyl-2,3,4,5-tetrahydro-2-oxo-1H-1-benzazepin-3(R)-yl]propanamide;

49. 2-Amino-2-methyl-N-[1-[[2'-(aminosulfonyl)[1,1'-biphenyl]-4-yl]methyl]-7-methylthio-2,3,4,5-tetrahydro-2-oxo-1H-1-benzazepin-3(R)-yl]propanamide;

50. 2-Amino-2-methyl-N-[1-[[2'-(aminosulfonyl)[1,1'-biphenyl]-4-yl]methyl]-7-methoxy-2,3,4,5-tetrahydro-2-oxo-1H-1-benzazepin-3(R)-yl]propanamide;

51. 3-[2(R)-Hydroxypropyl]amino-3-methyl-N-[1-[[2'-(aminosulfonyl)[1,1'-biphenyl]-4-yl]methyl]-2,3,4,5-tetrahydro-2-oxo-1H-1-benzazepin-3(R)-yl]butanamide;

52. 3-[2(R)-Hydroxypropyl]amino-3-methyl-N-[1-[[2'-(aminosulfonyl)[1,1'-biphenyl]-4-yl]methyl]-7-fluoro-2,3,4,5-tetrahydro-2-oxo-1H-1-benzazepin-3(R)-yl]butanamide;

53. 3-[2(R)-Hydroxypropyl]amino-3-methyl-N-[1-[[2'-(aminosulfonyl)[1,1'-biphenyl]-4-yl]methyl]-7-trifluoromethyl-2,3,4,5-tetrahydro-2-oxo-1H-1-benzazepin-3(R)-yl]butanamide;

54. 3-[2(R)-Hydroxypropyl]amino-3-methyl-N-[1-[[2'-(aminosulfonyl)[1,1'-biphenyl]-4-yl]methyl]-7-methylthio-2,3,4,5-tetrahydro-2-oxo-1H-1-benzazepin-3(R)-yl]butanamide;

55. 3-[2(R)-Hydroxypropyl]amino-3-methyl-N-[1-[[2'-(aminosulfonyl)[1,1'-biphenyl]-4-yl]methyl]-7-methoxy-2,3,4,5-tetrahydro-2-oxo-1H-1-benzazepin-3(R)-yl]butanamide;

56. 3-[2(S),3-Dihydroxypropyl]amino-3-methyl-N-[1-[[2'-(aminosulfonyl)[1,1'-biphenyl]-4-yl]methyl]-2,3,4,5-tetrahydro-2-oxo-1H-1-benzazepin-3(R)-yl]butanamide;

57. 3-[2(S),3-Dihydroxypropyl]amino-3-methyl-N-[1-[[2'-(aminosulfonyl)[1,1'-biphenyl]-4-yl]methyl]-7-fluoro-2,3,4,5-tetrahydro-2-oxo-1H-1-benzazepin-3(R)-yl]butanamide;

58. 3-[2(S),3-Dihydroxypropyl]amino-3-methyl-N-[1-[[2'-(aminosulfonyl)[1,1'-biphenyl]-4-yl]methyl]-7-trifluoromethyl-2,3,4,5-tetrahydro-2-oxo-1H-1-benzazepin-3(R)-yl]butanamide;

59. 3-[2(S),3-Dihydroxypropyl]amino-3-methyl-N-[1-[[2'-(aminosulfonyl)[1,1'-biphenyl]-4-yl]methyl]-7-methylthio-2,3,4,5-tetrahydro-2-oxo-1H-1-benzazepin-3(R)-yl]butanamide;

60. 3-[2(S),3-Dihydroxypropyl]amino-3-methyl-N-[1-[[2'-(aminosulfonyl)[1,1'-biphenyl]-4-yl]methyl]-7-methoxy-2,3,4,5-tetrahydro-2-oxo-1H-1-benzazepin-3(R)-yl]butanamide;

61. 3-Amino-3-methyl-N-[1-[[2'-(t-butylamino)sulfonyl[1,1'-biphenyl]-4-yl]methyl]-2,3,4,5-tetrahydro-2-oxo-1H-1-benzazepin-3(R)-yl]butanamide;

62. 3-Amino-3-methyl-N-[1-[[2'-(t-butylamino)sulfonyl[1,1'-biphenyl]-4-yl]methyl]-7-fluoro-2,3,4,5-tetrahydro-2-oxo-1H-1-benzazepin-3(R)-yl]butanamide;

63. 3-Amino-3-methyl-N-[1-[[2'-(t-butylamino)sulfonyl[1,1'-biphenyl]-4-yl]methyl]-7-trifluoromethyl-2,3,4,5-tetrahydro-2-oxo-1H-1-benzazepin-3(R)-yl]butanamide;

64. 3-Amino-3-methyl-N-[1-[[2'-(t-butylamino)sulfonyl[1,1'-biphenyl]-4-yl]methyl]-7-methylthio-2,3,4,5-tetrahydro-2-oxo-1H-1-benzazepin-3(R)-yl]butanamide;

65. 3-Amino-3-methyl-N-[1-[[2'-(t-butylamino)sulfonyl[1,1'-biphenyl]-4-yl]methyl]-7-methoxy-2,3,4,5-tetrahydro-2-oxo-1H-1-benzazepin-3(R)-yl]butanamide;

66. 2-Amino-2-methyl-N-[1-[[2'-(t-butylamino)sulfonyl[1,1'-biphenyl]-4-yl]methyl]-2,3,4,5-tetrahydro-2-oxo-1H-1-benzazepin-3(R)-yl]propanamide;

67. 2-Amino-2-methyl-N-[1-[[2'-(t-butylamino)sulfonyl[1,1'-biphenyl]-4-yl]methyl]-7-fluoro-2,3,4,5-tetrahydro-2-oxo-1H-1-benzazepin-3(R)-yl]propanamide;

68. 2-Amino-2-methyl-N-[1-[[2'-(t-butylamino)sulfonyl[1,1'-biphenyl]-4-yl]methyl]-7-trifluoromethyl-2,3,4,5-tetrahydro-2-oxo-1H-1-benzazepin-3(R)-yl]propanamide;

69. 2-Amino-2-methyl-N-[1-[[2'-(t-butylamino)sulfonyl[1,1'-biphenyl]-4-yl]methyl]-7-methylthio-2,3,4,5-tetrahydro-2-oxo-1H-1-benzazepin-3(R)-yl]propanamide;

70. 2-Amino-2-methyl-N-[1-[[2'-(t-butylamino)sulfonyl[1,1'-biphenyl]-4-yl]methyl]-7-methoxy-2,3,4,5-tetrahydro-2-oxo-1H-1-benzazepin-3(R)-yl]propanamide;

71. 3-[2(R)-Hydroxypropyl]amino-3-methyl-N-[1-[[2'-(t-butylamino)sulfonyl[1,1'-biphenyl]-4-yl]methyl]-2,3,4,5-tetrahydro-2-oxo-1H-1-benzazepin-3(R)-yl]butanamide;

72. 3-[2(R)-Hydroxypropyl]amino-3-methyl-N-[1-[[2'-(t-butylamino)sulfonyl[1,1'-biphenyl]-4-yl]methyl]-7-fluoro-2,3,4,5-tetrahydro-2oxo-1H-1-benzazepin-3(R)-yl]butanamide;

73. 3-[2(R)-Hydroxypropyl]amino-3-methyl-N-[1-[[2'-(t-butylamino)sulfonyl[1,1'-biphenyl]-4-yl]methyl]-7-trifluoromethyl-2,3,4,5-tetrahydro-2-oxo-1H-1-benzazepin-3(R)-yl]butanamide;

74. 3-[2(R)-Hydroxypropyl]amino-3-methyl-N-[1-[[2'-(t-butylamino)sulfonyl[1,1'-biphenyl]-4-yl]methyl]-7-methylthio-2,3,4,5-tetrahydro-2-oxo-1H-1-benzazepin-3(R)-yl]butanamide;

75. 3-[2(R)-Hydroxypropyl]amino-3-methyl-N-[1-[[2'-(t-butylamino)sulfonyl[1,1'-biphenyl]-4-yl]methyl]-7-methoxy-2,3,4,5-tetrahydro-2-oxo-1H-1-benzazepin-3(R)-yl]butanamide;

76. 3-[2(S),3-Dihydroxypropyl]amino-3-methyl-N-[1-[[2'-(t-butylamino)sulfonyl[1,1'-biphenyl]-4-yl]methyl]-2,3,4,5-tetrahydro-2-oxo-1H-1-benzazepin-3(R)-yl]butanamide;

77. 3-[2(S),3-Dihydroxypropyl]amino-3-methyl-N-[1-[[2'-(t-butylamino)sulfonyl[1,1'-biphenyl]-4-yl]methyl]-7-fluoro-2,3,4,5-tetrahydro-2-oxo-1H-1-benzazepin-3(R)-yl]butanamide;

78. 3-[2(S),3-Dihydroxypropyl]amino-3-methyl-N-[1-[[2'-(t-butylamino)sulfonyl[1,1'-biphenyl]-4-yl]methyl]-7-trifluoromethyl-2,3,4,5-tetrahydro-2-oxo-1H-1-benzazepin-3(R)-yl]butanamide;

79. 3-[2(S),3-Dihydroxypropyl]amino-3-methyl-N-[1-[[2'-(t-butylamino)sulfonyl[1,1'-biphenyl]-4-yl]methyl]-7-methylthio-2,3,4,5-tetrahydro-2-oxo-1H-1-benzazepin-3(R)-yl]butanamide;

80. 3-[2(S),3-Dihydroxypropyl]amino-3-methyl-N-[1-[[2'-(t-butylamino)sulfonyl[1,1'-biphenyl]-4-yl]methyl]-7-methoxy-2,3,4,5-tetrahydro-2-oxo-1H-1-benzazepin-3(R)-yl]butanamide;

81. 3-Amino-3-methyl-N-[5-[[2'-(benzamido)sulfonyl[1,1'-biphenyl]-4-yl]methyl]-2,3,4,5-tetrahydro-4-oxo-1,5-benzothiazepin-3(S)-yl]butanamide;

82. 3-Amino-3-methyl-N-[5-[[2'-(benzamido)sulfonyl[1,1'-biphenyl]-4-yl]methyl]-8-fluoro-2,3,4,5-tetrahydro-4-oxo-1,5-benzothiazepin-3(S)-yl]butanamide;

83. 3-Amino-3-methyl-N-[5-[[2'-(benzamido)sulfonyl[1,1'-biphenyl]-4-yl]methyl-8-trifluoromethyl-2,3,4,5-tetrahydro-4-oxo-1,5-benzothiazepin-3(S)-yl]butanamide;

84. 3-Amino-3-methyl-N-[5-[[2'-(benzamido)sulfonyl[1,1'-biphenyl]-4-yl]methyl-8-methylthio-2,3,4,5-tetrahydro-4-oxo-1,5-benzothiazepin-3(S)-yl]butanamide;

85. 3-Amino-3-methyl-N-[5-[[2'-(benzamido)sulfonyl[1,1'-biphenyl]-4-yl]methyl-8-methoxy-2,3,4,5-tetrahydro-4-oxo-1,5-benzothiazepin-3(S)-yl]butanamide;

86. 2-Amino-2-methyl-N-[5-[[2'-(benzamido)sulfonyl[1,1'-biphenyl]-4-yl]methyl]-2,3,4,5-tetrahydro-4-oxo-1,5-benzothiazepin-3(S)-yl]propanamide;

87. 2-Amino-2-methyl-N-[5-[[2'-(benzamido)sulfonyl[1,1'-biphenyl]-4-yl]methyl]-8-fluoro-2,3,4,5-tetrahydro-4-oxo-1,5-benzothiazepin-3(S)-yl]propanamide;

88. 2-Amino-2-methyl-N-[5-[[2'-(benzamido)sulfonyl[1,1'-biphenyl]-4-yl]methyl]-8-trifluoromethyl-2,3,4,5-tetrahydro-4-oxo-1,5-benzothiazepin-3(S)-yl]propanamide;

89. 2-Amino-2-methyl-N-[5-[[2'-(benzamido)sulfonyl[1,1'-biphenyl]-4-yl]methyl]-8-methylthio-2,3,4,5-tetrahydro-4-oxo-1,5-benzothiazepin-3(S)-yl]propanamide;

90. 2-Amino-2-methyl-N-[5-[[2'-(benzamido)sulfonyl[1,1'-biphenyl]-4-yl]methyl]-8-methoxy-2,3,4,5-tetrahydro-4-oxo-1,5-benzothiazepin-3(S)-yl]propanamide;

91. 3-[2(R)-Hydroxypropyl]amino-3-methyl-N-[5-[[2'-(benzamido)sulfonyl[1,1'-biphenyl]-4-yl]methyl]-2,3,4,5-tetrahydro-4-oxo-1,5-benzothiazepin-3(S)-yl]butanamide;

92. 3-[2(R)-Hydroxypropyl]amino-3-methyl-N-[5-[[2'-(benzamido)sulfonyl[1,1'-biphenyl]-4-yl]methyl-8-fluoro-2,3,4,5-tetrahydro-4-oxo-1,5-benzothiazepin-3(S)-yl]butanamide;

93. 3-[2(R)-Hydroxypropyl]amino-3-methyl-N-[5-[[2'-(benzamido)sulfonyl[1,1'-biphenyl]-4-yl]methyl-8-trifluoromethyl-2,3,4,5-tetrahydro-4-oxo-1,5-benzothiazepin-3(S)-yl]butanamide;

94. 3-[2(R)-Hydroxypropyl]amino-3-methyl-N-[5-[[2'-(benzamido)sulfonyl[1,1'-biphenyl]-4-yl]methyl-8-methylthio-2,3,4,5-tetrahydro-4-oxo -1,5-benzothiazepin-3(S)-yl]butanamide;

95. 3-[2(R)-Hydroxypropyl]amino-3-methyl-N-[5-[[2'-(benzamido)sulfonyl[1,1'-biphenyl]-4-yl]methyl-8-methoxy-2,3,4,5-tetrahydro-4-oxo-1,5-benzothiazepin-3(S)-yl]butanamide;

96. 3-[2(S),3-Dihydroxypropyl]amino-3-methyl-N-[5-[[2'-(benzamido)sulfonyl[1,1'-biphenyl]-4-yl]methyl]-2,3,4,5-tetrahydro-4-oxo-1,5-benzothiazepin-3(S)-yl]butanamide;

97. 3-[2(S),3-Dihydroxypropyl]amino-3-methyl-N-[5-[[2'-(benzamido)sulfonyl[1,1'-biphenyl]-4-yl]methyl-8-fluoro-2,3,4,5-tetrahydro-4-oxo-1,5-benzothiazepin-3(S)-yl]butanamide;

98. 3-[2(S),3-Dihydroxypropyl]amino-3-methyl-N-[5-[[2'-(benzamido)sulfonyl[1,1'-biphenyl]-4-yl]methyl-8-trifluoromethyl-2,3,4,5-tetrahydro-4-oxo-1,5-benzothiazepin-3(S)-yl]butanamide;

99. 3-[2(S),3-Dihydroxypropyl]amino-3-methyl-N-[5-[[2'-(benzamido)sulfonyl[1,1'-biphenyl]-4-yl]methyl-8-methylthio-2,3,4,5-tetrahydro-4-oxo-1,5-benzothiazepin-3(S)-yl]butanamide;

100. 3-[2(S),3-Dihydroxypropyl]amino-3-methyl-N-[5-[[2'-(benzamido)sulfonyl[1,1'-biphenyl]-4-yl]methyl- 8-methoxy-2,3,4,5-tetrahydro-4-oxo-1,5-benzothiazepin-3(S)-yl]butanamide;
101. 3-Amino-3-methyl-N-[5-[[2'-(ethylamino)sulfonyl[1,1'-biphenyl]-4-yl]methyl-2,3,4,5-tetrahydro-4-oxo-1,5-benzothiazepin-3(S)-yl]butanamide;
102. 3-Amino-3-methyl-N-[5-[[2'-(ethylamino)sulfonyl[1,1'-biphenyl]-4-yl]methyl-8-fluoro-2,3,4,5-tetrahydro-4-oxo-1,5-benzothiazepin-3(S)-yl]butanamide;
103. 3-Amino-3-methyl-N-[5-[[2'-(ethylamino)sulfonyl[1,1'-biphenyl]-4-yl]methyl-8-trifluoromethyl-2,3,4,5-tetrahydro-4-oxo-1,5-benzothiazepin-3(S)-yl]butanamide;
104. 3-Amino-3-methyl-N-[5-[[2'-(ethylamino)sulfonyl[1,1'-biphenyl]-4-yl]methyl-8-methylthio-2,3,4,5-tetrahydro-4-oxo-1,5-benzothiazepin-3(S)-yl]butanamide;
105. 3-Amino-3-methyl-N-[5-[[2'-(ethylamino)sulfonyl[1,1'-biphenyl]-4-yl]methyl-8-methoxy-2,3,4,5-tetrahydro-4-oxo-1,5-benzothiazepin-3(S)-yl]butanamide;
106. 2-Amino-2-methyl-N-[5-[[2'-(ethylamino)sulfonyl[1,1'-biphenyl]-4-yl]methyl-2,3,4,5-tetrahydro-4-oxo-1,5-benzothiazepin-3(S)-yl]propanamide;
107. 2-Amino-2-methyl-N-[5-[[2'-(ethylamino)sulfonyl[1,1'-biphenyl]-4-yl]methyl-8-fluoro-2,3,4,5-tetrahydro-4-oxo-1,5-benzothiazepin-3(S)-yl]propanamide;
108. 2-Amino-2-methyl-N-[5-[[2'-(ethylamino)sulfonyl[1,1'-biphenyl]-4-yl]methyl-8-trifluoromethyl-2,3,4,5-tetrahydro-4-oxo-1,5-benzothiazepin-3(S)-yl]propanamide;
109. 2-Amino-2-methyl-N-[5-[[2'-(ethylamino)sulfonyl[1,1'-biphenyl]-4-yl]methyl-8-methylthio-2,3,4,5-tetrahydro-4-oxo-1,5-benzothiazepin-3(S)-yl]propanamide;
110. 2-Amino-2-methyl-N-[5-[[2'-(ethylamino)sulfonyl[1,1'-biphenyl]-4-yl]methyl-8-methoxy-2,3,4,5-tetrahydro-4-oxo-1,5-benzothiazepin-3(S)-yl]propanamide;
111. 3-[2(R)-Hydroxypropyl]amino-3-methyl-N-[5-[[2'-(ethylamino)sulfonyl[1,1'-biphenyl]-4-yl]methyl-2,3,4,5-tetrahydro-4-oxo-1,5-benzothiazepin-3(S)-yl]butanamide;
112. 3-[2(R)-Hydroxypropyl]amino-3-methyl-N-[5-[[2'-(ethylamino)sulfonyl[1,1'-biphenyl]-4-yl]methyl-8-fluoro-2,3,4,5-tetrahydro-4-oxo-1,5-benzothiazepin-3(S)-yl]butanamide;
113. 3-[2(R)-Hydroxypropyl]amino-3-methyl-N-[5-[[2'-(ethylamino)sulfonyl[1,1'-biphenyl]-4-yl]methyl-8-trifluoromethyl-2,3,4,5-tetrahydro-4-oxo-1,5-benzothiazepin-3(S)-yl]butanamide;
114. 3-[2(R)-Hydroxypropyl]amino-3-methyl-N-[5-[[2'-(ethylamino)sulfonyl[1,1'-biphenyl]-4-yl]methyl-8-methylthio-2,3,4,5-tetrahydro-4-oxo-1,5-benzothiazepin-3(S)-yl]butanamide;
115. 3-[2(R)-Hydroxypropyl]amino-3-methyl-N-[5-[[2'-(ethylamino)sulfonyl[1,1'-biphenyl]-4-yl]methyl-8-methoxy-2,3,4,5-tetrahydro-4-oxo-1,5-benzothiazepin-3(S)-yl]butanamide;
116. 3-[2(S),3-Dihydroxypropyl]amino-3-methyl-N-[5-[[2'-(ethylamino)sulfonyl[1,1'-biphenyl]-4-yl]methyl-2,3,4,5-tetrahydro-4-oxo-1,5-benzothiazepin-3(S)-yl]butanamide;
117. 3-[2(S),3-Dihydroxypropyl]amino-3-methyl-N-[5-[[2'-(ethylamino)sulfonyl[1,1'-biphenyl]-4-yl]methyl-8-fluoro-2,3,4,5-tetrahydro-4-oxo-1,5-benzothiazepin-3(S)-yl]butanamide;
118. 3-[2(S),3-Dihydroxypropyl]amino-3-methyl-N-[5-[[2'-(ethylamino)sulfonyl[1,1'-biphenyl]-4-yl]methyl-8-trifluoromethyl-2,3,4,5-tetrahydro-4-oxo-1,5-benzothiazepin-3(S)-yl]butanamide;
119. 3-[2(S),3-Dihydroxypropyl]amino-3-methyl-N-[5-[[2'-(ethylamino)sulfonyl[1,1'-biphenyl]-4-yl]methyl-8-methylthio-2,3,4,5-tetrahydro-4-oxo-1,5-benzothiazepin-3(S)-yl]butanamide;
120. 3-[2(S),3-Dihydroxypropyl]amino-3-methyl-N-[5-[[2'-(ethylamino)sulfonyl[1,1'-biphenyl]-4-yl]methyl-8-methoxy-2,3,4,5-tetrahydro-4-oxo-1,5-benzothiazepin-3(S)-yl]butanamide;
121. 3-Amino-3-methyl-N-[5-[[2'-(aminosulfonyl)[1,1'-biphenyl]-4-yl]methyl-2,3,4,5-tetrahydro-4-oxo-1,5-benzothiazepin-3(S)-yl]butanamide;
122. 3-Amino-3-methyl-N-[5-[[2'-(aminosulfonyl)[1,1'-biphenyl]-4-yl]methyl-8-fluoro-2,3,4,5-tetrahydro-4-oxo-1,5-benzothiazepin-3(S)-yl]butanamide;
123. 3-Amino-3-methyl-N-[5-[[2'-(aminosulfonyl)[1,1'-biphenyl]-4-yl]methyl-8-trifluoromethyl-2,3,4,5-tetrahydro-4-oxo-1,5-benzothiazepin-3(S)-yl]butanamide;
124. 3-Amino-3-methyl-N-[5-[[2'-(aminosulfonyl)[1,1'-biphenyl]-4-yl]methyl-8-methylthio-2,3,4,5-tetrahydro-4-oxo-1,5-benzothiazepin-3(S)-yl]butanamide;
125. 3-Amino-3-methyl-N-[5-[[2'-(aminosulfonyl)[1,1'-biphenyl]-4-yl]methyl-8-methoxy-2,3,4,5-tetrahydro-4-oxo-1,5-benzothiazepin-3(S)-yl]butanamide;
126. 2-Amino-2-methyl-N-[5-[[2'-(aminosulfonyl)[1,1'-biphenyl]-4-yl]methyl-2,3,4,5-tetrahydro-4-oxo-1,5-benzothiazepin-3(S)-yl]propanamide;
127. 2-Amino-2-methyl-N-[5-[[2'-(aminosulfonyl)[1,1'-biphenyl]-4-yl]methyl-8-fluoro-2,3,4,5-tetrahydro-4-oxo-1,5-benzothiazepin-3(S)-yl]propanamide;
128. 2-Amino-2-methyl-N-[5-[[2'-(aminosulfonyl)[1,1'-biphenyl]-4-yl]methyl-8-trifluoromethyl-2,3,4,5-tetrahydro-4-oxo-1,5-benzothiazepin-3(S)-yl]propanamide;
129. 2-Amino-2-methyl-N-[5-[[2'-(aminosulfonyl)[1,1'-biphenyl]-4-yl]methyl-8-methylthio-2,3,4,5-tetrahydro-4-oxo-1,5-benzothiazepin-3(S)-yl]propanamide;
130. 2-Amino-2-methyl-N-[5-[[2'-(aminosulfonyl)[1,1'-biphenyl]-4-yl]methyl-8-methoxy-2,3,4,5-tetrahydro-4-oxo-1,5-benzothiazepin-3(S)-yl]propanamide;
131. 3-[2(R)-Hydroxypropyl]amino-3-methyl-N-[5-[[2'-(aminosulfonyl)[1,1'-biphenyl]-4-yl]methyl-2,3,4,5-tetrahydro-4-oxo-1,5-benzothiazepin-3(S)-yl]butanamide;
132. 3-[2(R)-Hydroxypropyl]amino-3-methyl-N-[5-[[2'-(aminosulfonyl)[1,1'-biphenyl]-4-yl]methyl-8-fluoro-2,3,4,5-tetrahydro-4-oxo-1,5-benzothiazepin-3(S)-yl]butanamide;
133. 3-[2(R)-Hydroxypropyl]amino-3-methyl-N-[5-[[2'-(aminosulfonyl)[1,1'-biphenyl]-4-yl]methyl-8-trifluoromethyl-2,3,4,5-tetrahydro-4-oxo-1,5-benzothiazepin-3(S)-yl]butanamide;
134. 3-[2(R)-Hydroxypropyl]amino-3-methyl-N-[5-[[2'-(aminosulfonyl)[1,1'-biphenyl]-4-yl]methyl-8-methylthio-2,3,4,5-tetrahydro-4-oxo-1,5-benzothiazepin-3(S)-yl]butanamide;
135. 3-[2(R)-Hydroxypropyl]amino-3-methyl-N-[5-[[2'-(aminosulfonyl)[1,1'-biphenyl]-4-yl]methyl-8-methoxy-2,3,4,5-tetrahydro-4-oxo-1,5-benzothiazepin-3(S)-yl]butanamide;
136. 3-[2(S),3-Dihydroxypropyl]amino-3-methyl-N-[5-[[2'-(aminosulfonyl)[1,1'-biphenyl]-4-yl]methyl-2,3,4,5-tetrahydro-4-oxo-1,5-benzothiazepin-3(S)-yl]butanamide;

137. 3-[2(S),3-Dihydroxypropyl]amino-3-methyl-N-[5-[[2'-(aminosulfonyl)[1,1'-biphenyl]-4-yl]methyl-8-fluoro-2,3,4,5-tetrahydro-4-oxo-1,5-benzothiazepin-3(S)-yl]butanamide;

138. 3-[2(S),3-Dihydroxypropyl]amino-3-methyl-N-[5-[[2'-(aminosulfonyl)[1,1'-biphenyl]-4-yl]methyl-8-trifluoromethyl-2,3,4,5-tetrahydro-4-oxo-1,5-benzothiazepin-3(S)-yl]butanamide;

139. 3-[2(S),3-Dihydroxypropyl]amino-3-methyl-N-[5-[[2'-(aminosulfonyl)[1,1'-biphenyl]-4-yl]methyl-8-methylthio-2,3,4,5-tetrahydro-4-oxo-1,5-benzothiazepin-3(S)-yl]butanamide;

140. 3-[2(S),3-Dihydroxypropyl]amino-3-methyl-N-[5-[[2'-(aminosulfonyl)[1,1'-biphenyl]-4-yl]methyl-8-methoxy-2,3,4,5-tetrahydro-4-oxo-1,5-benzothiazepin-3(S)-yl]butanamide;

141. 3-Amino-3-methyl-N-[5-[[2'-(t-butylamino)sulfonyl[1,1'-biphenyl]-4-yl]methyl-2,3,4,5-tetrahydro-4-oxo-1,5-benzothiazepin-3(S)-yl]butanamide;

142. 3-Amino-3-methyl-N-[5-[[2'-(t-butylamino)sulfonyl[1,1'-biphenyl]-4-yl]methyl-8-fluoro-2,3,4,5-tetrahydro-4-oxo-1,5-benzothiazepin-3(S)-yl]butanamide;

143. 3-Amino-3-methyl-N-[5-[[2'-(t-butylamino)sulfonyl[1,1'-biphenyl]-4-yl]methyl-8-trifluoromethyl-2,3,4,5-tetrahydro-4-oxo-1,5-benzothiazepin-3(S)-yl]butanamide;

144. 3-Amino-3-methyl-N-[5-[[2'-(t-butylamino)sulfonyl[1,1'-biphenyl]-4-yl]methyl-8-methylthio-2,3,4,5-tetrahydro-4-oxo-1,5-benzothiazepin-3(S)-yl]butanamide;

145. 3-Amino-3-methyl-N-[5-[[2'-(t-butylamino)sulfonyl[1,1'-biphenyl]-4-yl]methyl-8-methoxy-2,3,4,5-tetrahydro-4-oxo-1,5-benzothiazepin-3(S)-yl]butanamide;

146. 2-Amino-2-methyl-N-[5-[[2'-(t-butylamino)sulfonyl[1,1'-biphenyl]-4-yl]methyl-2,3,4,5-tetrahydro-4-oxo-1,5-benzothiazepin-3(S)-yl]propanamide;

147. 2-Amino-2-methyl-N-[5-[[2'-(t-butylamino)sulfonyl[1,1'-biphenyl]-4-yl]methyl-8-fluoro-2,3,4,5-tetrahydro-4-oxo-1,5-benzothiazepin-3(S)-yl]propanamide;

148. 2-Amino-2-methyl-N-[5-[[2'-(t-butylamino)sulfonyl[1,1'-biphenyl]-4-yl]methyl-8-trifluoromethyl-2,3,4,5-tetrahydro-4-oxo-1,5-benzothiazepin-3(S)-yl]propanamide;

149. 2-Amino-2-methyl-N-[5-[[2'-(t-butylamino)sulfonyl[1,1'-biphenyl]-4-yl]methyl-8-methylthio-2,3,4,5-tetrahydro-4-oxo-1,5-benzothiazepin-3(S)-yl]propanamide;

150. 2-Amino-2-methyl-N-[5-[[2'-(t-butylamino)sulfonyl[1,1'-biphenyl]-4-yl]methyl-8-methoxy-2,3,4,5-tetrahydro-4-oxo-1,5-benzothiazepin-3(S)-yl]propanamide;

151. 3-[2(R)-Hydroxypropyl]amino-3-methyl-N-[5-[[2'-(t-butylamino)sulfonyl[1,1'-biphenyl]-4-yl]methyl-2,3,4,5-tetrahydro-4-oxo-1,5-benzothiazepin-3(S)-yl]butanamide;

152. 3-[2(R)-Hydroxypropyl]amino-3-methyl-N-[5-[[2'-(t-butylamino)sulfonyl[1,1'-biphenyl]-4-yl]methyl-8-fluoro-2,3,4,5-tetrahydro-4-oxo-1,5-benzothiazepin-3(S)-yl]butanamide;

153. 3-[2(R)-Hydroxypropyl]amino-3-methyl-N-[5-[[2'-(t-butylamino)sulfonyl[1,1'-biphenyl]-4-yl]methyl-8-trifluoromethyl-2,3,4,5-tetrahydro-4-oxo-1,5-benzothiazepin-3(S)-yl]butanamide;

154. 3-[2(R)-Hydroxypropyl]amino-3-methyl-N-[5-[[2'-(t-butylamino)sulfonyl[1,1'-biphenyl]-4-yl]methyl-8-methylthio-2,3,4,5-tetrahydro-4-oxo-1,5-benzothiazepin-3(S)-yl]butanamide;

155. 3-[2(R)-Hydroxypropyl]amino-3-methyl-N-[5-[[2'-(t-butylamino)sulfonyl[1,1'-biphenyl]-4-yl]methyl-8-methoxy-2,3,4,5-tetrahydro-4-oxo-1,5-benzothiazepin-3(S)-yl]butanamide;

156. 3-[2(S),3-Dihydroxypropyl]amino-3-methyl-N-[5-[[2'-(t-butylamino)sulfonyl[1,1'-biphenyl]-4-yl]methyl-2,3,4,5-tetrahydro-4-oxo-1,5-benzothiazepin-3(S)-yl]butanamide;

157. 3-[2(S),3-Dihydroxypropyl]amino-3-methyl-N-[5-[[2'-(t-butylamino)sulfonyl[1,1'-biphenyl]-4-yl]methyl-8-fluoro-2,3,4,5-tetrahydro-4-oxo-1,5-benzothiazepin-3(S)-yl]butanamide;

158. 3-[2(S),3-Dihydroxypropyl]amino-3-methyl-N-[5-[[2'-(t-butylamino)sulfonyl[1,1'-biphenyl]-4-yl]methyl-8-trifluoromethyl-2,3,4,5-tetrahydro-4-oxo-1,5-benzothiazepin-3(S)-yl]butanamide;

159. 3-[2(S),3-Dihydroxypropyl]amino-3-methyl-N-[5-[[2'-(t-butylamino)sulfonyl[1,1'-biphenyl]-4-yl]methyl-8-methylthio-2,3,4,5-tetrahydro-4-oxo-1,5-benzothiazepin-3(S)-yl]butanamide; and 160. 3-[2(S),3-Dihydroxypropyl]amino-3-methyl-N-[5-[[2'-(t-butylamino)sulfonyl[1,1'-biphenyl]-4-yl]methyl-8-methoxy-2,3,4,5-tetrahydro-4-oxo-1,5-benzothiazepin-3(S)-yl]butanamide.

Representative examples of the nomenclature employed are given below:
3-Amino-3-methyl-N-[1-[[2'-[[(methylaminocarbonyl)amino]sulfonyl][1,1'-biphenyl]-4-yl]methyl]-2,3,4,5-tetrahydro-2-oxo-1H-1-benzazepin-3(R)-yl]butanamide

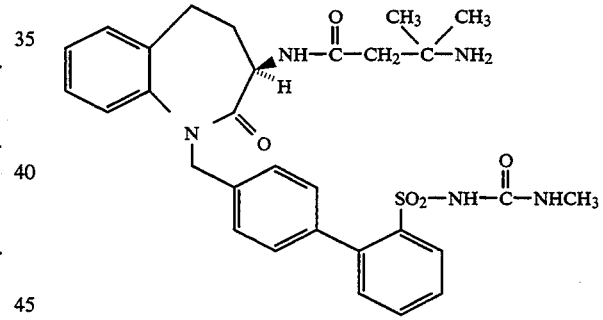

2-Amino-2-methyl-N-[1-[[2'-(benzamido)sulfonyl[1,1'-biphenyl]-4-yl]methyl]-7-methyl-2,3,4,5-tetrahydro-2-oxo-1H-1-benzazepin-3(R)-yl]propanamide

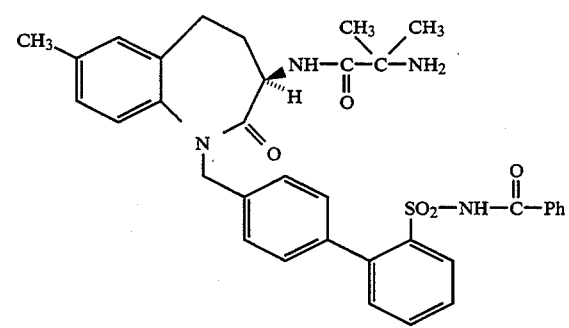

3-[2(R)-Hydroxypropyl]amino-3-methyl-N-[1-[[2'-[(pyrrolidin-1-yl)sulfonyl][1,1'-biphenyl]-4-yl]methyl]-2,3,4,5-tetrahydro-2-oxo-1H-1-benzazepin-3(R)-yl]butanamide

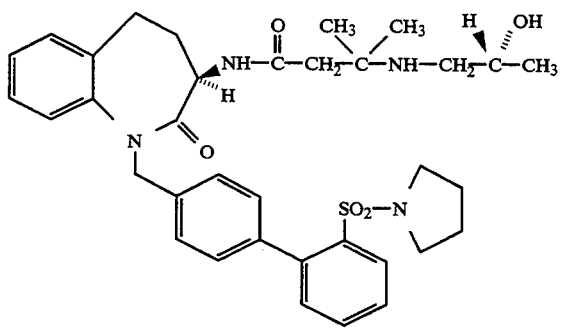

3-[2(S),3-Dihydroxypropyl]amino-3-methyl-N-[2,3,4-,5-tetrahydro-5-[[2'-[2-[[[4-morpholinocarbonyl]amino]-sulfonyl]methyl][1,1'-biphenyl]-4-yl]methyl]-7-methyl-4-oxo-1,5-benzothiazepin-3(S)-yl]butanamide

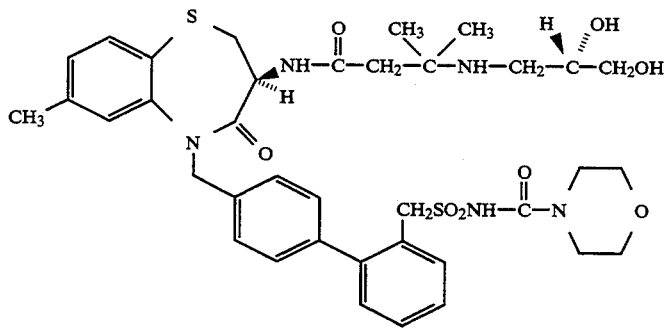

The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the 3-amino substituent is above the plane of the structure, as seen in Formula Ia, is more active and thus more preferred over the compound in which the 3-amino substituent is below the plane of the structure. In the substituent $(X)_n$, when n=0, the asymmetric center is designated as the R-isomer. When n=1, this center will be designated according to the R/S rules as either R or S depending upon the value of X.

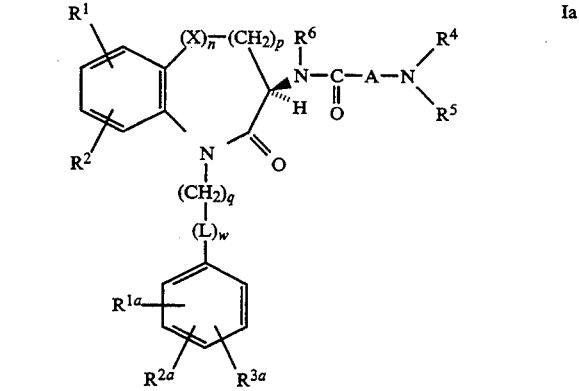

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The compounds (I) of the present invention are prepared from intermediates such as those of formula H. The preparation of these intermediates is described in the following reaction Schemes.

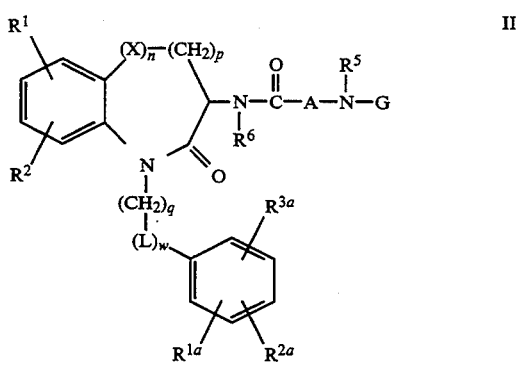

Compounds of formula H are prepared by alkylation of intermediates of formula III as shown in Scheme 1. The preparation of compounds of formula III has been previously described by Fisher, et al, U.S. Pat. No. 5,206,235 and references cited therein. Alkylation of intermediates of formula III is conveniently carried out in anhydrous dimethyl formamide (DMF) in the presence of bases such as sodium hydride or potassium t-butoxide for a period of 0.5 to 24 hours at temperatures of 20°–100° C., with an alkylating agent IV, wherein Y is a good leaving group such as Cl, Br, I, O-methanesulfonyl or O-(p-toluenesulfonyl). Separation of unwanted side products, and purification of products is achieved by chromatography on silica gel, employing flash chromatography (W. C. Still, M. Kahn and A. Mitra, J. Org. Chem., 43, 2923(1978)) or by medium pressure liquid chromatography. Substituents on the alkylating agent IV may need to be protected during alkylation. A description of such protecting groups may be found in: *Protective Groups in Organic Synthesis*, T. W. Greene, John Wiley and Sons, New York, 1981.

SCHEME 1

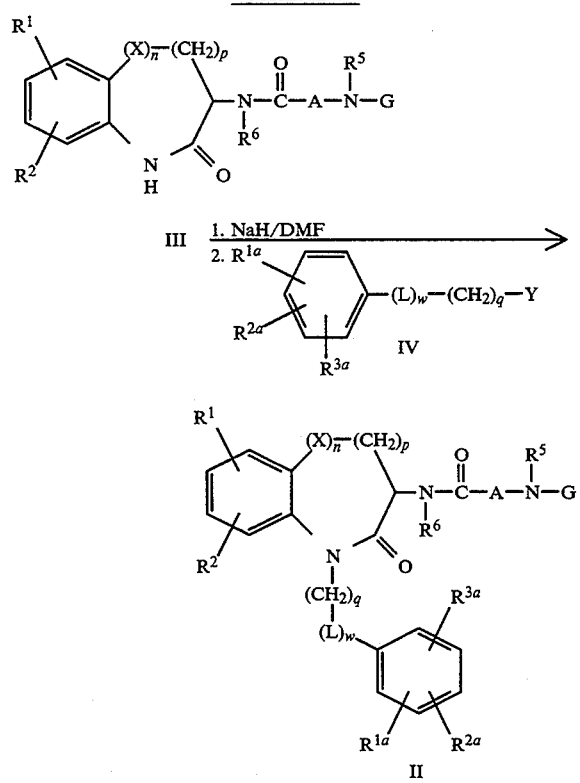

Y is a leaving group
G is t-butoxycarbonyl or benzyloxycarbonyl

Compounds of formula II wherein $R^{3a}$ is taken as $-SO_2NR^{4a}R^{12a}$ are prepared from the sulfonyl chloride 1 as shown in Scheme 2. Reaction of 1 with the secondary amine $R^{4a}R^{12a}NH$ in an inert solvent such as methylene chloride in the presence of a base, such as triethylamine or 4-dimethylaminopyridine, gives the sulfonamide product 2. Reaction of 2 with compounds of formula III is carried out using the conditions described in Scheme 1.

SCHEME 2

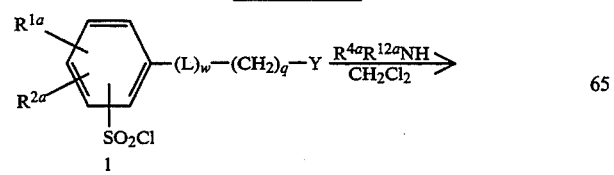

-continued
SCHEME 2

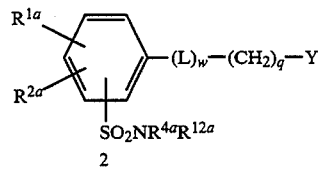

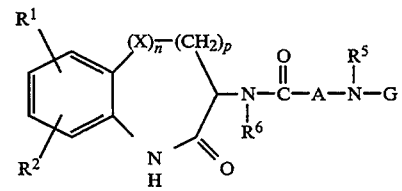

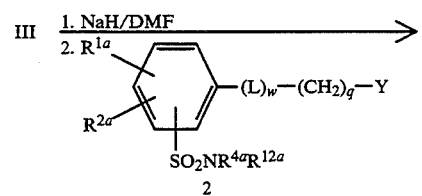

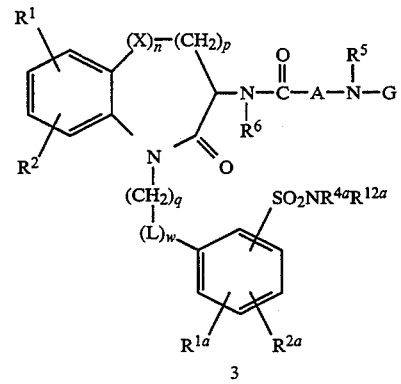

Y is a leaving group
G is t-butoxycarbonyl or benzyloxycarbonyl

As shown in Scheme 3, an analogous series of transformations is employed to assemble compounds of formula II wherein $R^{3a}$ is defined as $-SO_2N(R^{12b})N-R^{4a}R^{12a}$ (5).

SCHEME 3

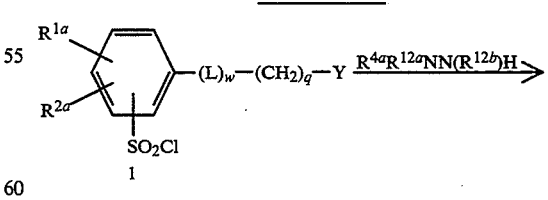

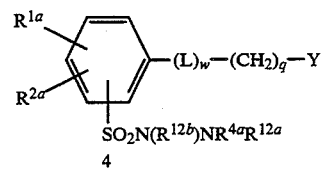

-continued
SCHEME 3

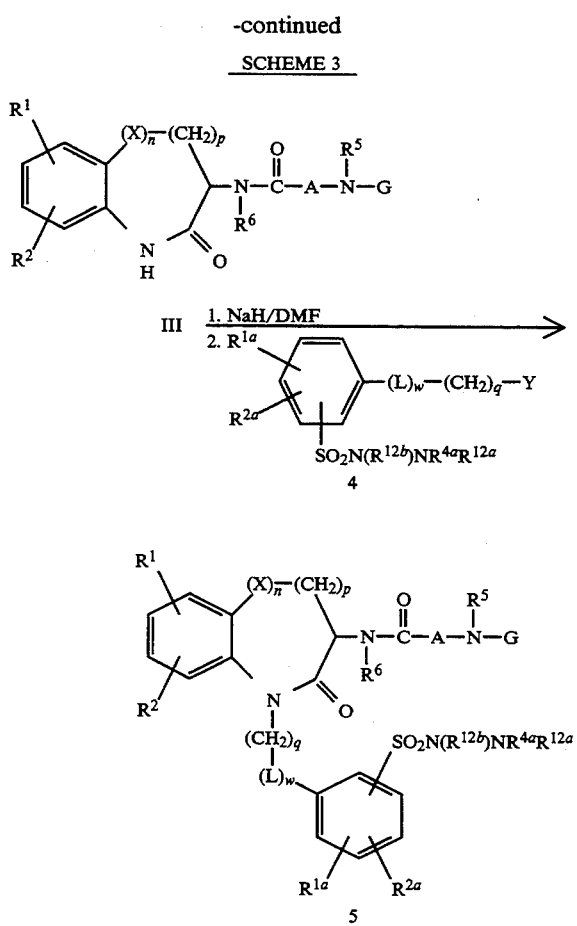

Y is a leaving group
G is t-butoxycarbonyl or benzyloxycarbonyl

Reaction of sulfonyl chloride 1 with the secondary amine t-BuN(R$^{12b}$)H and subsequent alkylation with III by the aforementioned procedures, leads to intermediate 7 (Scheme 4).

SCHEME 4

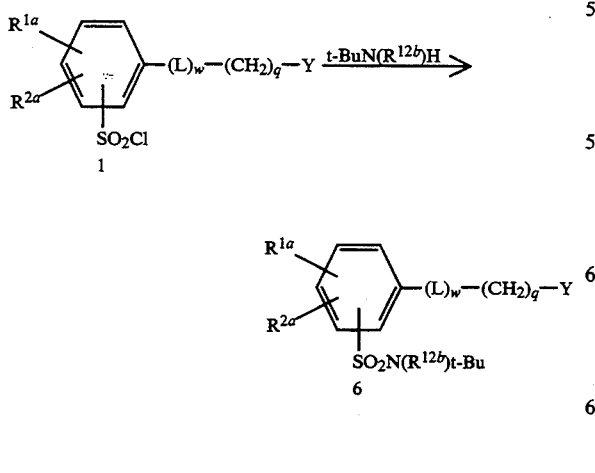

-continued
SCHEME 4

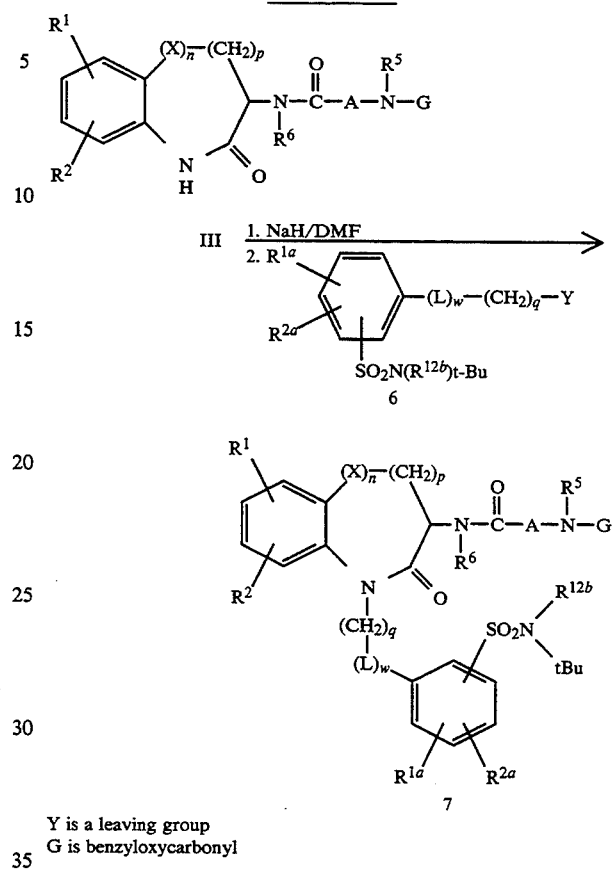

Y is a leaving group
G is benzyloxycarbonyl

A useful synthesis of intermediate 12 is outlined in Scheme 5. Reaction of o-bromobenzenesulfonyl chloride 8 with t-butylamine in methylene chloride gives the t-butyl sulfonamide 9 in high yield. Reaction of 9 with 4-methylphenyltrimethylstannane 10 in the presence of bis(triphenylphosphine)palladium(II) chloride in dimethylformamide at elevated temperature gives the coupled product 11 in good yield. Conversion to bromide 12 is achieved by free radical bromination with N-bromosuccinimide in carbon tetrachloride in the presence of the radical initiator, azobisisobutyronitrile (AIBN). Reaction of 12 with compounds of formula III is carried out using the conditions described in Scheme 1.

SCHEME 5

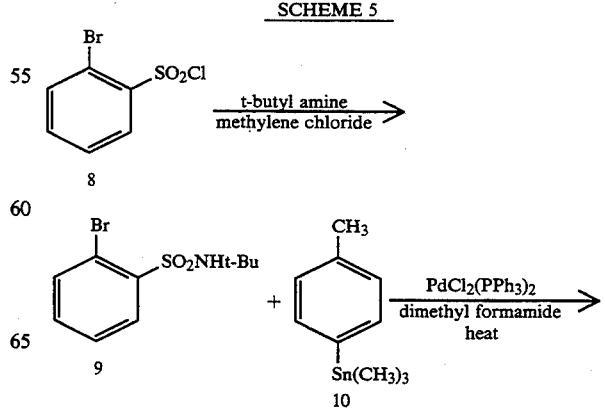

-continued
SCHEME 5

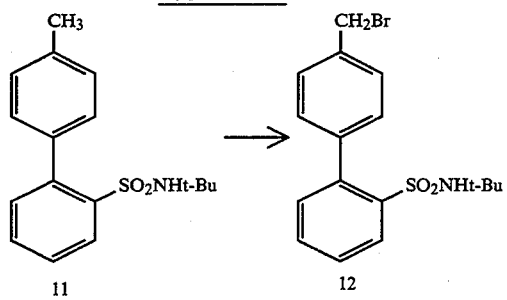

Intermediate 7 may be converted to a new intermediate 13 by removal of the t-butyl group. As shown in Scheme 6, treatment of 7 with a strong acid, such as hydrochloric acid in methanol or trifluoroacetic acid in methylene chloride, results in loss of the t-butyl group to give the product. It may be appreciated by one skilled in the art that the protecting group G in 7 must therefore be compatible with the strongly acidic conditions employed; hence G is taken as benzyloxycarbonyl.

SCHEME 6

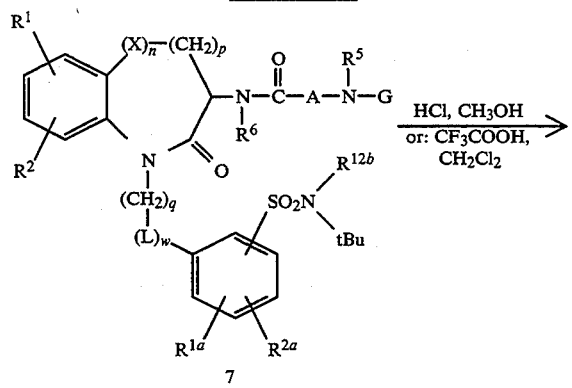

Y is a leaving group
G is benzyloxycarbonyl

Acylsulfonamide compounds of-formula II (14) are prepared from intermediate 13 as indicated in Scheme 7. Acylation of 13 is carried out by treatment with reaction with the activated acyl imidazolide intermediate derived from $R^{5a}$COOH and N,N'-carbonyldiimidazole.
Alternatively, the acylsulfonamide product 14 is obtained by reaction of 13 with the acid chloride, $R^{5a}$COCl.

SCHEME 7

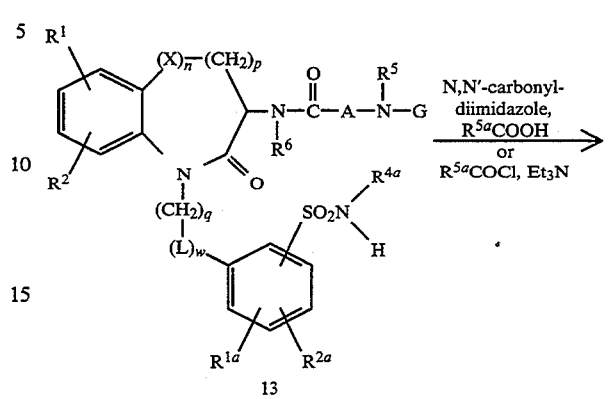

G is benzyloxycarbonyl

Intermediate 13 is also converted into N-carbamoyl and N-alkoxycarbonyl sulfonamides. Reaction of 13 with substituted carbamoyl chloride reagent 15 in an inert solvent such as methylene chloride in the presence of a triethylamine or 4-dimethylaminopyridine affords the N-carbamoyl sulfonamide product 16 as shown in Scheme 8.

SCHEME 8

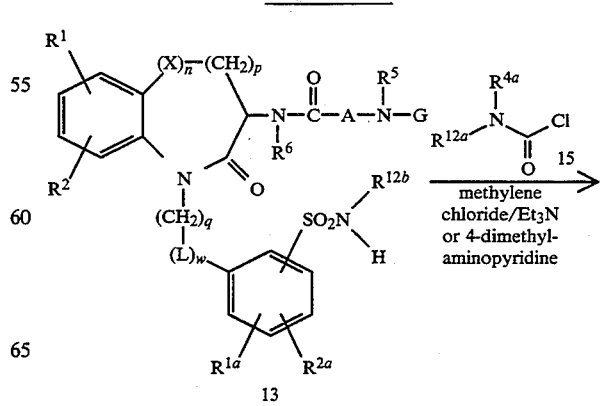

-continued
SCHEME 8

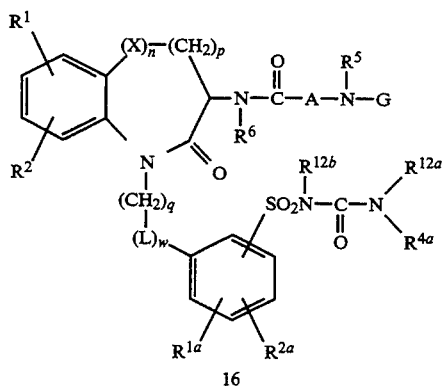

G is benzyloxycarbonyl

An analogous sequence is employed in the synthesis of N-thiocarbamoyl sulfonamide 18 using the thiocarbamoyl reagent 17 as outlined in Scheme 9.

SCHEME 9

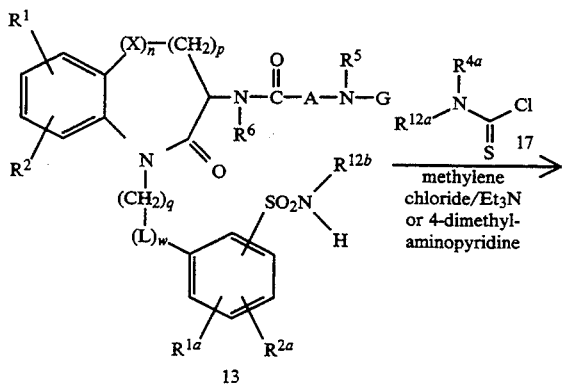

G is benzyloxycarbonyl

As illustrated in Scheme 10, reaction of 13 with an isocyanate reagent 19 also gives an N-carbamoyl sulfonamide product 20 wherein $R^{4a}$ is hydrogen. The corresponding N-thiocarbamoyl sulfonamide analog of 20 can also be obtained by reaction of 13 with an appropriate isothiocyanate.

SCHEME 10

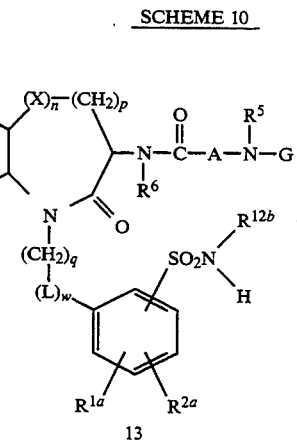

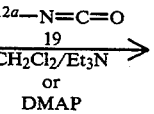

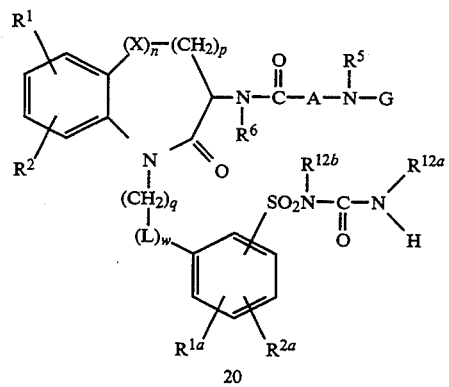

G is benzyloxycarbonyl

N-Alkoxycarbonyl sulfonamides 22 are also prepared from 13 by reaction with a chloroformate (or equivalent) reagent 21 as shown in Scheme 11.

SCHEME 11

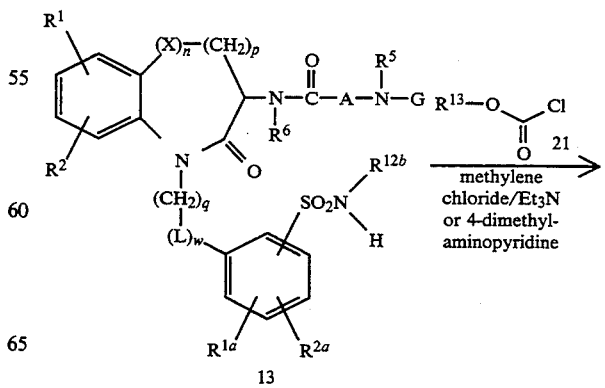

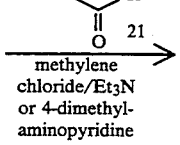

-continued
SCHEME 11

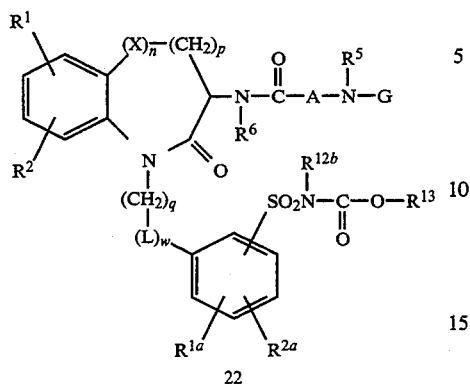
22

G is benzyloxycarbonyl

Substituted hydrazide compounds of formula II (23) are prepared from intermediate 13 by a two-step sequence consisting of treatment of the hydrazine compound $R^{4a}R^{12a}NN(R^{12b})H$ with N,N'-carbonyldiimidazole, followed by reaction of the active species thus formed with intermediate 13 (Scheme 12).

SCHEME 12

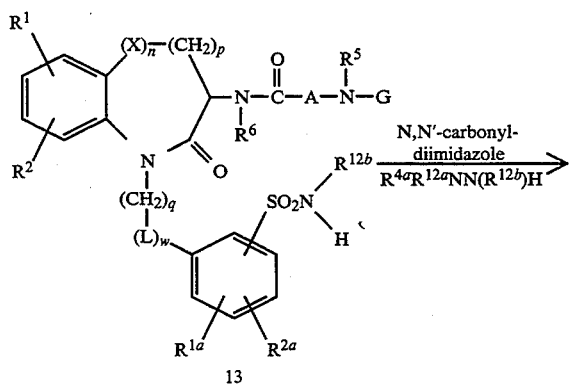

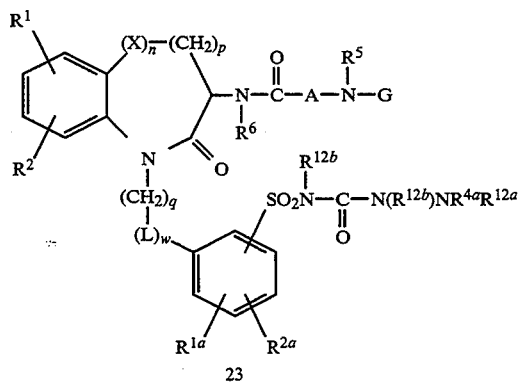
23

G is benzyloxycarbonyl

The corresponding thio analog of 23 can be obtained from 13 by the aforementioned procedure by substituting N,N'-thiocarbonyldiimidazole for N,N'-carbonyldiimidazole.

Conversion to the final products of formula I wherein $R^4$ is hydrogen, is carried out by simultaneous or sequential removal of all protecting groups from intermediate II as illustrated in Scheme 13.

SCHEME 13

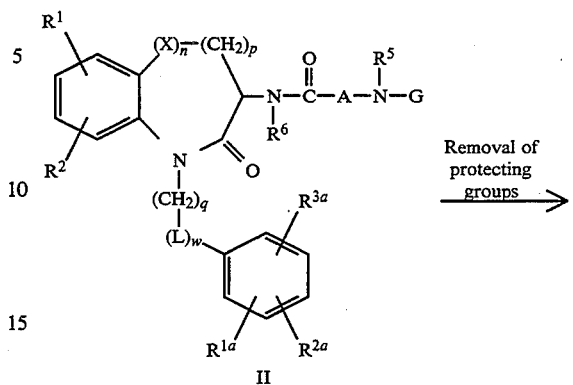
II

Removal of protecting groups →

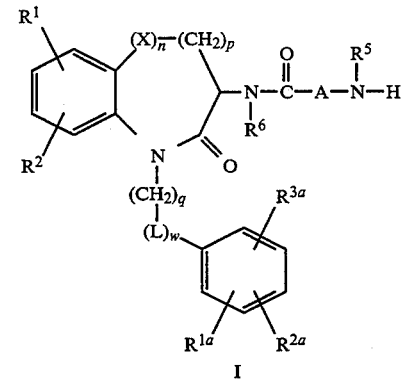
I

Removal of benzyloxycarbonyl (CBz) groups can be achieved by a number of methods known in the art; for example, catalytic hydrogenation with hydrogen in the presence of a platinum or palladium catalyst in a protic solvent such as methanol. In cases where catalytic hydrogenation is contraindicated by the presence of other potentially reactive functionality, removal of benzyloxycarbonyl groups can also be achieved by treatment with a solution of hydrogen bromide in acetic acid. Removal of t-butoxycarbonyl (BOC) protecting groups is carried out by treatment of a solution in a solvent such as methylene chloride or methanol, with a strong acid, such as hydrochloric acid or trifluoroacetic acid. Conditions required to remove other protecting groups which may be present can be found in *Protective Groups in Organic Synthesis* T. W. Greene, John Wiley and Sons, N.Y. 1981.

As shown in Scheme 14, compounds of formula I wherein $R^4$ and $R^5$ are each hydrogen can be further elaborated to new compounds which are substituted on the amino group. Reductive alkylation with an aldehyde is carried out under conditions known in the art; for example, by catalytic hydrogenation with hydrogen in the presence of platinum, palladium or nickel catalysts or with chemical reducing agents such as sodium cyanoborohydride in an inert solvent such as methanol or ethanol. Substitution on the amine can also be achieved by reaction with various epoxides. The products, obtained as hydrochloride or trifluoroacetate salts, are conveniently purified by reverse phase high performance liquid chromatography (HPLC) or by recrystallization.

SCHEME 14

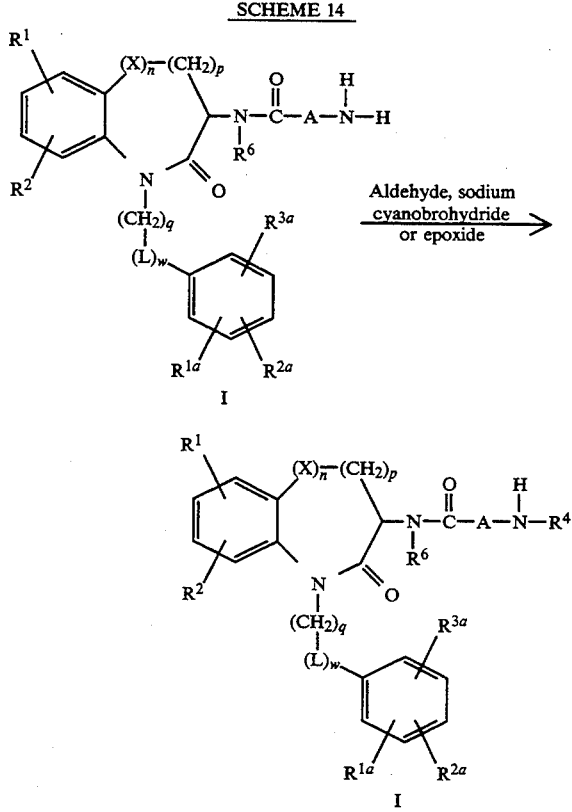

It is noted that the order of carrying out the foregoing reaction schemes is not significant and it is within the skill of one skilled in the art to vary the order of reactions to facilitate the reaction or to avoid unwanted reaction products.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive intestinal peptides, e.g., bombesin; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise a growth promoting agent in addition to at least one of the compounds of Formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the disclosed novel benzo-fused lactam growth hormone secretagogues is in combination with other growth hormone secretagogues such as GHRP-6, GHRP-1 or GHRP-2 as described in U.S. Pat. Nos. 4,411,890; and publications WO 89/07110, WO 89/07111 and WO 93/04081 or B-HT 920 or in combination with growth hormone releasing factor and its analogs or growth hormone and its analogs. A still further use of the disclosed novel benzo-fused lactam growth hormone secretagogues is in combination with $\alpha_2$ adrenergic agonists or $\beta_3$ adrenergic agonists in the treatment of obesity or in combination with parathyroid hormone or bisphosphonates, such as MK-217 (alendronate), in the treatment of osteoporosis. A still further use of the disclosed novel benzo-fused lactam growth hormone secretagogues is in combination with IGF-1 to reverse the catabolic effects of nitrogen wasting as described by Kupfer, et al, J. Clin. Invest., 91, 391 (1993).

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; prevention of catabolic side effects of glucocorticoids; treatment of osteoporosis; stimulation of the immune system; treatment of retardation; acceleration of wound healing; accelerating bone fracture repair; treatment of growth retardation, treating renal failure or insufficiency resulting in growth retardation; treatment of physiological short stature, including growth hormone deficient children; treating short stature associated with chronic illness; treatment of obesity and growth retardation associated with obesity; treating growth retardation associated with Prader-Willi syndrome and Turner's syndrome; accelerating the recovery and reducing hospitalization of burn patients; treatment of intrauterine growth retardation, skeletal dysplasia, hypercortisolism and Cushings syndrome; induction of pulsatile growth hormone release; replacement of growth hormone in stressed patients; treatment of osteochondrodysplasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; reducing cachexia and protein loss due to chronic illness such as cancer or AIDS. Treatment of hyperinsulinemia including nesidioblastosis; adjuvant treatment for ovulation induction; to stimulate thymic development and prevent the age-related decline of thymic function; treatment of immunosuppressed patients; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock and stimulation of wool growth in sheep.

The compounds of this invention can be administered by oral, parenteral (e.g., intramuscular, intraperitoneal, intravenous or subcutaneous injection or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/Kg of body weight daily are administered to patients and animals, e.g., mammals, to obtain effective release of growth hormone.

The following examples are provided for the purpose of further illustration only and are not intended to be limitations on the disclosed invention.

EXAMPLE 1

3-Amino-3-methyl-N-[2,3,4,5-tetrahydro-2-oxo-1-[[2'-(benzamido)sulfonyl[1,1'-biphenyl]-4-yl]methyl]-1H-1-benzazepin-3(R)-yl]butanamide, trifluoroacetate Step A: 1-Bromo-2-t-butylbenzenesulfonamide To a solution of 51.4 g (0.201 mol, 1.0 eq.) of o-bromobenzenesulfonyl chloride in 1 L of chloroform was added 53 mL of t-butylamine (36.8 g, 0.504 mol, 2.5 eq) dropwise with stirring at room temperature under nitrogen. The solution was stirred overnight at room temperature, then concentrated to dryness under vacuum to give 75.93 g of crude material. Thin layer chromatography on a silica plate eluting with 50% ethyl acetate in hexane showed one spot. The crude product was suspended in methylene chloride and the insoluble t-butylamine hydrochloride removed by filtration. The solution was concentrated to dryness under vacuum to give 57.85 g (0.198 mol, 98%) of the product. $^1$H NMR (CDCl$_3$, 200 MHz): $\delta$ 1.29 (s, 9H), 5.18 (br s, 1H), 7.4–7.6 (m, 2H), 7.78 (dd; 2, 8 Hz; 1H), 8.14 (dd; 2, 8 Hz; 1H). FAB-MS (Li+ spike): calculated for C$_{10}$H$_{14}$BrNO$_2$S 291,293; found 298, 300 (M+Li, 30%).

Step B: 4-Methylphenyltrimethylstannane 41.4 L of 1.0M p-tolylmagnesium bromide in diethyl ether (41.4 mol) was added dropwise, maintaining the temperature below −5° C., over 4 hours to a solution of 546 g (2.79 mol) of trimethyltin chloride in tetrahydrofuran (4 L) under nitrogen at −10° C. The suspension was allowed to warm slowly to room temperature over 12 hours then saturated ammonium chloride solution (1 L) was added followed by sufficient water (approximately 1 L) to dissolve the precipitate. The solution was extracted with ether-hexane (1:1) (1×4 L, 3×2 L). The combined organic phases were washed with brine, dried over magnesium sulfate and the solvents removed under vacuum. Purification by flash chromatography on silica gel eluting with hexane/ethyl acetate (95:5) gave a pale yellow oil containing white crystals of 4,4'-dimethylbiphenyl which were removed by filtration to leave 711.3 g (100%) of product. $^1$H NMR (300 MHz, CDCl$_3$): $\delta$ 0.30 (s, 9H), 2.34 (s, 3H), 7.19 (d, 7.7 Hz, 2H), 7.40 (d, 7.7 Hz, 2H).

Step C: 4-Methyl-2'-(t-butylaminosulfonyl)-1,1'-biphenyl

1-Bromo-2-t-butylbenzenesulfonamide (22.4 g, 77 mmol) (Step A) and 4-methylphenyltrimethylstannane (39.35 g, 154 mmol 2eq.) were dissolved in 221 mL of dry dimethylformamide and the resulting solution treated with 2.71 g (38.6 mmol, 0.5eq) of bis(triphenylphosphine)palladium(II) chloride. The mixture was heated at 90° C. for 6 hours. The mixture was filtered through Celite and the filter cake was washed with ether. The combined organics were washed twice with water. The aqueous washings were combined and extracted with ether. The combined organics were washed with saturated aqueous sodium chloride then dried over magnesium sulfate, filtered and concentrated to dryness to yield the product which solidified on standing. Purification by preparative HPLC on silica, eluting with 10% ethyl acetate/hexane, gave 13.63 g (44.98 mmol, 58%) of the product as a yellow powder. $^1$H NMR (200 MHz, CDCl$_3$): δ 1.09 (s, 9H), 2.50 (s, 3H), 3.64 (br s, 1H), 7.3–7.7 (m,7H), 8.13 (dd; 2, 8 Hz; 1H). FAB-MS: calculated for $C_{17}H_{21}NO_2S$ 303; found 304 (M+H, 3%).

Step D: 4-Bromomethyl-2'-(t-butylamino)sulfonyl-1,1'-biphenyl

To a solution of 5.0 g (16.5 mmol) of 4-methyl-2'-(t-butylaminosulfonyl)-1,1'-biphenyl in 400 mL of carbon tetrachloride was added 2.35 g (13.2 mmol, 0.8eq) of recrystallized N-bromosuccinimide and 27.5 mg of azobisisobutyronitrile (AIBN). The mixture was refluxed under a nitrogen amosphere for 4 hours at which time an additional 1.17 g (6.57 mmol, 0.40 eq) of N-bromosuccinimide and a trace of AIBN were added and refluxing continued for another 2 hours. The mixture was cooled to room temperature, filtered and the filtrate concentrated to dryness to give 7.11 g of crude product which was used without further purification. $^1$H NMR (200 MHz, CDCl$_3$): δ 1.07 (s, 9H), 3.63 (br s, 1H), 4.60 (s, 2H), 7.3–7.7 (m,7H), 8.11 (dd; 2, 8 Hz; 1H). FAB-MS: calculated for $C_{17}H_{20}BrNO_2S$ 381; found 382 (M+H, 2.5%).

Step E: 3-Benzyloxycarbonylamino-3-methyl-N-[2,3,4,5-tetrahydro-2-oxo-1-[[2'-(t-butylamino)sulfonyl[1,1'-biphenyl]-4-yl]methyl]-1H-1-benzazepin-3(R)-yl]butanamide A solution of 250 mg (0.610 mmol) of 3-benzyloxycarbonylamino-3-methyl-N-[2,3,4,5-tetrahydro-2-oxo-1H-1-benzazepin-3(R)-yl]butanamide (prepared by the method of Fisher, et al; U.S. Pat. No. 5,206,235) in 1.5 mL of dimethylformamide at room temperature was treated with 32 mg of 60% sodium hydride oil dispersion (19 mg NaH, 0.79 mmol, 1.3eq). The mixture was stirred under nitrogen at room temperature for 20 minutes then treated with a solution of 303 mg (0.79 mmol, 1.3eq) of 4-bromomethyl-2'-(t-butylamino)sulfonyl-1,1'-biphenyl in 1 mL of dimethylformamide. The solution was stirred at room temperature for 12 hours then diluted with ethyl acetate and washed with pH$_7$ phosphate buffer solution (3×) and saturated aqueous sodium chloride. The washings were extracted once with ethyl acetate and the combined ethyl acetate solutions were dried over magnesium sulfate, filtered and concentrated to dryness to give the crude product which solidified upon standing. Purification by preparative HPLC on silica, eluting with ethyl acetate/hexane (2/1), gave 200 mg (0.28 mmol, 46%) of the product. $^1$H NMR (200 MHz, CDCl$_3$): δ 1.00 (s, 9H), 1.45 (s, 3H), 1.47 (s, 3H), 1.85 (m, 1H), 2.4–2.7 (m, 5H), 3.42 (s, 1H), 4.59 (m, 1H), 4.79 (s, 1H), 4.92 (d, 15 Hz, 1H), 5.15 (s, 2H), 5.18 (d, 15 Hz, 1H), 5.66 (br s, 1H), 6.72.(d, 8 Hz, 1H), 7.15–7.65 (m, 16H), 8.18 (dd; 2, 8 Hz; 1H). FAB-MS: calculated for $C_{40}H_{46}N_4O_6S$ 710; found 711 (M+H, 15%).

Step F: 3-Benzyloxycarbonylamino-3-methyl-N-[2,3,4,5-tetrahydro-2-oxo-1-[[2'-aminosulfonyl[1,1'-biphenyl]-4-yl]methyl-1H-1-benzazepin-3(R)-yl]butanamide A solution of 200 mg (0.282 mmol) of the intermediate obtained in Step E in 3 mL of trifluoroacetic acid was treated with three drops of anisole. The resulting solution was stirred at room temperature under nitrogen for 14 hours. All volatiles were removed under vacuum and the residue was purified by medium pressure liquid chromatography on silica, eluting with 0.5% ammonium hydroxide in ethyl acetate to afford 100 mg (0.152 mmol, 54%) of the product. $^1$H NMR (300 MHz, CD$_3$OD): δ 1.40 (s, 6H), 2.00 (m, 1H), 2.32 (m, 1H), 2.5–2.7 (m, 4H), 4.42 (dd; 7, 11 Hz; 1H), 5.05 (m, 3H), 5.32 (d, 15 Hz, 1H), 7.25–7.45 (m, 13H), 7.5–7.7 (m, 3H), 8.13 (m, 1H). FAB-MS: calculated for $C_{36}H_{38}N_4O_6S$ 654; found 677 (M+Na, 85%).

Step G: 3-Benzyloxycarbonylamino-3-methyl-N-[2,3,4,5-tetrahydro-2-oxo-1-[[2'-(benzamido)sulfonyl[1,1'-biphenyl]-4-yl]methyl]-1H-1-benzazepin-3(R)-yl]butanamide To a solution of 50.6 mg of benzoic acid (0.415 mmol, 3.0 eq) in 1 mL of tetrahydrofuran was added 617 mg of N,N'-carbonyldiimidazole (0.415, 3.0 eq) and the mixture was stirred at reflux under nitrogen for one hour. To this mixture was added a solution of 90 mg (0.14 mmol, 1.0 eq) of the intermediate prepared in Step E and 62.2 mg (0.403 mmol, 2.9 eq) of 1,8-diazabicyclo[5.4.0]undece-7-ene (DBU) in 2 mL of tetrahydrofuran. The mixture was stirred at reflux for 24 hours then cooled and diluted with ethyl acetate, then washed with 5% aqueous citric acid. The organic layer was removed, dried over magnesium sulfate, filtered and solvents removed under vacuum. The residue was purified by reverse phase medium pressure liquid chromatography on C8, eluting with methanol/0.1% aqueous trifluoroacetic acid (75/25) to afford 60 mg (0.079 mmol, 57%) of the product. $^1$H NMR (300 MHz, CD$_3$OD): δ 1.39 (s, 6H), 2.02 (m, 1H), 2.34 (m, 1H), 2.50–2.75 (m, 4H), 4.43 (dd; 7, 12 Hz; 1H), 5.0–5.2 (m, 4H), 7.20–7.75 (m, 21H), 8.32 (d, 8 Hz, 1H). FAB-MS: calculated for $C_{43}H_{42}N_4O_7S$ 758; found 782 (M+Na, 20%).

Step H: 3-Amino-3-methyl-N-[2,3,4,5-tetrahydro-2-oxo-1-[[2'-(benzamido)sulfonyl[1,1'-biphenyl]-4-yl]methyl]-1H-1-benzazepin-3(R)-yl]butanamide, trifluoroacetate Hydrobromic acid (0.5 mL of a 30% solution in acetic acid) was added to 30 mg (0.040 mmol) of the intermediate obtained in Step G and the mixture was stirred at room temperature for one hour. All volatiles were removed under vacuum and the residue redissolved in methanol and concentrated to dryness again. The residue was purified by reverse phase medium pressure liquid chromatography on C8, eluting with methanol/0.1% aqueous trifluoroacetic acid (70/30) to afford 29 mg (0.039 mmol, 99%) of the title compound. $^1$H NMR (300 MHz, CD$_3$OD): δ 1.38 (s, 3H), 1.42 (s, 3H), 2.20 (m, 1H), 2.40 (m, 1H), 2.56 (m, 2H), 2.6–2.8 (m, 2H), 4.48 (dd; 8, 11 Hz; 1H), 5.15 (m, 2H), 7.20–7.75 (m, 16H), 8.30 (d, 8 Hz, 1H). FAB-MS: calculated for $C_{35}H_{36}N_4O_5S$ 624; found 625 (M+H, 100%).

EXAMPLE 2

3-Amino-3-methyl-N-[2,3,4,5-tetrahydro-2-oxo-1-[[2'-(ethylamino)sulfonyl[1,1'-biphenyl]-4-yl]methyl]-1H-1-benzazepin-3(R)-yl]butanamide, trifluoroacetate Step A: 1-Bromo-2-ethylbenzenesulfonamide Prepared from o-bromobenzenesulfonyl chloride, ethyl amine hydrochloride and triethylamine by the procedure described in Example 1, Step A. $^1$H NMR (CDCl$_3$, 200 MHz): δ 1.10.(t, 7 Hz, 3H), 2.98 (m, 2H), 5.07 (br s, 1H), 7.43 (m, 2H), 7.74 (dd; 2, 8 Hz; 1H), 8.15 (dd; 2, 8 Hz; 1H). FAB-MS: calculated for C$_8$H$_{10}$BrNO$_2$S 263, 265; found 264, 266 (M+H, 100%).

Step B: 4-Methyl-2'-(ethylamino)sulfonyl-1,1'-biphenyl

Prepared from 1-bromo-2-ethylbenzenesulfonamide and 4-methylphenyltrimethylstannane by the procedure described in Example 1, Step C. $^1$H NMR (200 MHz, CDCl$_3$): δ 0.86 (t, 7Hz, 3H), 2.43 (s, 3H), 2.66 (m, 2H), 3.35 (br t, 1H), 7.20–7.65 (m,7H), 8.15 (dd; 2, 8 Hz; 1H).

Step C: 4-Bromomethyl-2'-(ethylamino)sulfonyl-1,1'-biphenyl

Prepared from 4-methyl-2'-(ethylamino)sulfonyl-1,1'-biphenyl by the procedure described in Example 1, Step D. $^1$H NMR (200 MHz, CDCl$_3$): δ 0.88 (t, 7Hz, 3H), 2.58 (m, 2H), 3.35 (br t, 1H), 4.55 (s, 2H), 7.25–7.65 (m,7H), 8.16 (dd; 2, 8 Hz; 1H).

Step D: 3-Benzyloxycarbonylamino-3-methyl-N-[2,3,4,5-tetrahydro-2-oxo-1-[[2'-(ethylamino)sulfonyl[1,1'-biphenyl]-4-yl]methyl]-1H-1-benzazepin-3(R)-yl]butanamide Prepared from 3-t-butoxycarbonylamino-3-methyl-N-[2,3,4,5-tetrahydro-2-oxo-1H-1-benzazepin-3(R)-yl]butanamide (prepared by the method of Fisher, et al; U.S. Pat. No. 5,206,235) and 4-bromomethyl-2'-(ethylaminosulfonyl)-1,1'-biphenyl by the procedure described in Example 1, Step E. $^1$H NMR (400 MHz, CDCl$_3$): δ 0.77 (t, 7Hz, 3H), 1.33 (s, 6H), 1.40 (s, 9H), 1.47 (s, 3H), 1.87 (m, 1H), 2.35–2.6 (m, 7H), 3.12 (t, 7Hz, 1H), 4.52 (m, 1H), 4.83 (d, 15 Hz, 1H), 5.17 (br s, 1H), 5.38 (d, 15 Hz, 1H), 6.66 (d, 7Hz, 1H), 7.1–7.3 (m, 7H), 7.35 (d, 8 Hz, 2H), 7.46 (m, 1H), 7.55 (m, 1H), 8.10 (d, 8 Hz, 1H). FAB-MS: calculated for C$_{35}$H$_{44}$N$_4$O$_6$S 648; found 649 (M+H, 42%).

Step E: 3-Amino-3-methyl-N-[2,3,4,5-tetrahydro-2-oxo-1-[[2'-(ethylamino)sulfonyl[1,1'-biphenyl]-4-yl]methyl]-1H-1-benzazepin-3(R)-yl]butanamide, trifluoroacetate A solution of 33 mg (0.051 mmol) of the intermediate obtained in Step D in 3 mL of trifluoroacetic acid was treated with three drops of anisole. The resulting solution was stirred at room temperature under nitrogen for 4 hours. All volatiles were removed under vacuum and the residue was purified by reverse phase medium pressure liquid chromatography on C8, eluting with methanol/0.1% aqueous trifluoroacetic acid (70/30) to give the title compound. $^1$H NMR (400 MHz, CDCl$_3$): δ 0.89 (t, 7Hz, 3H), 1.34 (s, sH), 1.38 (s, 3H), 2.14 (m, 1H), 2.34 (m, 1H), 2.52 (m, 2H), 2.65 (m, 4H), 4.42 (dd; 7, 11 Hz; 1H), 5.04 (d, 15 Hz, 1H), 5.25 (d, 15 Hz, 1H), 7.20–7.40 (m, 9H), 7.53 (dt; 2,8 Hz; 1H), 7.62 (dt; 2, 8 Hz; 1H), 8.02 (d, 8 Hz, 1H). FAB-MS: calculated for C$_{30}$H$_{36}$N$_4$O$_4$S 548; found 549 (M+H, 100%).

EXAMPLE 3

3-Amino-3-methyl-N-[2,3,4,5-tetrahydro-2-oxo-1-[[2'-(aminosulfonyl)[1,1'-biphenyl]-4-yl]methyl]-1H-1-benzazepin-3(R)-yl]butanamide, trifluoroacetate The title compound is prepared from 3-benzyloxycarbonylamino-3-methyl-N-[2,3,4,5-tetrahydro-2-oxo-1-[[2'-(t-butylamino)sulfonyl[1,1'-biphenyl]-4-yl]methyl]-1H-1-benzazepin-3(R)-yl]butanamide (Example 1, Step E) by the procedure described in Example 1, Step H

EXAMPLE 4

3-Amino-3-methyl-N-[2,3,4,5-tetrahydro-2-oxo-1-[[2'-(t-butylamino)sulfonyl[1,1'-biphenyl]-4-yl]methyl]-1H-1-benzazepin-3(R)-yl]butanamide, trifluoroacetate 3-Benzyloxycarbonylamino-3-methyl-N-[2,3,4,5-tetrahydro-2-oxo-1-[[2'-(t-butylamino)sulfonyl[1,1'-biphenyl]-4-yl]methyl]-1H-1-benzazepin-3(R)-yl]butanamide (Example 1, Step E) is hydrogenated in methanol in the presence of 20 weight percent palladium hydroxide on carbon catalyst at ambient temperature and one atmosphere of hydrogen for 6 hours. The reaction mixture is filtered through Celite, and concentrated under vacuum. The residue is purified by reverse phase medium pressure liquid chromatography on C8, eluting with methanol/0.1% aqueous trifluoroacetic acid to give the title compound.

EXAMPLE 5

Utilizing the procedures described in Examples 1 to 4 and general methods of organic synthesis described in the chemical literature and familiar to one skilled in the art, the following compounds of Formula 1 can be prepared from the appropriately substituted starting materials and reagents.

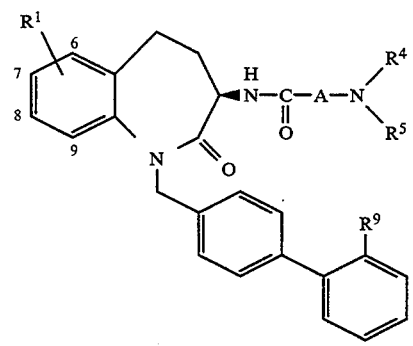

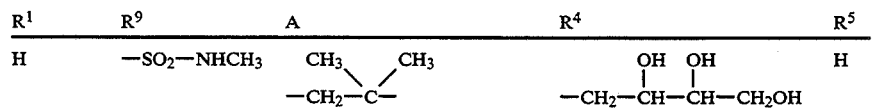

| $R^1$ | $R^9$ | A | $R^4$ | $R^5$ |
|---|---|---|---|---|
| H | —SO$_2$—NHCH$_3$ | —CH$_2$—C(CH$_3$)(CH$_3$)— | —CH$_2$—CH(OH)—CH(OH)—CH$_2$OH | H |

-continued

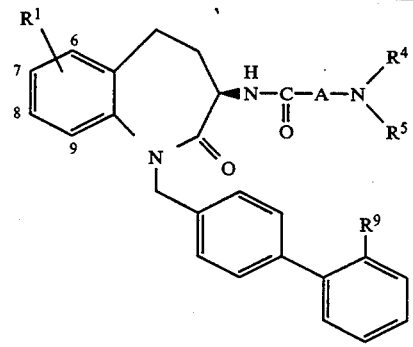

| R¹ | R⁹ | A | R⁴ | R⁵ |
|---|---|---|---|---|
| H | —SO₂—NHCH₃ | —CH₂—C(CH₃)₂— | —CH₂CH₂OH | H |
| H | —SO₂—NHCH₃ | —CH₂—C(CH₃)₂— | —CH₂C(CH₃)₂OH | H |
| H | —SO₂—NHCH₃ | —CH₂—C(CH₃)₂— | —CH₂CH(OH)CH₃ | H |
| H | —SO₂—NHCH₃ | —CH₂—C(CH₃)₂— | —CH₂—C₆H₅ | H |
| H | —SO₂—NHCH₃ | —CH₂—C(CH₃)₂— | —CH₂CH₂CH₃ | H |
| H | —SO₂—NHCH₃ | —CH₂—C(CH₃)₂— | —CH₂—CH(OH)—CH₃ | H |
| 6-F | —SO₂—NHCH₃ | —CH₂—C(CH₃)₂— | H | H |
| 7-F | —SO₂—NHCH₃ | —CH₂—C(CH₃)₂— | H | H |
| 7-CF₃ | —SO₂—NHCH₃ | —CH₂—C(CH₃)₂— | H | H |
| 7-OCH₃ | —SO₂—NHCH₃ | —CH₂—C(CH₃)₂— | H | H |
| 7-OH | —SO₂—NHCH₃ | —CH₂—C(CH₃)₂— | H | H |
| 7-SCH₃ | —SO₂—NHCH₃ | —CH₂—C(CH₃)₂— | H | H |
| 7-S(O)CH₃ | —SO₂—NHCH₃ | —CH₂—C(CH₃)₂— | H | H |
| 8-OCH₃ | —SO₂—NHCH₃ | —CH₂—C(CH₃)₂— | H | H |
| 8-F | —SO₂—NHCH₃ | —CH₂—C(CH₃)₂— | H | H |
| 8-Cl | —SO₂—NHCH₃ | —CH₂—C(CH₃)₂— | H | H |

-continued

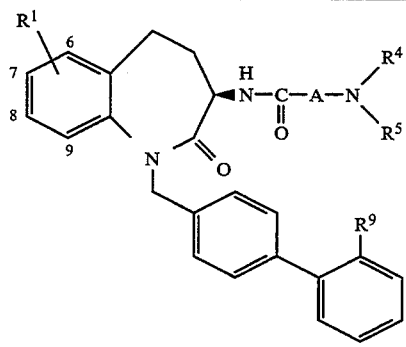

| R¹ | R⁹ | A | R⁴ | R⁵ |
|---|---|---|---|---|
| 8-I | —SO₂—NHCH₃ | —CH₂—C(CH₃)(CH₃)— | H | H |
| H | —SO₂—NHCH₃ | —C(CH₃)(CH₃)— | H | H |
| H | —SO₂—NHCH₃ | —C(H)(CH₃)— | H | H |
| H | —SO₂—NHCH₃ | —C(CH₃)(H)— | H | H |
| H | —SO₂—NHCH₃ | —C(H)(CH₂OH)— | H | H |
| H | —SO₂—NHCH₃ | —C(CH₃)(CH₂OH)— | H | H |
| H | —SO₂—NHCH₃ | —C(H)(CH₃)— | CH₃ | H |
| H | —SO₂—NHCH₃ | —CH₂—C(CH₃)(CH₂OH)— | H | H |
| H | —SO₂—NHCH₃ | —CH₂—C(HOCH₂)(CH₃)— | H | H |
| H | —SO₂—NHCH₃ | —CH₂—C(HOCH₂)(CH₃)— | —CH₂CH(OH)CH₃ | H |
| H | —SO₂—NHCH₃ | —CH₂—C(HOCH₂)(CH₃)— | —CH₂CH(OH)CH₂OH | H |
| H | —SO₂—NHCH₃ | —C(H)(CH₂-phenyl)— | H | H |
| H | —SO₂—NHCH₃ | —C(H)(CH₂-indol-3-yl)— | H | H |
| H | —SO₂—NHCH₃ | —C(H)(CH₂-imidazol-4-yl)— | H | H |

-continued

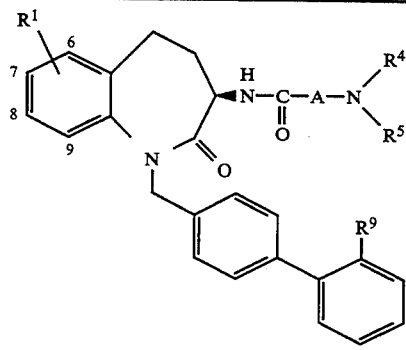

| R¹ | R⁹ | A | R⁴ | R⁵ |
|---|---|---|---|---|
| H | —SO₂—NHCH₃ | 4-piperidinyl (NH) | — | — |
| H | —SO₂—NHCH₃ | 3-piperidinyl (NH) | — | — |
| H | —SO₂—NHCH₃ | 3-quinuclidinyl (N) | — | — |

EXAMPLE 6

Utilizing the procedures described in Examples 1 to 4 and general methods of organic synthesis described in the chemical literature and familiar to one skilled in the art, the following compounds of Formula I can be prepared from the appropriately substituted starting materials and reagents.

| X | n | p | R⁹ | A | R⁴ |
|---|---|---|---|---|---|
| — | 0 | 3 | —SO₂NHCH₃ | —CH₂—C(CH₃)(CH₃)— | H |
| — | 0 | 3 | —SO₂NHCH₃ | —CH₂—C(CH₃)(CH₃)— | —CH₂CH(OH)CH₃ |
| — | 0 | 1 | —SO₂NHCH₃ | —CH₂—C(CH₃)(CH₃)— | H |
| — | 0 | 1 | —SO₂NHCH₃ | —CH₂—C(CH₃)(CH₃)— | —CH₂CH(OH)CH₃ |
| — | 0 | 0 | —SO₂NHCH₃ | —CH₂—C(CH₃)(CH₃)— | H |

-continued

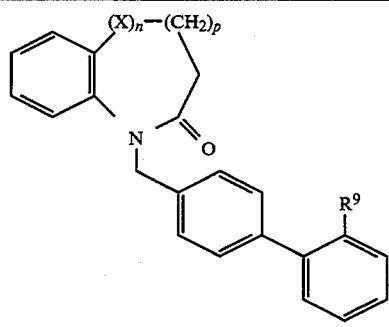

| X | n | p | R⁹ | A | R⁴ |
|---|---|---|---|---|---|
| — | 0 | 0 | —SO$_2$NHCH$_3$ | —CH$_2$—C(CH$_3$)(CH$_3$)— | —CH$_2$CH(OH)CH$_3$ |
| C=O | 1 | 1 | —SO$_2$NHCH$_3$ | —CH$_2$—C(CH$_3$)(CH$_3$)— | —CH$_2$CH(OH)CH$_3$ |
| CHOH | 1 | 1 | —SO$_2$NHCH$_3$ | —CH$_2$—C(CH$_3$)(CH$_3$)— | —CH$_2$CH(OH)CH$_3$ |
| S | 1 | 0 | —SO$_2$NHCH$_3$ | —CH$_2$—C(CH$_3$)(CH$_3$)— | H |
| S | 1 | 0 | —SO$_2$NHCH$_3$ | —C(CH$_3$)(CH$_3$)— | H |
| S | 1 | 0 | —SO$_2$NHCH$_3$ | —CH$_2$—C(CH$_3$)(CH$_3$)— | —CH$_2$CH(OH)CH$_3$ |
| SO | 1 | 0 | —SO$_2$NHCH$_3$ | —CH$_2$—C(CH$_3$)(CH$_3$)— | H |
| SO | 1 | 0 | —SO$_2$NHCH$_3$ | —C(CH$_3$)(CH$_3$)— | H |
| SO | 1 | 0 | —SO$_2$NHCH$_3$ | —CH$_2$—C(CH$_3$)(CH$_3$)— | —CH$_2$CH(OH)CH$_3$ |
| SO | 1 | 0 | —SO$_2$NHCH$_3$ | —CH$_2$—C(CH$_3$)(CH$_3$)— | —CH$_2$CH(OH)CH$_2$OH |
| S | 1 | 2 | —SO$_2$NHCH$_3$ | —CH$_2$—C(CH$_3$)(CH$_3$)— | H |
| S | 1 | 2 | —SO$_2$NHCH$_3$ | —C(CH$_3$)(CH$_3$)— | H |
| S | 1 | 2 | —SO$_2$NHCH$_3$ | —CH$_2$—C(CH$_3$)(CH$_3$)— | —CH$_2$CH(OH)CH$_3$ |
| S | 1 | 2 | —SO$_2$NHCH$_3$ | —CH$_2$—C(CH$_3$)(CH$_3$)— | —CH$_2$CH(OH)CH$_2$OH |
| S | 1 | 2 | —SO$_2$NHCH$_3$ | —CH$_2$—C(CH$_3$)(CH$_3$)— | H |
| S | 1 | 2 | —SO$_2$NHCH$_3$ | —C(CH$_3$)(CH$_3$)— | H |
| S | 1 | 2 | —SO$_2$NHCH$_3$ | —CH$_2$—C(CH$_3$)(CH$_3$)— | —CH$_2$CH(OH)CH$_3$ |

-continued

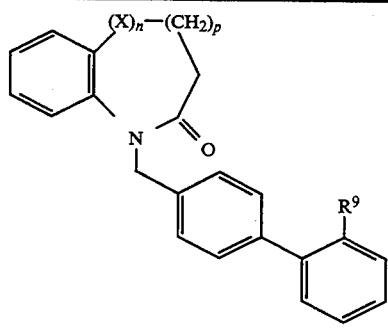

| X | n | p | R⁹ | A | R⁴ |
|---|---|---|---|---|---|
| S | 1 | 2 | —SO₂NHCH₃ | CH₃,,,,,⬩CH₃ / —CH₂—C— | OH / —CH₂CHCH₂OH |
| O | 1 | 1 | —SO₂NHCH₃ | CH₃,,,,,⬩CH₃ / —CH₂—C— | H |
| O | 1 | 1 | —SO₂NHCH₃ | CH₃,,,,,⬩CH₃ / —C— | H |
| O | 1 | 1 | —SO₂NHCH₃ | CH₃,,,,,⬩CH₃ / —CH₂—C— | OH / —CH₂CHCH₃ |
| O | 1 | 1 | —SO₂NHCH₃ | CH₃,,,,,⬩CH₃ / —CH₂—C— | OH / —CH₂CHCH₂OH |

EXAMPLE 7

Utilizing the procedures described in Examples 1 to 4 and general methods of organic synthesis described in the chemical literature and familiar to one skilled in the art, the following compounds of Formula I can be prepared from the appropriately substituted starting materials and reagents.

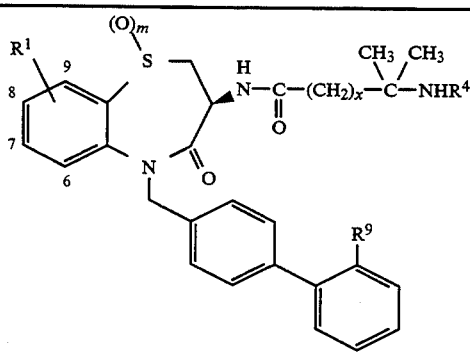

| R¹ | x | m | R⁹ | R⁴ |
|---|---|---|---|---|
| 8-CF₃ | 1 | 0 | —SO₂NH₂ | OH / —CH₂CHCH₃ |
| 8-OCH₃ | 1 | 0 | —SO₂NH₂ | OH / —CH₂CHCH₃ |
| 8-F | 1 | 0 | —SO₂NH₂ | OH / —CH₂CHCH₃ |

-continued

| R¹ | x | m | R⁹ | R⁴ |
|---|---|---|---|---|
| H | 1 | 0 | —SO₂NHCH₃ | OH / —CH₂CHCH₃ |
| H | 1 | 0 | —SO₂NHCH₃ | OH / —CH₂CHCH₃ |
| H | 1 | 0 | —SO₂NHCH₃ | OH / —CH₂CHCH₂OH |
| H | 0 | 0 | —SO₂NHCH₃ | H |
| H | 0 | 0 | —SO₂NHCH₃ | OH / —CH₂CH₂CHCH₃ |
| H | 1 | 1 | —SO₂NHCH₃ | OH / —CH₂CHCH₃ |

-continued

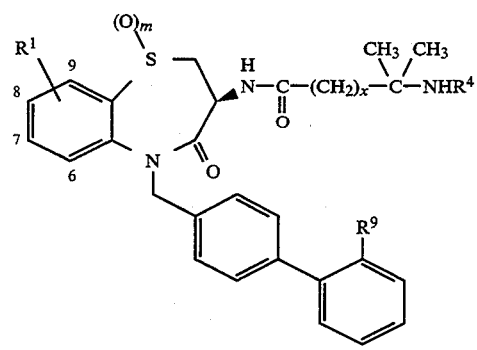

| R¹ | x | m | R⁹ | R⁴ |
|---|---|---|---|---|
| H | 1 | 1 | —SO₂NHCH₃ | —CH₂CHCH₂OH, OH |
| H | 1 | 1 | —SO₂NHCH₃ | —CH₂CHCH₃, OH |
| H | 1 | 1 | —SO₂NHCH₃ | —CH₂CH₂CHCH₃, OH |
| H | 1 | 0 | —SO₂NHCH₃ | —CH₂CHCH₃, OCH₃ |
| 8-F | 1 | 0 | —SO₂NHCH₃ | —CH₂CHCH₃, OH |
| 8-CF₃ | 1 | 0 | —SO₂NHCH₃ | —CH₂CHCH₃, OH |
| 8-OCH₃ | 1 | 0 | —SO₂NHCH₃ | —CH₂CHCH₃, OH |
| 8-SCH₃ | 1 | 0 | —SO₂NHCH₃ | —CH₂CHCH₃, OH |
| 9-F | 1 | 0 | —SO₂NHCH₃ | —CH₂CHCH₃, OH |
| 8-F | 1 | 0 | —SO₂NHCH₃ | —CH₂C(CH₃)₂, OH |

-continued

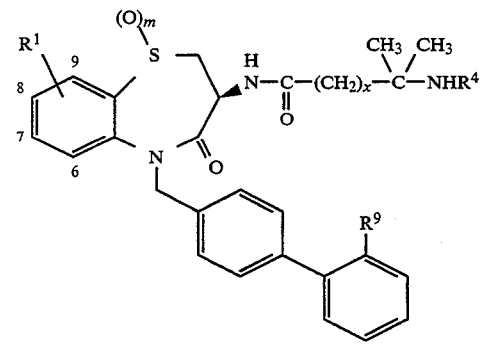

| R¹ | x | m | R⁹ | R⁴ |
|---|---|---|---|---|
| 8-F | 1 | 0 | —SO₂NHCH₃ | —CH₂CH—CH—CH₃, OH OH |
| H | 1 | 0 | —SO₂NHCH₃ | H |
| H | 1 | 0 | —SO₂NH₂ | —CH₂CHCH₃, OH |
| H | 1 | 1 | —SO₂NHCH₃ | —CH₂CHCH₃, OH |
| H | 1 | 0 | —SO₂NH₂ | —CH₂CHCH₂OH, OH |
| H | 1 | 0 | —SO₂NH₂ | —CH₂CH₂CH—CH₃, OH |
| H | 0 | 0 | —SO₂NH₂ | —CH₂CH₂CH—CH₃, OH |
| H | 1 | 0 | —SO₂NH₂ | —CH₂CH—CH—CH₃, OH OH |
| 8-F | 1 | 0 | —SO₂NH₂ | —CH₂CHCH₃, OH |

EXAMPLE 8

Utilizing the procedures described in Examples 1 to 4 and general methods of organic synthesis described in the chemical literature and familiar to one skilled in the art, the following compounds of Formula 1 can be prepared from the appropriately substituted starting materials and reagents.

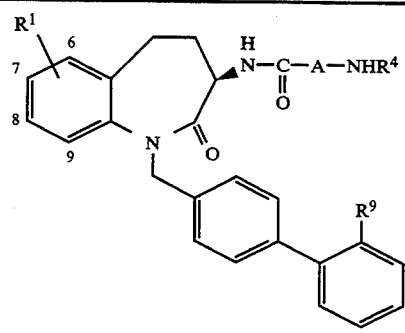

| R¹ | R⁹ | A | R⁴ |
|---|---|---|---|
| H | −SO₂NH−C(=O)−Ph | −CH₂−C(CH₃)(CH₃)− | −CH₂−CH(OH)−CH(OH)−CH₂OH |
| H | −SO₂NH−C(=O)−Ph | −CH₂−C(CH₃)(CH₃)− | −CH₂CH₂OH |
| H | −SO₂NH−C(=O)−Ph | −CH₂−C(CH₃)(CH₃)− | −CH₂C(OH)(CH₃)₂ |
| H | −SO₂NH−C(=O)−Ph | −CH₂−C(CH₃)(CH₃)− | −CH₂CH₂CH(OH)CH₃ |
| H | −SO₂NH−C(=O)−Ph | −CH₂−C(CH₃)(CH₃)− | −CH₂−Ph |
| H | −SO₂NH−C(=O)−Ph | −CH₂−C(CH₃)(CH₃)− | −CH₂CH₂CH₃ |
| H | −SO₂NH−C(=O)−Ph | −CH₂−C(CH₃)(CH₃)− | −CH₃ |
| H | −SO₂NH−C(=O)−NHPh | −C(H)(CH₃)− | H |
| H | −SO₂NH−C(=O)−NHPh | −C(CH₃)(H)− | H |
| H | −SO₂NH−C(=O)−NHPh | −C(H)(CH₂OH)− | H |
| H | −SO₂NH−C(=O)−NHPh | −C(HOCH₂)(H)− | H |
| H | −SO₂NH−C(=O)−NHPh | −C(CH₃)(CH₂OH)− | H |
| H | −SO₂NH−C(=O)−NHPh | −CH₂−C(CH₃)(CH₂OH)− | H |
| H | −SO₂NH−C(=O)−NHPh | −CH₂−C(HOCH₂)(CH₃)− | H |
| H | −SO₂NH−C(=O)−NHCH₂CH₃ | −C(H)(CH₃)− | −CH₂−CH(OH)−CH₃ |

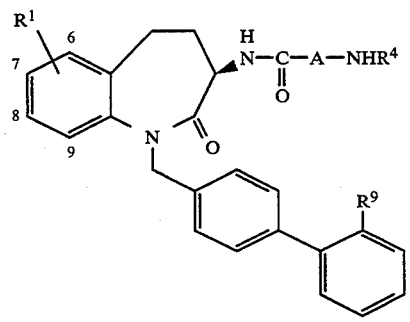

| R¹ | R⁹ | A | R⁴ |
|---|---|---|---|
| H | −SO₂NH−C(O)−NHCH₂CH₃ | −C−(CH₃)(H) | −CH₂−CH(OH)−CH₃ |
| H | −SO₂NH−C(O)−NHCH₂CH₃ | −C−(H)(CH₂OH) | −CH₂−CH(OH)−CH₃ |
| H | −SO₂NH−C(O)−NHCH₂CH₃ | −C−(HOCH₂)(H) | −CH₂−CH(OH)−CH₃ |
| H | −SO₂NH−C(O)−NHCH₂CH₃ | −C−(CH₃)(CH₂OH) | −CH₂−CH(OH)−CH₃ |
| H | −SO₂NH−C(O)−NHCH₂CH₃ | −CH₂−C−(CH₃)(CH₂OH) | −CH₂−CH(OH)−CH₃ |
| H | −SO₂NH−C(O)−NHCH₂CH₃ | −CH₂−C−(HOCH₂)(CH₃) | −CH₂−CH(OH)−CH₃ |
| H | −SO₂NH−C(O)−OCH₂Ph | −C−(H)(CH₃) | −CH₂−CH(OH)−CH₂OH |
| H | −SO₂NH−C(O)−OCH₂Ph | −C−(CH₃)(H) | −CH₂−CH(OH)−CH₂OH |
| H | −SO₂NH−C(O)−OCH₂Ph | −C−(H)(CH₂OH) | −CH₂−CH(OH)−CH₂OH |
| H | −SO₂NH−C(O)−OCH₂Ph | −C−(HOCH₂)(H) | −CH₂−CH(OH)−CH₂OH |
| H | −SO₂NH−C(O)−OCH₂Ph | −C−(CH₃)(CH₂OH) | −CH₂−CH(OH)−CH₂OH |
| H | −SO₂NH−C(O)−OCH₂Ph | −CH₂−C−(CH₃)(CH₂OH) | −CH₂−CH(OH)−CH₂OH |
| H | −SO₂NH−C(O)−OCH₂Ph | −CH₂−C−(HOCH₂)(CH₃) | −CH₂−CH(OH)−CH₂OH |
| 6-f | −SO₂NH−C(O)−NH−C(O)−CH₃ | −CH₂−C−(CH₃)(CH₃) | H |
| 6-OCH₃ | −SO₂NH−C(O)−NH−C(O)−CH₃ | −CH₂−C−(CH₃)(CH₃) | H |
| 7-Br | −SO₂NH−C(O)−NH−C(O)−CH₃ | −CH₂−C−(CH₃)(CH₃) | H |

-continued

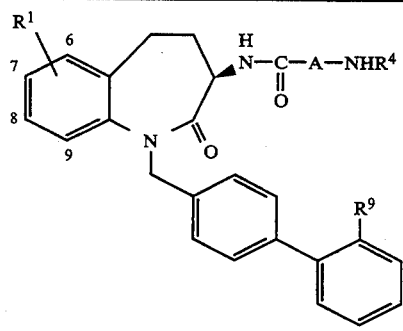

| R¹ | R⁹ | A | R⁴ |
|---|---|---|---|
| 7-Cl | —SO₂NH—C(=O)—NH—C(=O)—CH₃ | —CH₂—C(CH₃)₂— | H |
| 7-CH₃ | —SO₂NH—C(=O)—NH—C(=O)—CH₃ | —CH₂—C(CH₃)₂— | H |
| 8-Cl | —SO₂NH—C(=O)—NH—C(=O)—CH₃ | —CH₂—C(CH₃)₂— | H |
| 8-I | —SO₂NH—C(=O)—NH—C(=O)—CH₃ | —CH₂—C(CH₃)₂— | H |
| H | —SO₂NH—C(=O)—N(CH₃)₂ | —CH₂—C(CH₃)₂— | H |
| H | —SO₂NH—C(=O)—NHCH(CH₃)₂ | —CH₂—C(CH₃)₂— | H |
| H | —SO₂N(CH₃)—C(=O)—NHCH₃ | —CH₂—C(CH₃)₂— | H |
| H | —SO₂NH—C(=O)—NHCH₂Ph | —CH₂—C(CH₃)₂— | H |
| H | —SO₂NH—C(=O)—N(pyrrolidinyl) | —CH₂—C(CH₃)₂— | H |
| H | —SO₂NH—C(=O)—N(morpholinyl) | —CH₂—C(CH₃)₂— | H |
| H | —CH₂NH—C(=O)—N(piperazinyl-NH) | —CH₂—C(CH₃)₂— | H |

EXAMPLE 9

Utilizing the procedures described in Examples 1 to 4 and general methods of organic synthesis described in the chemical literature and familiar to one skilled in the art, the following compounds of Formula I can be prepared from the appropriately substituted starting materials and reagents.

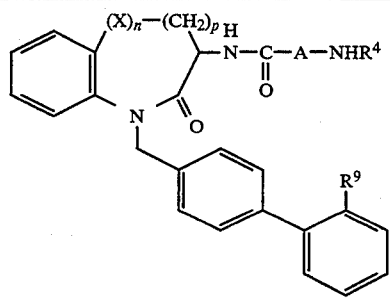

| X | n | p | R⁹ | A | R⁴ |
|---|---|---|---|---|---|
| — | 0 | 3 | —SO₂NH—C(=O)—NHCH₃ | —C(CH₃)(CH₃)— | H |
| — | 0 | 3 | —SO₂NH—C(=O)—NHCH₃ | —CH₂—C(CH₃)(CH₃)— | OH, —CH₂CHCH₃ |
| — | 0 | 3 | —SO₂NH—C(=O)—NHCH₃ | —CH₂—C(CH₃)(CH₃)— | OH, —CH₂CHCH₂OH |
| — | 0 | 1 | —SO₂NH—C(=O)—NHCH₃ | —C(CH₃)(CH₃)— | H |
| — | 0 | 1 | —SO₂NH—C(=O)—NHCH₃ | —CH₂—C(CH₃)(CH₃)— | OH, —CH₂CHCH₃ |
| — | 0 | 1 | —SO₂NH—C(=O)—NHCH₃ | —CH₂—C(CH₃)(CH₃)— | OH, —CH₂CHCH₂OH |
| — | 0 | 0 | —SO₂NH—C(=O)—NHCH₃ | —C(CH₃)(CH₃)— | H |
| — | 0 | 0 | —SO₂NH—C(=O)—NHCH₃ | —CH₂—C(CH₃)(CH₃)— | OH, —CH₂CHCH₃ |
| — | 0 | 0 | —SO₂NH—C(=O)—NHCH₃ | —CH₂—C(CH₃)(CH₃)— | OH, —CH₂CHCH₂OH |
| C=O | 1 | 1 | —SO₂NH—C(=O)—NHCH₃ | —CH₂—C(CH₃)(CH₃)— | OH, —CH₂CHCH₃ |
| CHOH | 1 | 1 | —SO₂NH—C(=O)—NHCH₃ | —CH₂—C(CH₃)(CH₃)— | OH, —CH₂CHCH₃ |
| S | 1 | 0 | —SO₂NH—C(=O)—NHC₂H₅ | —CH₂—C(CH₃)(CH₃)— | H |
| S | 1 | 0 | —SO₂NH—C(=O)—NHCH₂CH₂OH | —C(CH₃)(CH₃)— | H |
| S | 1 | 0 | —SO₂NH—C(=O)—NHCH₃ | —CH₂—C(CH₃)(CH₃)— | OH, —CH₂CHCH₃ |
| SO | 1 | 0 | —SO₂NH—C(=O)—NHCH₃ | —CH₂—C(CH₃)(CH₃)— | H |
| SO | 1 | 0 | —SO₂NH—C(=O)—NH₂ | —C(CH₃)(CH₃)— | H |

-continued

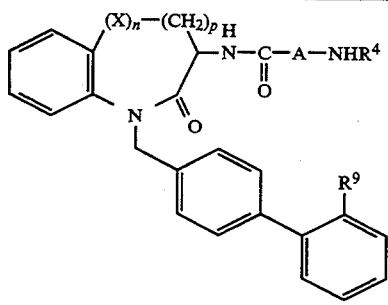

| X | n | p | R⁹ | A | R⁴ |
|---|---|---|---|---|---|
| SO | 1 | 0 | $-SO_2NH-\overset{O}{\overset{\|}{C}}-NH_2$ | $-CH_2-\underset{CH_3}{\overset{CH_3}{C}}-$ | $-CH_2\overset{OH}{\underset{\|}{C}}HCH_3$ |
| SO | 1 | 0 | $-SO_2NH-\overset{O}{\overset{\|}{C}}-NH_2$ | $-CH_2-\underset{CH_3}{\overset{CH_3}{C}}-$ | $-CH_2\overset{OH}{\underset{\|}{C}}HCH_2OH$ |
| S | 1 | 2 | $-SO_2NH-\overset{O}{\overset{\|}{C}}-NH_2$ | $-CH_2-\underset{CH_3}{\overset{CH_3}{C}}-$ | H |
| S | 1 | 2 | $-SO_2NH-\overset{O}{\overset{\|}{C}}-NH_2$ | $-\underset{CH_3}{\overset{CH_3}{C}}-$ | H |
| S | 1 | 2 | $-SO_2NH-\overset{O}{\overset{\|}{C}}-NH_2$ | $-CH_2-\underset{CH_3}{\overset{CH_3}{C}}-$ | $-CH_2\overset{OH}{\underset{\|}{C}}HCH_3$ |
| S | 1 | 2 | $-SO_2NH-\overset{O}{\overset{\|}{C}}-NH_2$ | $-CH_2-\underset{CH_3}{\overset{CH_3}{C}}-$ | $-CH_2\overset{OH}{\underset{\|}{C}}HCH_2OH$ |
| S | 1 | 2 | $-SO_2NH-\overset{O}{\overset{\|}{C}}-NH_2$ | $-CH_2-\underset{CH_3}{\overset{CH_3}{C}}-$ | H |
| S | 1 | 2 | $-SO_2NH-\overset{O}{\overset{\|}{C}}-NHCH_2Ph$ | $-\underset{CH_3}{\overset{CH_3}{C}}-$ | H |
| S | 1 | 2 | $-SO_2NH-\overset{O}{\overset{\|}{C}}-NHC_2H_5$ | $-CH_2-\underset{CH_3}{\overset{CH_3}{C}}-$ | $-CH_2\overset{OH}{\underset{\|}{C}}HCH_3$ |
| S | 1 | 2 | $-SO_2NH-\overset{O}{\overset{\|}{C}}-OPh$ | $-CH_2-\underset{CH_3}{\overset{CH_3}{C}}-$ | $-CH_2\overset{OH}{\underset{\|}{C}}HCH_2OH$ |
| O | 1 | 1 | $-SO_2NH-\overset{O}{\overset{\|}{C}}-NHCH_3$ | $-CH_2-\underset{CH_3}{\overset{CH_3}{C}}-$ | H |
| O | 1 | 1 | $-SO_2NH-\overset{O}{\overset{\|}{C}}-OCH_3$ | $-\underset{CH_3}{\overset{CH_3}{C}}-$ | H |
| O | 1 | 1 | $-SO_2NH-\overset{O}{\overset{\|}{C}}-NH_2$ | $-CH_2-\underset{CH_3}{\overset{CH_3}{C}}-$ | $-CH_2\overset{OH}{\underset{\|}{C}}HCH_3$ |
| O | 1 | 1 | $-SO_2NH-\overset{O}{\overset{\|}{C}}-NHCH_3$ | $-CH_2-\underset{CH_3}{\overset{CH_3}{C}}-$ | $-CH_2\overset{OH}{\underset{\|}{C}}HCH_2OH$ |

What is claimed is:
1. A compound having the formula:

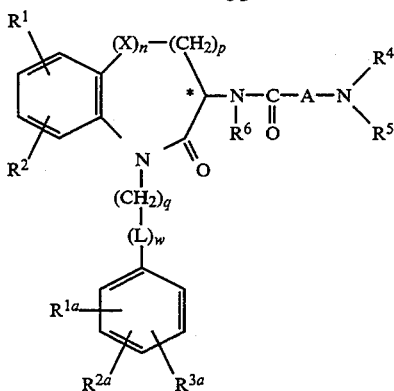

where L is

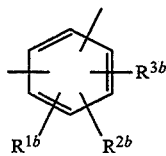

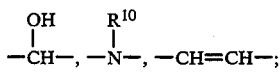

$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, $C_1$-$C_3$ perfluoroalkoxy, —S(O)$_m$R$^{7a}$, cyano, nitro, $R^{7b}$O(CH$_2$)$_v$—, $R^{7b}$COO(CH$_2$)$_v$—, $R^{7b}$OCO(CH$_2$)$_v$—, $R^{12a}R^{12b}$N(CH$_2$)$_v$—, $R^{12a}R^{12b}$NCO(CH$_2$)$_v$—, $R^{12a}R^{12b}$NCOO(CH$_2$)$_v$— phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl or substituted phenyl; phenyl or substituted phenyl where the phenyl substituents are from 1 to 3 of halogen, $C_1$-$C_6$ alkyl, $C_1$-$C_6$ alkoxy, or hydroxy and v is 0 to 3;

$R^{3a}$ and $R^{3b}$ are independently hydrogen, $R^9$, $C_1$-$C_6$ alkyl substituted with $R^9$, phenyl substituted with $R^9$ or phenoxy substituted with $R^9$ with the proviso that either $R^{3a}$ and $R^{3b}$ must be a substitutent other than hydrogen;

$R^9$ is
$R^{4a}R^{12a}$NSO$_2$(CH$_2$)$_v$—,
$R^{4a}R^{12a}$NN(R$^{12b}$)SO$_2$(CH$_2$)$_v$—,
$R^{4a}R^{12a}$NCSN(R$^{12b}$)SO$_2$(CH$_2$)$_v$—,
$R^{4a}R^{12a}$NCON(R$^{12b}$)SO$_2$(CH$_2$)$_v$—,
$R^{4a}R^{12a}$NN(R$^{12b}$)CON(R$^{12b}$)SO$_2$(CH$_2$)$_v$—,
$R^{4a}R^{12a}$NN(R$^{12b}$)CSN(R$^{12b}$)SO$_2$(CH$_2$)$_v$—,
or $R^{13}$OCON(R$^{12b}$)SO$_2$(CH$_2$)$_v$—, where v is 0 to 3;
$R^{12a}$, $R^{12b}$ and $R^{12c}$ are independently $R^{5a}$, OR$^{5a}$ or COR$^{5a}$, $R^{12a}$ and $R^{12b}$, or $R^{12b}$ and $R^{12c}$, or $R^{13}$ and $R^{12b}$, or $R^{12a}$ and $R^{4a}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 3 and $R^1$ and $R^{10}$ are as defined;

$R^{13}$ is $C_1$-$C_3$ perfluoroalkyl, $C_1$-$C_6$ alkyl, substituted $C_1$-$C_6$ alkyl, where the substitutents are hydroxy, —NR$^{10}$R$^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy where $R^{10}$ and $R^{11}$ are independently hydrogen, $C_1$-$C_6$ alkyl, phenyl, phenyl $C_1$-$C_6$ alkyl, $C_1$-$C_5$-alkoxycarbonyl or $C_1$-$C_5$-alkanoyl-$C_1$-$C_6$ alkyl;

$R^4$, $R^{4a}$, $R^5$ and $R^{5a}$ are independently hydrogen, phenyl, substituted phenyl, $C_1$-$C_{10}$ alkyl, substituted $C_1$-$C_{10}$ alkyl, $C_3$-$C_{10}$ alkenyl, substituted $C_3$-$C_{10}$ alkenyl, $C_3$-$C_{10}$ alkynyl or substituted $C_3$-$C_{10}$ alkynyl where the substituents on the phenyl, alkyl, alkenyl or alkynyl are from 1 to 5 of hydroxy, $C_1$-$C_6$ alkoxy, $C_3$-$C_7$ cycloalkyl, fluoro, $R^1$, $R^2$ independently disubstituted phenyl, $R^1$, $R^2$ independently disubstituted phenyl $C_1$-$C_3$ alkoxy, $C_1$-$C_{20}$-alkanoyloxy, $C_1$-$C_5$ alkoxycarbonyl, carboxy, formyl or —NR$^{10}$R$^{11}$ where $R^1$, $R^2$, $R^{10}$ and $R^{11}$ are as defined above; or $R^4$ and $R^5$ can be taken together to form —(CH$_2$)$_r$—B—(CH$_2$)$_s$— where B is CHR$^1$, O, S(O)$_m$ or N—R$^{10}$, r and s are independently 1 to 3, m is 0, 1 or 2 and $R^1$ and $R^{10}$ are as defined above;

$R^6$ is hydrogen, $C_1$-$C_{10}$ alkyl, phenyl or phenyl $C_1$-$C_{10}$ alkyl;

A is $$-(CH_2)_x-\underset{R^{8a}}{\overset{R^8}{C}}-(CH_2)_y-$$

where x and y are independently 0-3;

$R^8$ and $R^{8a}$ are independently hydrogen, $C_1$-$C_{10}$ alkyl, trifluoromethyl, phenyl, substituted $C_1$-$C_{10}$ alkyl where the substitutents are from 1 to 3 of imidazolyl, indolyl, hydroxy, fluoro, —S(O)$_m$R$^{7a}$, $C_1$-$C_6$ alkoxy, $C_3$-$C_7$ cycloalkyl, $R^1$, $R^2$ independently disubstituted phenyl, $R^1$, $R^2$ independently disubstituted phenyl $C_1$-$C_3$ alkoxy, $C_1$-$C_5$ alkanoyloxy, $C_1$-$C_5$ alkoxycarbonyl, carboxy, formyl or —NR$^{10}$R$^{11}$ where $R^1$, $R^2$, $R^{7a}$, $R^{10}$, $R^{11}$ and m are as defined above; or $R^8$ and $R^{8a}$ can be taken together to form —(CH$_2$)$_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from one to five carbon atoms;

and pharmaceutically acceptable salts thereof.

2. A compound of claim 1 wherein:
n is 0 or 1;
p is 0 to 3;
q is 0 to 2;
w is 0 or 1;
X is O, S(O)$_m$, $$-\underset{}{\overset{R^{10}}{N}}-, -CH=CH-;$$

m is 0 to 2;
$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, —S(O)$_m$R$^{7a}$, $R^{7b}$O(CH$_2$)$_v$—, $R^{7b}$COO(CH$_2$)$_v$—, $R^{7b}$OCO(CH$_2$)$_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl where the substitutents are phenyl; phenyl and v is 0 to 2;

$R^{3a}$ and $R^{3b}$ are independently hydrogen, $R^9$, $C_1-C_6$ alkyl substituted with $R^9$, phenyl substituted with $R^9$ or phenoxy substituted with $R^9$ with the proviso that either $R^{3a}$ and $R^{3b}$ must be a substitutent other than hydrogen;

$R^9$ is $R^{4a}R^{12a}NSO_2(CH_2)_v-$,
$R^{4a}R^{12a}NN(R^{12b})SO_2(CH_2)_v-$,
$R^{4a}R^{12a}NCON(R^{12b})SO_2(CH_2)_v-$,
$R^{4a}R^{12a}NN(R^{12b})CON(R^{12b})SO_2(CH_2)_v-$,
or $R^{13}OCON(R^{12b})SO_2(CH_2)_v-$, where v is 0 to 3;

$R^{12a}$, $R^{12b}$ and $R^{12c}$ are independently $R^{5a}$, $OR^{5a}$ or $COR^{5a}$. $R^{12a}$ and $R^{12b}$, or $R^{12b}$ and $R^{12c}$, or $R^{13}$ and $R^{12b}$, or $R^{12a}$ and $R^{4a}$ can be taken together to form $-(CH_2)_r-B-(CH_2)_s-$ where B is $CHR^1$, O, $S(O)_m$ or $NR^{10}$, m is 0, 1 or 2, r and s are independently 0 to 3 and $R^1$ and $R^{10}$ are as defined;

$R^{13}$ is $C_1-C_3$ perfluoroalkyl, $C_1-C_6$ alkyl, substituted $C_1-C_6$ alkyl, where the substitutents are hydroxy, $-NR^{10}R^{11}$, carboxy, phenyl or substituted phenyl; phenyl or substituted phenyl where the substituents on the phenyl are from 1 to 3 of halogen, $C_1-C_6$ alkyl, $C_1-C_6$ alkoxy or hydroxy where $R^{10}$ and $R^{11}$ are independently hydrogen, $C_1-C_6$ alkyl, phenyl, phenyl $C_1-C_6$ alkyl or $C_1-C_5$-alkanoyl-$C_1-C_6$ alkyl;

$R^4$, $R^{4a}$, $R^5$, and $R^{5a}$ are independently hydrogen, phenyl, substituted phenyl, $C_1-C_{10}$ alkyl, substituted $C_1-C_{10}$ alkyl where the substituents on the alkyl or phenyl are from 1 to 5 of hydroxy, $C_1-C_6$ alkoxy, $C_3-C_7$ cycloalkyl, fluoro, $R^1$, $R^2$ independently disubstituted phenyl, $R^1$, $R^2$ independently disubstituted phenyl $C_1-C_3$ alkoxy, $C_1-C_{20}$-alkanoyloxy, $C_1-C_5$ alkoxycarbonyl, carboxy or formyl; $R^4$ and $R^5$ can be taken together to form $-(CH_2)_r-B-(CH_2)_s-$ where B is $CHR^1$, O, $S(O)_m$ or $N-R^{10}$, r and s are independently 1 to 3, m is 0, 1 or 2 and $R^1$ and $R^{10}$ are as defined above;

$R^6$ is hydrogen, $C_1-C_{10}$ alkyl or phenyl $C_1-C_{10}$ alkyl;

A is

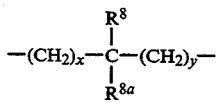

where x and y are independently 0-2;

$R^8$ and $R^{8a}$ are independently hydrogen, $C_1-C_{10}$ alkyl, substituted $C_1-C_{10}$ alkyl where the substitutents are from 1 to 3 of imidazolyl, indolyl, hydroxy, fluoro, $-S(O)_mR^{7a}$, $C_1-C_6$ alkoxy, $R^1$, $R^2$ independently disubstituted phenyl, $C_1-C_5$ alkanoyloxy, $C_1-C_5$ alkoxycarbonyl, carboxy, formyl or $-NR^{10}R^{11}$ where $R^1$, $R^2$, $R^{7a}$, $R^{10}$, $R^{11}$ and m are as defined above; or $R^8$ and $R^{8a}$ can be taken together to form $-(CH_2)_t-$ where t is 2 to 4; and $R^8$ and $R^{8a}$ can independently be joined to one or both of $R^4$ and $R^5$ to form alkylene bridges between the terminal nitrogen and the alkyl portion of the A group wherein the bridge contains from one to five carbon atoms;

and pharmaceutically acceptable salts thereof.

3. A compound of claim 2 wherein:

n is 0 or 1;
p is 0 to 2;
q is 0 to 2;
w is 0 or 1;
X is $S(O)_m$ or $-CH=CH-$;
m is 0 to 1;

$R^1$, $R^2$, $R^{1a}$, $R^{2a}$, $R^{1b}$ and $R^{2b}$ are independently hydrogen, halogen, $C_1-C_7$ alkyl, $C_1-C_3$ perfluoroalkyl, $-S(O)_mR^{7a}$, $R^{7b}O(CH_2)_v-$, $R^{7b}COO(CH_2)_v-$, $R^{7b}O-CO(CH_2)_v-$, phenyl or substituted phenyl where the substituents are from 1 to 3 of halogen, $C_1-C_6$ alkyl, $C_1-C_6$ alkoxy, or hydroxy;

$R^{7a}$ and $R^{7b}$ are independently hydrogen, $C_1-C_6$ alkyl or substituted $C_1-C_6$ alkyl where the substitutents are phenyl and v is 0 to 2;

$R^{3a}$ and $R^{3b}$ are independently hydrogen, $R^9$, $C_1-C_6$ alkyl substituted with $R^9$ or phenoxy substituted with $R^9$ with the proviso that either $R^{3a}$ and $R^{3b}$ must be a substitutent other than hydrogen;

$R^9$ is $R^{4a}R^{12a}NSO_2(CH_2)_v-$,
$R^{4a}R^{12a}NN(R^{12b})SO_2(CH_2)_v-$,
$R^{4a}R^{12a}NCON(R^{12b})SO_2(CH_2)_v-$,
or $R^{13}OCON(R^{12b})SO_2(CH_2)_v-$, where v is 0 to 2;

$R^{12a}$, $R^{12b}$ and $R^{12c}$ are independently $R^{5a}$ or $COR^{5a}$. $R^{12a}$ and $R^{12b}$, or $R^{12b}$ and $R^{12c}$, or $R^{13}$ and $R^{12b}$, or $R^{12a}$ and $R^{4a}$ can be taken together to form $-(CH_2)_r-B-(CH_2)_s-$ where B is $CHR^1$, O, $S(O)_m$ or $NR^{10}$, m is 0, 1 or 2, r and s are independently 0 to 2 and $R^1$ and $R^{10}$ are as defined;

$R^{13}$ is $C_1-C_6$ alkyl, substituted $C_1-C_6$ alkyl, where the substitutents are phenyl or substituted phenyl; phenyl or substituted phenyl where the substituents on the phenyl are from 1 to 3 of halogen, $C_1-C_6$ alkyl, $C_1-C_6$ alkoxy or hydroxy;

$R^4$, $R^{4a}$, $R^5$ and $R^{5a}$ are independently hydrogen, $C_1-C_{10}$ alkyl or substituted $C_1-C_{10}$ alkyl where the substituents are from 1 to 5 of hydroxy, $C_1-C_6$ alkoxy, fluoro, $R^1$, $R^2$ independently disubstituted phenyl, $C_1-C_{20}$-alkanoyloxy, $C_1-C_5$ alkoxycarbonyl or carboxy; where $R^1$ and $R^2$ are as defined above;

$R^6$ is hydrogen or $C_1-C_{10}$ alkyl;

A is

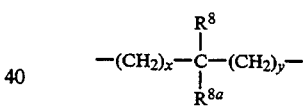

where x and y are independently 0-2;

$R^8$ and $R^{8a}$ are independently hydrogen, $C_1-C_{10}$ alkyl, substituted $C_1-C_{10}$ alkyl where the substitutents are from 1 to 3 of imidazolyl, indolyl, hydroxy, fluoro, $-S(O)_mR^{7a}$, $C_1-C_6$ alkoxy, $R^1$, $R^2$ independently disubstituted phenyl, $C_1-C_5$ alkanoyloxy, $C_1-C_5$ alkoxycarbonyl or carboxy where $R^1$, $R^2$, $R^{7a}$ and m are as defined above; or $R^8$ and $R^{8a}$ can be taken together to form $-(CH_2)_t-$ where t is 2; and $R^8$ and $R^{8a}$ can independently be joined to one or both of $R^4$ and $R^5$ to form alkylene bridges between the terminal nitrogen and the alkyl portion of the A group wherein the bridge contains from one to five carbon atoms;

and pharmaceutically acceptable salts thereof.

4. A compound of claim 3 wherein:

n is 0 or 1;
p is 0 to 2;
q is 1;
w is 1;
X is $S(O)_m$ or $-CH=CH-$;
m is 0 to 1;

$R^1$, $R^2$, $R^{1a}$, $R^{2a}$, $R^{1b}$ and $R^{2b}$ are independently hydrogen, halogen, $C_1-C_7$ alkyl, $C_1-C_3$ perfluoroalkyl, $-S(O)_mR^{7a}$, $R^{7b}O(CH_2)_v-$, $R^{7b}COO(CH_2)_v-$, phenyl or substituted phenyl where the substituents are from 1 to 3 of halogen, $C_1-C_6$ alkyl, $C_1-C_6$ alkoxy, or hydroxy;

$R^{7a}$ and $R^{7b}$ are independently hydrogen, $C_1$-$C_6$ alkyl or substituted $C_1$-$C_6$ alkyl where the substitutents are phenyl and v is 0 or 1;

$R^{3a}$ and $R^{3b}$ are independently hydrogen, $R^9$ or $C_1$-$C_6$ alkyl substituted with $R^9$, with the proviso that either $R^{3a}$ and $R^{3b}$ must be a substituent other than hydrogen; $R^9$ is $R^{4a}R^{12a}NSO_2(CH_2)_v$—, $R^{4a}R^{12a}NCON(R^{12b})SO_2(CH_2)_v$—, or $R^{13}OCON(R^{12b})SO_2(CH_2)_v$— where v is 0 or 1;

$R^{12a}$, $R^{12b}$ and $R^{12c}$ are independently $R^{5a}$ or $COR^{5a}$. $R^{12a}$ and $R^{12b}$, or $R^{12b}$ and $R^{12c}$, or $R^{13}$ and $R^{12b}$, or $R^{12a}$ and $R^{4a}$ can be taken together to form —($CH_2$)$_r$—B—($CH_2$)$_s$— where B is $CHR^1$, O, $S(O)_m$ or $NR^{10}$, m is 0, 1 or 2, r and s are independently 0 to 2 and $R^1$ and $R^{10}$ are as defined;

$R^{13}$ is $C_1$-$C_6$ alkyl, substituted $C_1$-$C_6$ alkyl, where the substitutents are phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

$R^4$, $R^{4a}$, $R^5$ and $R^{5a}$ are independently hydrogen, $C_1$-$C_{10}$ alkyl or substituted $C_1$-$C_{10}$ alkyl where the substituents are from 1 to 3 of hydroxy, $C_1$-$C_3$ alkoxy, fluoro, $R^1$, $R^2$ independently disubstituted phenyl, $C_1$-$C_{20}$-alkanoyloxy, $C_1$-$C_5$ alkoxycarbonyl or carboxy; where $R^1$ and $R^2$ are as defined above;

$R^6$ is hydrogen;

A is

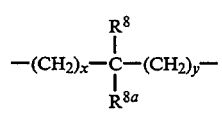

where x and y are independently 0 or 1;

$R^8$ and $R^{8a}$ are independently hydrogen, $C_1$-$C_{10}$ alkyl, substituted $C_1$-$C_{10}$ alkyl where the substitutents are from 1 to 3 of imidazolyl, indolyl, hydroxy, fluoro, —$S(O)_mR^{7a}$, $C_1$-$C_6$ alkoxy, $R^1$, $R^2$ independently disubstituted phenyl, $C_1$-$C_5$ alkanoyloxy, $C_1$-$C_5$ alkoxycarbonyl or carboxy where $R^1$, $R^2$, $R^{7a}$ and m are as defined above; or $R^8$ and $R^{8a}$ can be taken together to form —($CH_2$)$_t$— where t is 2; and $R^8$ and $R^{8a}$ can independently be joined to one or both of $R^4$ and $R^5$ to form alkylene bridges between the terminal nitrogen and the alkyl portion of the A group wherein the bridge contains from one to five carbon atoms;

and pharmaceutically acceptable salts thereof.

5. A stereospecific compound of claim 1 having the following structural formula:

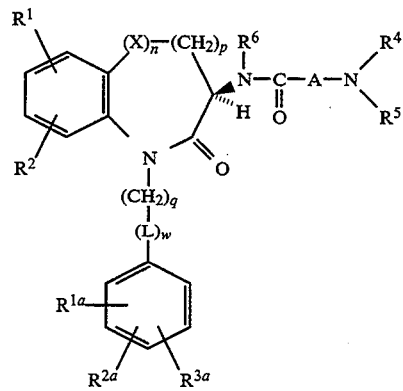

where $R^1$, $R^2$, $R^{1a}$, $R^{2a}$, $R^{3a}$, $R^4$, $R^5$, $R^6$, X, L, A, n, p, q and w are as defined in claim 1.

6. A compound which is selected from:

3-Amino-3-methyl-N-[1-[[2'-(benzamido)sulfonyl[1,1'-biphenyl]-4-yl]methyl]-2,3,4,5-tetrahydro-2-oxo-1H-1-benzazepin-3(R)-yl]butanamide;

3-Amino-3-methyl-N-[1-[[2'-(benzamido)sulfonyl[1,1'-biphenyl]-4-yl]methyl]-7-fluoro-2,3,4,5-tetrahydro-2-oxo-1H-1-benzazepin-3(R)-yl]butanamide;

3-Amino-3-methyl-N-[1-[[2'-(benzamido)sulfonyl[1,1'-biphenyl]-4-yl]methyl]-7-trifluoromethyl-2,3,4,5-tetrahydro-2-oxo-1H-1-benzazepin-3(R)-yl]butanamide;

3-Amino-3-methyl-N-[1-[[2'-(benzamido)sulfonyl[1,1'-biphenyl]-4-yl]methyl]-7-methylthio-2,3,4,5-tetrahydro-2-oxo-1H-1-benzazepin-3(R)-yl]butanamide;

3-Amino-3-methyl-N-[1-[[2'-(benzamido)sulfonyl[1,1'-biphenyl]-4-yl]methyl]-7-methoxy-2,3,4,5-tetrahydro-2-oxo-1H-1-benzazepin-3(R)-yl]butanamide;

2-Amino-2-methyl-N-[1-[[2'-(benzamido)sulfonyl[1,1'-biphenyl]-4-yl]methyl]-2,3,4,5-tetrahydro-2-oxo-1H-1-benzazepin-3(R)-yl]propanamide;

2-Amino-2-methyl-N-[1-[[2'-(benzamido)sulfonyl[1,1'-biphenyl]-4-yl]methyl]-7-fluoro-2,3,4,5-tetrahydro-2-oxo-1H-1-benzazepin-3(R)-yl]propanamide;

2-Amino-2-methyl-N-[1-[[2'-(benzamido)sulfonyl[1,1'-biphenyl]-4-yl]methyl]-7-trifluoromethyl-2,3,4,5-tetrahydro-2-oxo-1H-1-benzazepin-3(R)-yl]propanamide;

2-Amino-2-methyl-N-[1-[[2'-(benzamido)sulfonyl[1,1'-biphenyl]-4-yl]methyl]-7-methylthio-2,3,4,5-tetrahydro-2-oxo-1H-1-benzazepin-3(R)-yl]propanamide;

2-Amino-2-methyl-N-[1-[[2'-(benzamido)sulfonyl[1,1'-biphenyl]-4-yl]methyl]-7-methoxy-2,3,4,5-tetrahydro-2-oxo-1H-1-benzazepin-3(R)-yl]propanamide;

3-[2(R)-Hydroxypropyl]amino-3-methyl-N-[1-[[2'-(benzamido)sulfonyl[1,1'-biphenyl]-4-yl]methyl]-2,3,4,5-tetrahydro-2-oxo-1H-1-benzazepin-3(R)-yl]butanamide;

3-[2(R)-Hydroxypropyl]amino-3-methyl-N-[1-[[2'-(benzamido)sulfonyl[1,1'-biphenyl]-4-yl]methyl]-7-fluoro-2,3,4,5-tetrahydro-2-oxo-1H-1-benzazepin-3(R)-yl]butanamide;

3-[2(R)-Hydroxypropyl]amino-3-methyl-N-[1-[[2'-(benzamido)sulfonyl[1,1'-biphenyl]-4-yl]methyl]-7-trifluoromethyl-2,3,4,5-tetrahydro-2-oxo-1H-1-benzazepin-3(R)-yl]butanamide;

3-[2(R)-Hydroxypropyl]amino-3-methyl-N-[1-[[2'-(benzamido)sulfonyl[1,1'-biphenyl]-4-yl]methyl]-7-methylthio-2,3,4,5-tetrahydro-2-oxo-1H-1-benzazepin-3(R)-yl]butanamide;

3-[2(R)-Hydroxypropyl]amino-3-methyl-N-[1-[[2'-(benzamido)sulfonyl[1,1'-biphenyl]-4-yl]methyl]-7-methoxy-2,3,4,5-tetrahydro-2-oxo-1H-1-benzazepin-3(R)-yl]butanamide;

3-[2(S),3-Dihydroxypropyl]amino-3-methyl-N-[1-[[2'-(benzamido)sulfonyl[1,1'-biphenyl]-4-yl]methyl]-2,3,4,5-tetrahydro-2-oxo-1H-1-benzazepin-3(R)-yl]butanamide;

3-[2(S),3-Dihydroxypropyl]amino-3-methyl-N-[1-[[2'-(benzamido)sulfonyl[1,1'-biphenyl]-4-yl]methyl]-7-fluoro-2,3,4,5-tetrahydro-2-oxo-1H-1-benzazepin-3(R)-yl]butanamide;

3-[2(S),3-Dihydroxypropyl]amino-3-methyl-N-[1-[[2'-(benzamido)sulfonyl[1,1'-biphenyl]-4-yl]methyl]-7-trifluoromethyl-2,3,4,5-tetrahydro-2-oxo, 1H-1-benzazepin-3(R)-yl]butanamide;

3-[2(S),3-Dihydroxypropyl]amino-3-methyl-N-[1-[[2'-(benzamido)sulfonyl[1,1'-biphenyl]-4-yl]methyl]-7-methylthio-2,3,4,5-tetrahydro-2oxo-1H-1-benzazepin-3(R)-yl]butanamide;

3-[2(S),3-Dihydroxypropyl]amino-3-methyl-N-[1-[[2'-(benzamido)sulfonyl[1,1'-biphenyl]-4-yl]methyl]-7-methoxy-2,3,4,5-tetrahydro-2-oxo-1H-1-benzazepin-3(R)-yl]butanamide;

3-Amino-3-methyl-N-[1-[[2'-(ethylamino)sulfonyl[1,1'-biphenyl]-4-yl]methyl]-2,3,4,5-tetrahydro-2-oxo-1H-1-benzazepin-3(R)-yl]butanamide;

3-Amino-3-methyl-N-[1-[[2'-(ethylamino)sulfonyl[1,1'-biphenyl]-4-yl]methyl]-7-fluoro-2,3,4,5-tetrahydro-2-oxo-1H-1-benzazepin-3(R)-yl]butanamide;

3-Amino-3-methyl-N-[1-[[2'-(ethylamino)sulfonyl[1,1'-biphenyl]-4-yl]methyl]-7-trifluoromethyl-2,3,4,5-tetrahydro-2-oxo-1H-1-benzazepin-3(R)-yl]butanamide;

3-Amino-3-methyl-N-[1-[[2'-(ethylamino)sulfonyl[1,1'-biphenyl]-4-yl]methyl]-7-methylthio-2,3,4,5-tetrahydro-2-oxo-1H-1-benzazepin-3(R)-yl]butanamide;

3-Amino-3-methyl-N-[1-[[2'-(ethylamino)sulfonyl[1,1'-biphenyl]-4-yl]methyl]-7-methoxy-2,3,4,5-tetrahydro-2-oxo-1H-1-benzazepin-3(R)-yl]butanamide;

2-Amino-2-methyl-N-[1-[[2'-(ethylamino)sulfonyl[1,1'-biphenyl]-4-yl]methyl]-2,3,4,5-tetrahydro-2-oxo-1H-1-benzazepin-3(R)-yl]propanamide;

2-Amino-2-methyl-N-[1-[[2'-(ethylamino)sulfonyl[1,1'-biphenyl]-4-yl]methyl]-7-fluoro-2,3,4,5-tetrahydro-2-oxo-1H-1-benzazepin-3(R)-yl]propanamide;

2-Amino-2-methyl-N-[1-[[2'-(ethylamino)sulfonyl[1,1'-biphenyl]-4-yl]methyl]-7-trifluoromethyl-2,3,4,5-tetrahydro-2-oxo-1H-1-benzazepin-3(R)-yl]propanamide;

2-Amino-2-methyl-N-[1-[[2'-(ethylamino)sulfonyl[1,1'-biphenyl]-4-yl]methyl]-7-methylthio-2,3,4,5-tetrahydro-2-oxo-1H-1-benzazepin-3(R)-yl]propanamide;

2-Amino-2-methyl-N-[1-[[2'-(ethylamino)sulfonyl[1,1'-biphenyl]-4-yl]methyl]-7-methoxy-2,3,4,5-tetrahydro-2-oxo-1H-1-benzazepin-3(R)-yl]propanamide 3-[2(R)-Hydroxypropyl]amino-3-methyl-N-[1-[[2'-(ethylamino)sulfonyl[1,1'-biphenyl]-4-yl]methyl]-2,3,4,5-tetrahydro-2-oxo-1H-1-benzazepin-3(R)-yl]butanamide;

3-[2(R)-Hydroxypropyl]amino-3-methyl-N-[1-[[2'-(ethylamino)sulfonyl[1,1'-biphenyl]-4-yl]methyl]-7-fluoro-2,3,4,5-tetrahydro-2-oxo-1H-1-benzazepin-3(R)-yl]butanamide;

3-[2(R)-Hydroxypropyl]amino-3-methyl-N-[1-[[2'-(ethylamino)sulfonyl[1,1'-biphenyl]-4-yl]methyl]-7-trifluoromethyl-2,3,4,5-tetrahydro-2-oxo-1H-1-benzazepin-3(R)-yl]butanamide;

3-[2(R)-Hydroxypropyl]amino-3-methyl-N-[1-[[2'-(ethylamino)sulfonyl[1,1'-biphenyl]-4-yl]methyl]-7-methylthio-2,3,4,5-tetrahydro-2-oxo-1H-1-benzazepin-3(R)-yl]butanamide;

3-[2(R)-Hydroxypropyl]amino-3-methyl-N-[1-[[2'-(ethylamino)sulfonyl[1,1'-biphenyl]-4-yl]methyl]-7-methoxy-2,3,4,5-tetrahydro-2-oxo-1H-1-benzazepin-3(R)-yl]butanamide;

3-[2(S),3-Dihydroxypropyl]amino-3-methyl-N-[1-[[2'-(ethylamino)sulfonyl[1,1'-biphenyl]-4-yl]methyl]-2,3,4,5-tetrahydro-2-oxo-1H-1-benzazepin-3(R)-yl]butanamide;

3-[2(S),3-Dihydroxypropyl]amino-3-methyl-N-[1-[[2'-(ethylamino)sulfonyl[1,1'-biphenyl]-4-yl]methyl]-7-fluoro-2,3,4,5-tetrahydro,2-oxo-1H-1-benzazepin-3(R)-yl]butanamide;

3-[2(S),3-Dihydroxypropyl]amino-3-methyl-N-[1-[[2'-(ethylamino)sulfonyl[1,1'-biphenyl]-4-yl]methyl]-7-trifluoromethyl-2,3,4,5-tetrahydro-2-oxo-1H-1-benzazepin-3(R)-yl]butanamide;

3-[2(S),3-Dihydroxypropyl]amino-3-methyl-N-[1-[[2'-(ethylamino)sulfonyl[1,1'-biphenyl]-4-yl]methyl]-7-methylthio-2,3,4,5-tetrahydro-2oxo-1H-1-benzazepin-3(R)-yl]butanamide;

3-[2(S),3-Dihydroxypropyl]amino-3-methyl-N-[1-[[2'-(ethylamino)sulfonyl[1,1'-biphenyl]-4-yl]methyl]-7-methoxy-2,3,4,5-tetrahydro-2oxo-1H-1-benzazepin-3(R)-yl]butanamide;

3-Amino-3-methyl-N-[1-[[2'-(aminosulfonyl)[1,1'-biphenyl]-4-yl]methyl]-2,3,4,5-tetrahydro-2-oxo-1H-1-benzazepin-3(R)-yl]butanamide;

3-Amino-3-methyl-N-[1-[[2'-(aminosulfonyl)[1,1'-biphenyl]-4-yl]methyl]-7-fluoro-2,3,4,5-tetrahydro-2-oxo-1H-1-benzazepin-3(R)-yl]butanamide;

3-Amino-3-methyl-N-[1-[[2'-(aminosulfonyl)[1,1'-biphenyl]-4-yl]methyl]-7-trifluoromethyl-2,3,4,5-tetrahydro-2-oxo-1H-1-benzazepin-3(R)-yl]butanamide;

3-Amino-3-methyl-N-[1-[[2'-(aminosulfonyl)[1,1'-biphenyl]-4-yl]methyl]-7-methylthio-2,3,4,5-tetrahydro-2-oxo-1H-1-benzazepin-3(R)-yl]butanamide;

3-Amino-3-methyl-N-[1-[[2'-(aminosulfonyl)[1,1'-biphenyl]-4-yl]methyl]-7-methoxy-2,3,4,5-tetrahydro-2-oxo-1H-1-benzazepin-3(R)-yl]butanamide;

2-Amino-2-methyl-N-[1-[[2'-(aminosulfonyl)[1,1'-biphenyl]-4-yl]methyl]-2,3,4,5-tetrahydro-2-oxo-1H-1-benzazepin-3(R)-yl]propanamide;

2-Amino-2-methyl-N-[1-[[2'-(aminosulfonyl)[1,1'-biphenyl]-4-yl]methyl]-7-fluoro-2,3,4,5-tetrahydro-2-oxo-1H-1-benzazepin-3(R)-yl]propanamide;

2-Amino-2-methyl-N-[1-[[2'-(aminosulfonyl)[1,1'-biphenyl]-4-yl]methyl]-7-trifluoromethyl-2,3,4,5-tetrahydro-2-oxo-1H-1-benzazepin-3(R)-yl]propanamide;

2-Amino-2-methyl-N-[1-[[2'-(aminosulfonyl)[1,1'-biphenyl]-4-yl]methyl]-7-methylthio-2,3,4,5-tetrahydro-2-oxo-1H-1-benzazepin-3(R)-yl]propanamide;

2-Amino-2-methyl-N-[1-[[2'-(aminosulfonyl)[1,1'-biphenyl]-4-yl]methyl]-7-methoxy-2,3,4,5-tetrahydro-2-oxo-1H-1-benzazepin-3(R)-yl]propanamide;

3-[2(R)-Hydroxypropyl]amino-3-methyl-N-[1-[[2'-(aminosulfonyl)[1,1'-biphenyl]-4-yl]methyl]-2,3,4,5-tetrahydro-2-oxo-1H-1-benzazepin-3(R)-yl]butanamide;

3-[2(R)-Hydroxypropyl]amino-3-methyl-N-[1-[[2'-(aminosulfonyl)[1,1'-biphenyl]-4-yl]methyl]-7-fluoro-2,3,4,5-tetrahydro-2-oxo-1H-1-benzazepin-3(R)-yl]butanamide;

3-[2(R)-Hydroxypropyl]amino-3-methyl-N-[1-[[2'-(aminosulfonyl)[1,1'-biphenyl]-4-yl]methyl]-7-trifluoromethyl-2,3,4,5-tetrahydro-2-oxo-1H-1-benzazepin-3(R)-yl]butanamide;

-[2(R)-Hydroxypropyl]amino-3-methyl-N-[1-[[2'-(aminosulfonyl)[1,1'-biphenyl]-4-yl]methyl]-7-methylthio-2,3,4,5-tetrahydro-2-oxo-1H-1-benzazepin-3(R)-yl]butanamide;

3-[2(R)-Hydroxypropyl]amino-3-methyl-N-[1-[[2'-(aminosulfonyl)[1,1'-biphenyl]-4-yl]methyl]-7-methoxy-2,3,4,5-tetrahydro-2-oxo-1H-1-benzazepin-3(R)-yl]butanamide;

3-[2(S),3-Dihydroxypropyl]amino-3-methyl-N-[1-[[2'-(aminosulfonyl)[1,1'-biphenyl]-4-yl]methyl]-2,3,4,5-tetrahydro-2-oxo-1H-1-benzazepin-3(R)-yl]butanamide;

3-[2(S),3-Dihydroxypropyl]amino-3-methyl-N-[1-[[2'-(aminosulfonyl)[1,1'-biphenyl]-4-yl]methyl]-7-fluoro-2,3,4,5-tetrahydro-2-oxo-1H-1-benzazepin-3(R)-yl]butanamide;

3-[2(S),3-Dihydroxypropyl]amino-3-methyl-N-[1-[[2'-(aminosulfonyl)[1,1'-biphenyl]-4-yl]methyl]-7-trifluoromethyl-2,3,4,5-tetrahydro-2-oxo-1H-1-benzazepin-3(R)-yl]butanamide;

3-[2(S),3-Dihydroxypropyl]amino-3-methyl-N-[1-[[2'-(aminosulfonyl)[1,1'-biphenyl]-4-yl]methyl]-7-methylthio-2,3,4,5-tetrahydro-2-oxo-1H-1-benzazepin-3(R)-yl]butanamide;

3-[2(S),3-Dihydroxypropyl]amino-3-methyl-N-[1-[[2'-(aminosulfonyl)[1,1'-biphenyl]-4-yl]methyl]-7-methoxy-2,3,4,5-tetrahydro-2-oxo-1H-1-benzazepin-3(R)-yl]butanamide;

3-Amino-3-methyl-N-[1-[[2'-(t-butylamino)sulfonyl[1,1'-biphenyl]-4-yl]methyl]-2,3,4,5-tetrahydro-2-oxo-1H-1-benzazepin-3(R)-yl]butanamide;

3-Amino-3-methyl-N-[1-[[2'-(t-butylamino)sulfonyl[1,1'-biphenyl]-4-yl]methyl]-7-fluoro-2,3,4,5-tetrahydro-2-oxo-1H-1-benzazepin-3(R)-yl]butanamide;

3-Amino-3-methyl-N-[1-[[2'-(t-butylamino)sulfonyl[1,1'-biphenyl]-4-yl]methyl]-7-trifluoromethyl-2,3,4,5-tetrahydro-2-oxo-1H-1-benzazepin-3(R)-yl]butanamide;

3-Amino-3-methyl-N-[1-[[2'-(t-butylamino)sulfonyl[1,1'-biphenyl]-4-yl]methyl]-7-methylthio-2,3,4,5-tetrahydro-2-oxo-1H-1-benzazepin-3(R)-yl]butanamide;

3-Amino-3-methyl-N-[1-[[2'-(t-butylamino)sulfonyl[1,1'-biphenyl]-4-yl]methyl]-7-methoxy-2,3,4,5-tetrahydro-2-oxo-1H-1-benzazepin-3(R)-yl]butanamide;

2-Amino-2-methyl-N-[1-[[2'-(t-butylamino)sulfonyl[1,1'-biphenyl]-4-yl]methyl]-2,3,4,5-tetrahydro-2-oxo-1H-1-benzazepin-3(R)-yl]propanamide;

2-Amino-2-methyl-N-[1-[[2'-(t-butylamino)sulfonyl[1,1'-biphenyl]-4-yl]methyl]-7-fluoro-2,3,4,5-tetrahydro-2-oxo-1H-1-benzazepin-3(R)-yl]propanamide;

2-Amino-2-methyl-N-[1-[[2'-(t-butylamino)sulfonyl[1,1'-biphenyl]-4-yl]methyl]-7-trifluoromethyl-2,3,4,5-tetrahydro-2-oxo-1H-1-benzazepin-3(R)-yl]propanamide;

2-Amino-2-methyl-N-[1-[[2'-(t-butylamino)sulfonyl[1,1'-biphenyl]-4-yl]methyl]-7-methylthio-2,3,4,5-tetrahydro-2-oxo-1H-1-benzazepin-3(R)-yl]propanamide;

2-Amino-2-methyl-N-[1-[[2'-(t-butylamino)sulfonyl[1,1'-biphenyl]-4-yl]methyl]-7-methoxy-2,3,4,5-tetrahydro-2-oxo-1H-1-benzazepin-3(R)-yl]propanamide;

3-[2(R)-Hydroxypropyl]amino-3-methyl-N-[1-[[2'-(t-butylamino)sulfonyl[1,1'-biphenyl]-4-yl]methyl]-2,3,4,5-tetrahydro-2-oxo-1H-1-benzazepin-3(R)-yl]butanamide;

3-[2(R)-Hydroxypropyl]amino-3-methyl-N-[1-[[2'-(t-butylamino)sulfonyl[1,1'-biphenyl]-4-yl]methyl]-7-fluoro-2,3,4,5-tetrahydro-2-oxo-1H-1-benzazepin-3(R)-yl]butanamide;

3-[2(R)-Hydroxypropyl]amino-3-methyl-N-[1-[[2'-(t-butylamino)sulfonyl[1,1'-biphenyl]-4-yl]methyl]-7-trifluoromethyl-2,3,4,5-tetrahydro-2-oxo-1H-1-benzazepin-3(R)-yl]butanamide;

3-[2(R)-Hydroxypropyl]amino-3-methyl-N-[1-[[2'-(t-butylamino)sulfonyl[1,1'-biphenyl]-4-yl]methyl]-7-methylthio-2,3,4,5-tetrahydro-2-oxo-1H-1-benzazepin-3(R)-yl]butanamide;

3-[2(R)-Hydroxypropyl]amino-3-methyl-N-[1-[[2'-(t-butylamino)sulfonyl[1,1'-biphenyl]-4-yl]methyl]-7-methoxy-2,3,4,5-tetrahydro-2-oxo-1H-1-benzazepin-3(R)-yl]butanamide;

3-[2(S),3-Dihydroxypropyl]amino-3-methyl-N-[1-[[2'-(t-butylamino)sulfonyl[1,1'-biphenyl]-4-yl]methyl]-2,3,4,5-tetrahydro-2-oxo-1H-1-benzazepin-3(R)-yl]butanamide;

3-[2(S),3-Dihydroxypropyl]amino-3-methyl-N-[1-[[2'-(t-butylamino)sulfonyl[1,1'-biphenyl]-4-yl]methyl]-7-fluoro-2,3,4,5-tetrahydro-2-oxo-1H-1-benzazepin-3(R)-yl]butanamide;

3-[2(S),3-Dihydroxypropyl]amino-3-methyl-N-[1-[[2'-(t-butylamino)sulfonyl[1,1'-biphenyl]-4-yl]methyl]-7-trifluoromethyl-2,3,4,5-tetrahydro-2-oxo-1H-1-benzazepin-3(R)-yl]butanamide;

3-[2(S),3-Dihydroxypropyl]amino-3-methyl-N-[1-[[2'-(t-butylamino)sulfonyl[1,1'-biphenyl]-4-yl]methyl]-7-methylthio-2,3,4,5-tetrahydro-2-oxo-1H-1-benzazepin-3(R)-yl]butanamide;

3-[2(S),3-Dihydroxypropyl]amino-3-methyl-N-[1-[[2'-(t-butylamino)sulfonyl[1,1'-biphenyl]-4-yl]methyl]-7-methoxy-2,3,4,5-tetrahydro-2-oxo-1H-1-benzazepin-3(R)-yl]butanamide;

3-Amino-3-methyl-N-[5-[[2'-(benzamido)sulfonyl[1,1'-biphenyl]-4-yl]methyl]-2,3,4,5-tetrahydro-4-oxo-1,5-benzothiazepin-3(S)-yl]butanamide;

3-Amino-3-methyl-N-[5-[[2'-(benzamido)sulfonyl[1,1'-biphenyl]-4-yl]methyl]-8-fluoro-2,3,4,5-tetrahydro-4-oxo-1,5-benzothiazepin-3(S)-yl]butanamide;

3-Amino-3-methyl-N-[5-[[2'-(benzamido)sulfonyl[1,1'-biphenyl]-4-yl]methyl]-8-trifluoromethyl-2,3,4,5-tetrahydro-4-oxo-1,5-benzothiazepin-3(S)-yl]butanamide;

3-Amino-3-methyl-N-[5-[[2'-(benzamido)sulfonyl[1,1'-biphenyl]-4-yl]methyl]-8-methylthio-2,3,4,5-tetrahydro-4-oxo-1,5-benzothiazepin-3(S)-yl]butanamide;

3-Amino-3-methyl-N-[5-[[2'-(benzamido)sulfonyl[1,1'-biphenyl]-4-yl]methyl]-8-methoxy-2,3,4,5-tetrahydro-4-oxo-1,5-benzothiazepin-3(S)-yl]butanamide;

2-Amino-2-methyl-N-[5-[[2'-(benzamido)sulfonyl[1,1'-biphenyl]-4-yl]methyl]-2,3,4,5-tetrahydro-4-oxo-1,5-benzothiazepin-3(S)-yl]propanamide;

2-Amino-2-methyl-N-[5-[[2'-(benzamido)sulfonyl[1,1'-biphenyl]-4-yl]methyl]-8-fluoro-2,3,4,5-tetrahydro-4-oxo-1,5-benzothiazepin-3(S)-yl]propanamide;

2-Amino-2-methyl-N-[5-[[2'-(benzamido)sulfonyl[1,1'-biphenyl]-4-yl]methyl]-8-trifluoromethyl-2,3,4,5-tetrahydro-4-oxo-1,5-benzothiazepin-3(S)-yl]propanamide;

2-Amino-2-methyl-N-[5-[[2'-(benzamido)sulfonyl[1,1'-biphenyl]-4-yl]methyl]-8-methyl thio-2,3,4,5-tetrahydro-4-oxo-1,5-benzothiazepin-3(S)-yl]propanamide;

2-Amino-2-methyl-N-[5-[[2'-(benzamido)sulfonyl[1,1'-biphenyl]-4-yl]methyl]-8-methoxy-2,3,4,5-tetrahydro-4-oxo-1,5-benzothiazepin-3(S)-yl]propanamide;

3-[2(R)-Hydroxypropyl]amino-3-methyl-N-[5-[[2'-(benzamido)sulfonyl[1,1'-biphenyl]-4-yl]methyl]-2,3,4,5-tetrahydro-4-oxo-1,5-benzothiazepin-3(S)-yl]butanamide;

-[2(R)-Hydroxypropyl]amino-3-methyl-N-[5-[[2'-(benzamido)sulfonyl-[1,1'-biphenyl]-4-yl]methyl]-8-fluoro-2,3,4,5-tetrahydro-4-oxo-1,5-benzothiazepin-3(S)-yl]butanamide;

-[2(R)-Hydroxypropyl]amino-3-methyl-N-[5-[[2'-(benzamido)sulfonyl-[1,1'-biphenyl]-4-yl]methyl]-8-trifluoromethyl-2,3,4,5-tetrahydro-4-oxo-1,5-benzothiazepin-3(S)-yl]butanamide;

-[2(R)-Hydroxypropyl]amino-3-methyl-N-[5-[[2'-(benzamido)sulfonyl-[1,1'-biphenyl]-4-yl]methyl]-8-methylthio-2,3,4,5-tetrahydro-4-oxo-1,5-benzothiazepin-3(S)-yl]butanamide;

-[2(R)-Hydroxypropyl]amino-3-methyl-N-[5-[[2'-(benzamido)sulfonyl-[1,1'-biphenyl]-4-yl]methyl]-8-methoxy-2,3,4,5-tetrahydro-4-oxo-1,5-benzothiazepin-3(S)-yl]butanamide;

3-[2(S),3-Dihydroxypropyl]amino-3-methyl-N-[5-[[2'-(benzamido)sulfonyl[1,1'-biphenyl]-4-yl]methyl]-2,3,4,5-tetrahydro-4-oxo-1,5-benzothiazepin-3(S)-yl]butanamide;

3-[2(S),3-Dihydroxypropyl]amino-3-methyl-N-[5-[[2'-(benzamido)sulfonyl[1,1'-biphenyl]-4-yl]methyl]-8-fluoro-2,3,4,5-tetrahydro-4-oxo-1,5-benzothiazepin-3(S)-yl]butanamide;

3-[2(S),3-Dihydroxypropyl]amino-3-methyl-N-[5-[[2'-(benzamido)sulfonyl[1,1'-biphenyl]-4-yl]methyl]-8-trifluoromethyl-2,3,4,5-tetrahydro-4-oxo-1,5-benzothiazepin-3(S)-yl]butanamide;

3-[2(S),3-Dihydroxypropyl]amino-3-methyl-N-[5-[[2'-(benzamido)sulfonyl[1,1'-biphenyl]-4-yl]methyl]-8-methylthio-2,3,4,5-tetrahydro-4-oxo-1,5-benzothiazepin-3(S)-yl]butanamide;

3-[2(S),3-Dihydroxypropyl]amino-3-methyl-N-[5-[[2'-(benzamido)sulfonyl[1,1'-biphenyl]-4-yl]methyl]-8-methoxy-2,3,4,5-tetrahydro-4-oxo-1,5-benzothiazepin-3(S)-yl]butanamide;

3-Amino-3-methyl-N-[5-[[2'-(ethylamino)sulfonyl[1,1'-biphenyl]-4-yl]methyl]-2,3,4,5-tetrahydro-4-oxo-1,5-benzothiazepin-3(S)-yl]butanamide;

3-Amino-3-methyl-N-[5-[[2'-(ethylamino)sulfonyl[1,1'-biphenyl]-4-yl]methyl]-8-fluoro-2,3,4,5-tetrahydro-4-oxo-1,5-benzothiazepin-3(S)-yl]butanamide;

3-Amino-3-methyl-N-[5-[[2'-(ethylamino)sulfonyl[1,1'-biphenyl]-4-yl]methyl]-8-trifluoromethyl-2,3,4,5-tetrahydro-4-oxo-1,5-benzothiazepin-3(S)-yl]butanamide;

3-Amino-3-methyl-N-[5-[[2'-(ethylamino)sulfonyl[1,1'-biphenyl]-4-yl]methyl]-8-methyl thio-2,3,4,5-tetrahydro-4-oxo-1,5-benzothiazepin-3(S)-yl]butanamide;

3-Amino-3-methyl-N-[5-[[2'-(ethylamino)sulfonyl[1,1'-biphenyl]-4-yl]methyl]-8-methoxy-2,3,4,5-tetrahydro-4-oxo-1,5-benzothiazepin-3(S)-yl]butanamide;

2-Amino-2-methyl-N-[5-[[2'-(ethylamino)sulfonyl[1,1'-biphenyl]-4-yl]methyl]-2,3,4,5-tetrahydro-4-oxo-1,5-benzothiazepin-3(S)-yl]propanamide;

2-Amino-2-methyl-N-[5-[[2'-(ethylamino)sulfonyl[1,1'-biphenyl]-4-yl]methyl]-8-fluoro-2,3,4,5-tetrahydro-4-oxo-1,5-benzothiazepin-3(S)-yl]propanamide;

2-Amino-2-methyl-N-[5-[[2'-(ethylamino)sulfonyl[1,1'-biphenyl]-4-yl]methyl]-8-trifluoromethyl-2,3,4,5-tetrahydro-4-oxo-1,5-benzothiazepin-3(S)-yl]propanamide;

2-Amino-2-methyl-N-[5-[[2'-(ethylamino)sulfonyl[1,1'-biphenyl]-4-yl]methyl]-8-methyl thio-2,3,4,5-tetrahydro-4-oxo-1,5-benzothiazepin-3(S)-yl]propanamide;

2-Amino-2-methyl-N-[5-[[2'-(ethylamino)sulfonyl[1,1'-biphenyl]-4-yl]methyl]-8-methoxy-2,3,4,5-tetrahydro-4-oxo-1,5-benzothiazepin-3(S)-yl]propanamide;

3-[2(R)-Hydroxypropyl]amino-3-methyl-N-[5-[[2'-(ethylamino)sulfonyl[1,1'-biphenyl]-4-yl]methyl]-2,3,4,5-tetrahydro-4-oxo-1,5-benzothiazepin-3(S)-yl]butanamide;

3-[2(R)-Hydroxypropyl]amino-3-methyl-N-[5-[[2'-(ethylamino)sulfonyl[1,1'-biphenyl]-4-yl]methyl]-8-fluoro-2,3,4,5-tetrahydro-4-oxo-1,5-benzothiazepin-3(S)-yl]butanamide;

3-[2(R)-Hydroxypropyl]amino-3-methyl-N-[5-[[2'-(ethylamino)sulfonyl[1,1'-biphenyl]-4-yl]methyl]-8-trifluoromethyl-2,3,4,5-tetrahydro-4-oxo-1,5-benzothiazepin-3(S)-yl]butanamide;

3-[2(R)-Hydroxypropyl]amino-3-methyl-N-[5-[[2'-(ethylamino)sulfonyl[1,1'-biphenyl]-4-yl]methyl]-8-methylthio-2,3,4,5-tetrahydro-4-oxo-1,5-benzothiazepin-3(S)-yl]butanamide;

3-[2(R)-Hydroxypropyl]amino-3-methyl-N-[5-[[2'-(ethylamino)sulfonyl[1,1'-biphenyl]-4-yl]methyl]-8-methoxy-2,3,4,5-tetrahydro-4-oxo-1,5-benzothiazepin-3(S)-yl]butanamide;

3-[2(S),3-Dihydroxypropyl]amino-3-methyl-N-[5-[[2'-(ethylamino)sulfonyl[1,1'-biphenyl]-4-yl]methyl]-2,3,4,5-tetrahydro-4-oxo-1,5-benzothiazepin-3(S)-yl]butanamide;

3-[2(S),3-Dihydroxypropyl]amino-3-methyl-N-[5-[[2'-(ethylamino)sulfonyl[1,1'-biphenyl]-4-yl]methyl]-8-fluoro-2,3,4,5-tetrahydro-4-oxo-1,5-benzothiazepin-3(S)-yl]butanamide;

3-[2(S),3-Dihydroxypropyl]amino-3-methyl-N-[5-[[2'-(ethylamino)sulfonyl[1,1'-biphenyl]-4-yl]methyl]-8-trifluoromethyl-2,3,4,5-tetrahydro-4-oxo-1,5-benzothiazepin-3(S)-yl]butanamide;

3-[2(S),3-Dihydroxypropyl]amino-3-methyl-N-[5-[[2'-(ethylamino)sulfonyl[1,1'-biphenyl]-4-yl]methyl]-8-methylthio-2,3,4,5-tetrahydro-4-oxo-1,5-benzothiazepin-3(S)-yl]butanamide;

3-[2(S),3-Dihydroxypropyl]amino-3-methyl-N-[5-[[2'-(ethylamino)sulfonyl[1,1'-biphenyl]-4-yl]methyl]-8-methoxy-2,3,4,5-tetrahydro-4-oxo-1,5-benzothiazepin-3(S)-yl]butanamide;

3-Amino-3-methyl-N-[5-[[2'-(aminosulfonyl)[1,1'-biphenyl]-4-yl]methyl]-2,3,4,5-tetrahydro-4-oxo-1,5-benzothiazepin-3(S)-yl]butanamide;

3-Amino-3-methyl-N-[5-[[2'-(aminosulfonyl)[1,1'-biphenyl]-4-yl]methyl]-8-fluoro-2,3,4,5-tetrahydro-4-oxo-1,5-benzothiazepin-3(S)-yl]butanamide;

3-Amino-3-methyl-N-[5-[[2'-(aminosulfonyl)[1,1'-biphenyl]-4-yl]methyl]-8-trifluoromethyl-2,3,4,5-tetrahydro-4-oxo-1,5-benzothiazepin-3(S)-yl]butanamide;

3-Amino-3-methyl-N-[5-[[2'-(aminosulfonyl)[1,1'-biphenyl]-4-yl]methyl]-8-methylthio-2,3,4,5-tetrahydro-4-oxo-1,5-benzothiazepin-3(S)-yl]butanamide;

3-Amino-3-methyl-N-[5-[[2'-(aminosulfonyl)[1,1'-biphenyl]-4-yl]methyl]-8-methoxy-2,3,4,5-tetrahydro-4-oxo-1,5-benzothiazepin-3(S)-yl]butanamide;

2-Amino-2-methyl-N-[5-[[2'-(aminosulfonyl)[1,1'-biphenyl]-4-yl]methyl]-2,3,4,5-tetrahydro-4-oxo-1,5-benzothiazepin-3(S)-yl]propanamide;

2-Amino-2-methyl-N-[5-[[2'-(aminosulfonyl)[1,1'-biphenyl]-4-yl]methyl]-8-fluoro-2,3,4,5-tetrahydro-4-oxo-1,5-benzothiazepin-3(S)-yl]propanamide;

2-Amino-2-methyl-N-[5-[[2'-(aminosulfonyl)[1,1'-biphenyl]-4-yl]methyl]-8-trifluoromethyl-2,3,4,5-tetrahydro-4-oxo-1,5-benzothiazepin-3(S)-yl]propanamide;

2-Amino-2-methyl-N-[5-[[2'-(aminosulfonyl)[1,1'-biphenyl]-4-yl]methyl]-8-methylthio-2,3,4,5-tetrahydro-4-oxo-1,5-benzothiazepin-3(S)-yl]propanamide;

2-Amino-2-methyl-N-[5-[[2'-(aminosulfonyl)[1,1'-biphenyl]-4-yl]methyl]-8-methoxy-2,3,4,5-tetrahydro-4-oxo-1,5-benzothiazepin-3(S)-yl]propanamide;

3-[2(R)-Hydroxypropyl]amino-3-methyl-N-[5-[[2'-(aminosulfonyl)[1,1'-biphenyl]-4-yl]methyl]-2,3,4,5-tetrahydro-4-oxo-1,5-benzothiazepin-3(S)-yl]butanamide;

3-[2(R)-Hydroxypropyl]amino-3-methyl-N-[5-[[2'-(aminosulfonyl)[1,1'-biphenyl]-4-yl]methyl]-8-fluoro-2,3,4,5-tetrahydro-4-oxo-1,5-benzothiazepin-3(S)-yl]butanamide;

3-[2(R)-Hydroxypropyl]amino-3-methyl-N-[5-[[2'-(aminosulfonyl)[1,1'-biphenyl]-4-yl]methyl]-8-trifluoromethyl-2,3,4,5-tetrahydro-4-oxo-1,5-benzothiazepin-3(S)-yl]butanamide;

3-[2(R)-Hydroxypropyl]amino-3-methyl-N-[5-[[2'-(aminosulfonyl)[1,1'-biphenyl]-4-yl]methyl]-8-methylthio-2,3,4,5-tetrahydro-4-oxo-1,5-benzothiazepin-3(S)-yl]butanamide;

3-[2(R)-Hydroxypropyl]amino-3-methyl-N-[5-[[2'-(aminosulfonyl)[1,1'-biphenyl]-4-yl]methyl]-8-methoxy-2,3,4,5-tetrahydro-4-oxo-1,5-benzothiazepin-3(S)-yl]butanamide;

3-[2(S),3-Dihydroxypropyl]amino-3-methyl-N-[5-[[2'-(aminosulfonyl)[1,1'-biphenyl]-4-yl]methyl]-2,3,4,5-tetrahydro-4-oxo-1,5-benzothiazepin-3(S)-yl]butanamide;

3-[2(S),3-Dihydroxypropyl]amino-3-methyl-N-[5-[[2'-(aminosulfonyl)[1,1'-biphenyl]-4-yl]methyl]-8-fluoro-2,3,4,5-tetrahydro-4-oxo-1,5-benzothiazepin-3(S)-yl]butanamide;

3-[2(S),3-Dihydroxypropyl]amino-3-methyl-N-[5-[[2'-(aminosulfonyl)[1,1'-biphenyl]-4-yl]methyl]-8-trifluoromethyl-2,3,4,5-tetrahydro-4-oxo-1,5-benzothiazepin-3(S)-yl]butanamide;

3-[2(S),3-Dihydroxypropyl]amino-3-methyl-N-[5-[[2'-(aminosulfonyl)[1,1'-biphenyl]-4-yl]methyl]-8-methylthio-2,3,4,5-tetrahydro-4-oxo-1,5-benzothiazepin-3(S)-yl]butanamide;

3-[2(S),3-Dihydroxypropyl]amino-3-methyl-N-[5-[[2'-(aminosulfonyl)[1,1'-biphenyl]-4-yl]methyl]-8-methoxy-2,3,4,5-tetrahydro-4-oxo-1,5-benzothiazepin-3(S)-yl]butanamide;

3-Amino-3-methyl-N-[5-[[2'-(t-butylamino)sulfonyl[1,1'-biphenyl]-4-yl]methyl]-2,3,4,5-tetrahydro-4-oxo-1,5-benzothiazepin-3(S)-yl]butanamide;

3-Amino-3-methyl-N-[5-[[2'-(t-butylamino)sulfonyl[1,1'-biphenyl]-4-yl]methyl]-8-fluoro-2,3,4,5-tetrahydro-4-oxo-1,5-benzothiazepin-3(S)-yl]butanamide;

3-Amino-3-methyl-N-[5-[[2'-(t-butylamino)sulfonyl[1,1'-biphenyl]-4-yl]methyl]-8-trifluoromethyl-2,3,4,5-tetrahydro-4-oxo-1,5-benzothiazepin-3(S)-yl]butanamide;

3-Amino-3-methyl-N-[5-[[2'-(t-butylamino)sulfonyl[1,1'-biphenyl]-4-yl]methyl]-8-methylthio-2,3,4,5-tetrahydro-4-oxo-1,5-benzothiazepin-3(S)-yl]butanamide;

3-Amino-3-methyl-N-[5-[[2'-(t-butylamino)sulfonyl[1,1'-biphenyl]-4-yl]methyl]-8-methoxy-2,3,4,5-tetrahydro-4-oxo-1,5-benzothiazepin-3(S)-yl]butanamide;

2-Amino-2-methyl-N-[5-[[2'-(t-butylamino)sulfonyl[1,1'-biphenyl]-4-yl]methyl]-2,3,4,5-tetrahydro-4-oxo-1,5-benzothiazepin-3(S)-yl]propanamide;

2-Amino-2-methyl-N-[5-[[2'-(t-butylamino)sulfonyl[1,1'-biphenyl]-4-yl]methyl]-8-fluoro-2,3,4,5-tetrahydro-4-oxo-1,5-benzothiazepin-3(S)-yl]propanamide;

2-Amino-2-methyl-N-[5-[[2'-(t-butylamino)sulfonyl[1,1'-biphenyl]-4-yl]methyl]-8-trifluoromethyl-2,3,4,5-tetrahydro-4-oxo-1,5-benzothiazepin-3(S)-yl]propanamide;

2-Amino-2-methyl-N-[5-[[2'-(t-butylamino)sulfonyl[1,1'-biphenyl]-4-yl]methyl]-8-methylthio-2,3,4,5-tetrahydro-4-oxo-1,5-benzothiazepin-3(S)-yl]propanamide;

2-Amino-2-methyl-N-[5-[[2'-(t-butylamino)sulfonyl[1,1'-biphenyl]-4-yl]methyl]-8-methoxy -2,3,4,5-tetrahydro-4-oxo-1,5-benzothiazepin-3(S)-yl]propanamide;

3-[2(R)-Hydroxypropyl]amino-3-methyl-N-[5-[[2'-(t-butylamino)sulfonyl[1,1'-biphenyl]-4-yl]methyl]-2,3,4,5-tetrahydro-4-oxo-1,5-benzothiazepin-3(S)-yl]butanamide;

3-[2(R)-Hydroxypropyl]amino-3-methyl-N-[5-[[2'-(t-butylamino)sulfonyl[1,1'-biphenyl]-4-yl]methyl]-8-fluoro-2,3,4,5-tetrahydro-4-oxo-1,5-benzothiazepin-3(S)-yl]butanamide;

3-[2(R)-Hydroxypropyl]amino-3-methyl-N-[5-[[2'-(t-butylamino)sulfonyl[1,1'-biphenyl]-4-yl]methyl]-8-trifluoromethyl-2,3,4,5-tetrahydro-4-oxo-1,5-benzothiazepin-3(S)-yl]butanamide;

3-[2(R)-Hydroxypropyl]amino-3-methyl-N-[5-[[2'-(t-butylamino)sulfonyl[1,1'-biphenyl]-4-yl]methyl]-8-methylthio-2,3,4,5-tetrahydro-4-oxo-1,5-benzothiazepin-3(S)-yl]butanamide;

3-[2(R)-Hydroxypropyl]amino-3-methyl-N-[5-[[2'-(t-butylamino)sulfonyl[1,1'-biphenyl]-4-yl]methyl]-8-methoxy-2,3,4,5-tetrahydro-4-oxo-1,5-benzothiazepin-3(S)-yl]butanamide;

3-[2(S),3-Dihydroxypropyl]amino-3-methyl-N-[5-[[2'-(t-butylamino)sulfonyl[1,1'-biphenyl]-4-yl]methyl]-2,3,4,5-tetrahydro-4-oxo-1,5-benzothiazepin-3(S)-yl]butanamide;

3-[2(S),3-Dihydroxypropyl]amino-3-methyl-N-[5-[[2'-(t-butylamino)sulfonyl[1,1'-biphenyl]-4-yl]methyl]-8-fluoro-2,3,4,5-tetrahydro-4-oxo-1,5-benzothiazepin-3(S)-yl]butanamide;

3-[2(S),3-Dihydroxypropyl]amino-3-methyl-N-[5-[[2'-(t-butylamino)sulfonyl[1,1'-biphenyl]-4-yl]methyl]-8-trifluoromethyl-2,3,4,5-tetrahydro-4-oxo-1,5-benzothiazepin-3(S)-yl]butanamide;

3-[2(S),3-Dihydroxypropyl]amino-3-methyl-N-[5-[[2'-(t-butylamino)sulfonyl[1,1'-biphenyl]-4-yl]methyl]-8-methylthio-2,3,4,5-tetrahydro-4-oxo-1,5-benzothiazepin-3(S)-yl]butanamide; and 3-[2(S),3-Dihydroxypropyl]amino-3-methyl-N-[5-[[2'-(t-butylamino)sulfonyl[1,1'-biphenyl]-4-yl]methyl]-8-methoxy-2,3,4,5-tetrahydro-4-oxo-1,5-benzothiazepin-3(S)-yl]butanamide.

* * * * *